US006350774B1

(12) United States Patent
Bach et al.

(10) Patent No.: US 6,350,774 B1
(45) Date of Patent: *Feb. 26, 2002

(54) ANTITHROMBOTIC AGENTS

(75) Inventors: Nicholas J Bach, Indianapolis; Jolie A. Bastian, Beech Grove; Nickolay Y Chirgadze, Carmel; Michael L Denney, Franklin, all of IN (US); Robert J. Foglesong, Durham, NC (US); Richard W Harper, Indianapolis, IN (US); Mary G Johnson, Durham, NC (US); Ho-Shen Lin, Indianapolis, IN (US); Michael P Lynch, Raleigh, NC (US); Jefferson R McCowan, Indianapolis, IN (US); Alan D Palkowitz, Carmel, IN (US); Daniel J Sall, Greenwood, IN (US); Gerald F Smith; Kumiko Takeuchi, both of Indianapolis, IN (US); Minsheng Zhang, Warren, NJ (US)

(73) Assignee: Eli Lilly And Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/423,165

(22) PCT Filed: Apr. 30, 1998

(86) PCT No.: PCT/US98/08830

§ 371 Date: Jan. 24, 2000

§ 102(e) Date: Jan. 24, 2000

(87) PCT Pub. No.: WO98/49161

PCT Pub. Date: Nov. 5, 1998

Related U.S. Application Data

(60) Provisional application No. 60/044,297, filed on Apr. 30, 1997.

(51) Int. Cl.$^7$ .......................... A61K 31/38; A61P 7/02; C07D 409/14
(52) U.S. Cl. ................ 514/422; 514/443; 548/187; 548/229; 548/254; 548/203; 548/311.4; 548/518; 548/523; 548/525
(58) Field of Search ................. 548/523, 525; 514/422

(56) References Cited

U.S. PATENT DOCUMENTS

| | | |
|---|---|---|
| 3,274,213 A | 9/1966 | Lednicer |
| 3,293,263 A | 12/1966 | Lednicer |
| 4,001,426 A | 1/1977 | Brenner et al. |
| 4,007,204 A | 2/1977 | Descamps et al. |
| 4,133,814 A | 1/1979 | Jones et al. |
| 4,418,068 A | 11/1983 | Jones et al. |
| 5,371,091 A | 12/1994 | Misra et al. |
| 5,441,965 A | 8/1995 | Sall et al. |
| 5,472,962 A | 12/1995 | Koizumi et al. |
| 5,510,357 A | 4/1996 | Palkowitz |
| 5,518,735 A | 5/1996 | Sturzebecher et al. |
| 5,523,309 A | 6/1996 | Bryant et al. |
| 5,532,254 A * | 7/1996 | Bowling ..................... 548/523 |
| 5,567,828 A | 10/1996 | Dodge et al. |
| 5,576,343 A | 11/1996 | Nagahara et al. |
| 6,025,382 A | 2/2000 | Bastian et al. |

FOREIGN PATENT DOCUMENTS

| | | |
|---|---|---|
| EP | 617030 | 9/1994 |
| WO | WO 95/10513 | 4/1995 |
| WO | WO 95/17095 | 6/1995 |
| WO | WO 95/17382 | 6/1995 |
| WO | WO 96/03375 | 2/1996 |
| WO | WO 96/11677 | 4/1996 |
| WO | WO 97/25033 | 7/1997 |

OTHER PUBLICATIONS

Bastian et al, *Chem Abstracts*, vol. 127, No. 176339x, 1997.*

Robert M. Scarborough, "Chapter 8. Anticoagulant Strategies Targeting Thrombin and Factor Xa," *Annual Reports in Medicinal Chemistry*,(1995) 30, pp. 71–80.

Bastian, et al. "Preparation of [(pyrrolidinoalkoxy)phenyl]–benzothiophenes and analogs as thrombin inhibitors," *Chemical Abstracts*, vol. 127, No. 3 (1997).

Sall, et al., Dibasic benzo[b] thiophene derivatives as a novel class of active site–directed thrombin inhibitors. 1. Determination of the serine protease selectivity, structure–activity relationships, and binding orientation, *J. Med. Chem.*, vol. 40, No. 22, Oct. 24, 1997.

Jones, C., et al., *J. Med. Chem.*, 27 (8), 962–966 (1979).

Jones, C., et al., *J. Med. Chem*, 27 (8), 1057–1066 (1984).

Delgado and Remens, *Textbook of Organic Medicinal and Pharmaceutical Chemistry*, 9$^{th}$ Edition, 30–31 (1991).

Green and Wuts, *Protective Groups in Organic Syntnesis*, 2$^{nd}$ Edition, 77–79 (1991).

* cited by examiner

*Primary Examiner*—Robert W. Ramsver

(57) ABSTRACT

This application relates to novel compounds of formula (I) (and their pharmaceutically acceptable salts), as defined herein, processes and intermediates for their preparation, pharmaceutical formulations comprising the novel compounds of formula (I), and the use of the compounds of formula (I) as thrombin inhibitors.

20 Claims, No Drawings

ANTITHROMBOTIC AGENTS

This application is a 371 of PCT/US98/08830 filed Apr. 30, 1998 which claims benefit of provisional application Ser. No. 60/044,297 filed Apr. 30, 1997.

This invention relates to thrombin inhibitors which are useful anticoagulants in mammals. In particular it relates to heterocyclic derivatives having high anticoagulant activity, and antithrombotic activity. Thus, this invention relates to new inhibitors of thrombin, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin. See, for example Robert M. Scarborough, *Annual Reports in Medicinal Chemistry*, (1995), 30, 71–80.

Although the heparins and coumarins are effective anticoagulants, no commercial drug has yet emerged from the small synthetic molecules; and despite the continuing promise for this class of compounds, there still exists a need for anticoagulants which act selectively on thrombin, and which, independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent thrombin inhibitors that may have high bioavailability following oral administration.

According to the invention there is provided a method of inhibiting thrombin comprising using an effective amount of a thrombin inhibiting compound of formula I (or a pharmaceutically acceptable salt thereof)

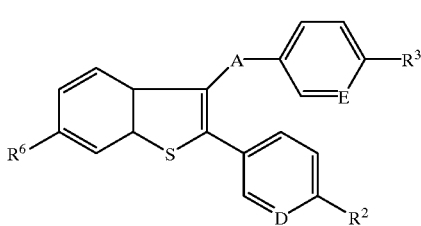

I wherein
A is carbonyl or methylene;
D is CH, $CR^d$ or N in which $R^d$ is hydroxy, methyl or methoxy;
E is CH, $CR^e$ or N in which $R^e$ is methyl, methoxy or halo;
$R^2$ is $-X^2-(CH_2)_m-NR^aR^b$ in which $X^2$ is a direct bond, methylene, O or S; m is 1, 2, 3, 4 or 5; provided that when m is 1, then $X^2$ is a direct bond; and $R^a$ and $R^b$ are independently hydrogen or (1–3C)alkyl or the group $NR^aR^b$ is pyrrolidino, piperidino, or morpholino;
$R^3$ is $-X^3-(CH_2)_n-L-R^c$, $-O-CHR^f-CHR^f-R^c$, $-O-N(R^g)_2$, $-S-R^h$ or $-CO-R^i$ in which $X^3$ is a direct bond, methylene or O; n is 1 or 2, provided that when n is 1, then $X^2$ is a direct bond; L is $-(CH_2)_k-$ in which k is 0, 1, 2 or 3, or L is $-(CHCH_3)-$; $R^c$ is cyano, cyclopentyl, 2-oxopyrrolidin-1-yl, 2,5-dioxopyrrolidin-1-yl, 2-oxooxazolidin-3-yl, 2-oxoimidazolidin-1-yl, 3-methyl-2-oxoimidazolidin-1-yl, 2-oxopyrrolidin-3-yl, 1-methyl-2-oxopyrrolidin-3-yl, 1-tetrazolyl, methoxy, methylsulfonylamino or phenylsulfonylamino; or $R^c$ is 2-methylthiazol-4-yl, $CONR^jR^k$ or $CONHNR^jR^k$ in which $R^j$ is hydrogen, methyl or ethyl and $R^k$ is hydrogen, methyl, ethyl or isopropyl; the two $R^f$ groups together form a tetramethylene diradical so that the resulting 1,2-cyclohexanediyl group is trans; $R^g$ is methyl or ethyl, $R^h$ is 2-thiazolyl; and $R^i$ is methoxy, dimethylamino or pyrrolidino; and
$R^6$ is hydrogen, hydroxy or methoxy.

A particular thrombin inhibiting compound of formula I (or a pharmaceutically acceptable salt thereof) as described above is one wherein
A is carbonyl or methylene;
D is CH, $CR^d$ or N in which $R^d$ is methyl or methoxy;
E is CH, $CR^e$ or N in which $R^e$ is methyl, methoxy or halo;
$R^2$ is $-X^2-(CH_2)_m-NR^aR^b$ in which $X^2$ is a direct bond, methylene, O or S; m is 1, 2, 3, 4 or 5; provided that when m is 1, then $X^2$ is a direct bond; and $R^a$ and $R^b$ are independently hydrogen or (1–3C)alkyl or the group $NR^aR^b$ is pyrrolidino, piperidino, or morpholino;
$R^3$ is $-X^3-(CH_2)_n-R^c$, $-O-CHR^f-CHR^f-R^c$, $-O-N(R^g)_2$, $-S-R^h$ or $-CO-R^i$ in which $X^3$ is a direct bond, methylene or O; n is 1 or 2, provided that when n is 1, then $X^2$ is a direct bond; $R^c$ is cyano, cyclopentyl, 2-oxopyrrolidin-1-yl, 2,5-dioxopyrrolidin-1-yl, 2-oxooxazolidin-3-yl, 2-oxoimidazolidin-1-yl, 3-methyl-2-oxoimidazolidin-1-yl, 2-oxopyrrolidin-3-yl, 1-methyl-2-oxopyrrolidin-3-yl, 1-tetrazolyl, methoxy, methylsulfonylamino or phenylsulfonylamino; the two $R^f$ groups together form a tetramethylene diradical so that the resulting 1,2-cyclohexanediyl group is trans; $R^g$ is methyl or ethyl, $R^h$ is 2-thiazolyl; and $R^i$ is methoxy, dimethylamino or pyrrolidino; and $R^6$ is hydrogen, hydroxy or methoxy.

A particular value for D is CH.

A particular value for E is —$CR^e$ in which $R^e$ is methyl or methoxy.

A particular value for $R^2$ is 2-(1-pyrrolidinyl)-ethoxy.

A particular value for $R^3$ is —$X^3$—$(CH_2)_n$—$R^c$ in which $R^c$ is 2-oxopyrrolidin-1-yl, and more particularly in which $R^3$ is (2-oxopyrrolidin-1-yl)methyl or 2-(2-oxopyrrolidin-1-yl)ethoxy.

A particular value for $R^6$ is hydroxy.

A more particular value for A is methylene.

A preferred method of the invention includes one wherein said compound of formula I is one of those described herein at Examples 1, 13, 22 and 23.

The present invention also provides a method of inhibiting coagulation in a mammal comprising administering to a mammal in need of treatment, a coagulation inhibiting dose of a thrombin inhibiting compound of formula I having any of the above definitions.

The present invention further provides a method of inhibiting thrombin comprising administering to a mammal in need of treatment, a thrombin inhibiting dose of a thrombin inhibiting compound of formula I having any of the above definitions.

Further, the present invention provides a method of treating a thromboembolic disorder comprising administering to a mammal in need of treatment, an effective dose of a thrombin inhibiting compound of formula I having any of the above definitions.

In addition, there is provided the use of a thrombin inhibiting compound of formula I having any of the above definitions for the manufacture of a medicament for treatment of a thromboembolic disorders.

As a further aspect of the invention, there is provided a prodrug (or a pharmaceutically acceptable salt thereof) of any of the above described thrombin inhibiting compounds of formula I which will form a prodrug. (It will be recognized that a thrombin inhibiting compound of formula I also may serve as a prodrug for a different thrombin inhibiting compound of formula I).

As an additional feature of the invention there is provided a pharmaceutical formulation comprising in association with a pharmaceutically acceptable carrier, diluent or excipient, a prodrug of a thrombin inhibiting compound of formula I (or of a pharmaceutically acceptable salt thereof) as provided in any of the above descriptions.

In general, the thrombin inhibiting compounds of formula I are believed to be novel and, thus, to constitute an additional aspect of the invention. Thus, according to the invention there is provided a novel compound of formula I (or a pharmaceutically acceptable salt thereof) according to any of the above definitions of a compound of formula I, provided that the compound is not one which is not novel.

A pharmaceutically acceptable salt of an antithrombotic compound of the instant invention includes one which is an acid-addition salt made with an acid which provides a pharmaceutically acceptable anion. Thus, an acid additon salt of a novel compound of formula I as provided above made with an acid which affords a pharmaceutically acceptable anion provides a particular aspect of the invention. Examples of such acids are provided hereinbelow.

As an additional aspect of the invention there is provided a pharmaceutical formulation comprising in association with a pharmaceutically acceptable carrier, diluent or excipient, a novel compound of formula I (or a pharmaceutically acceptable salt thereof) as provided in any of the above descriptions.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

It will be appreciated that certain compounds of formula I (or salts or prodrugs, etc.) may exist in, and be isolated in, isomeric forms, including cis- or trans-isomers, as well as optically active, racemic, or diastereomeric forms. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against thrombin, it being well known in the art how to prepare or isolate particular forms and how to determine inhibitory properties against thrombin by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

Particular values are listed below for radicals, substituents, and ranges, for illustration only, and they do not exclude other defined values or other values within defined ranges for the radicals and substituents.

A particular value for a (1–3C)alkyl group is methyl, ethyl, propyl or isopropyl.

A compound of formula I may be made by processes which include processes known in the chemical art for the production of known compounds of formula I or of structurally analogous compounds or by a novel process described herein. A process for a novel compound of formula I (or a pharmaceutically acceptable salt thereof), novel processes for a compound of formula I and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

In general, a compound of formula I may be prepared according to one of the routes outlined in Scheme I, and described in the examples, in which each of $Q^2$, $Q^3$ and $Q^6$, resectively, represents a value defined for the groups $R^2$, $R^3$ and $R^6$, a protected version of such a group, or moiety which can be further elaborated into such a group. Final conversion of a group $Q^2$, $Q^3$ or $Q^6$ into $R^2$, $R^3$ or $R^6$ is carried out at a convenient point, consistent with the chemistry employed. It will be recognized that a number of other routes may be used, particularly those involving condensation of an organometallic species to form a compound of formula C or G in Scheme I.

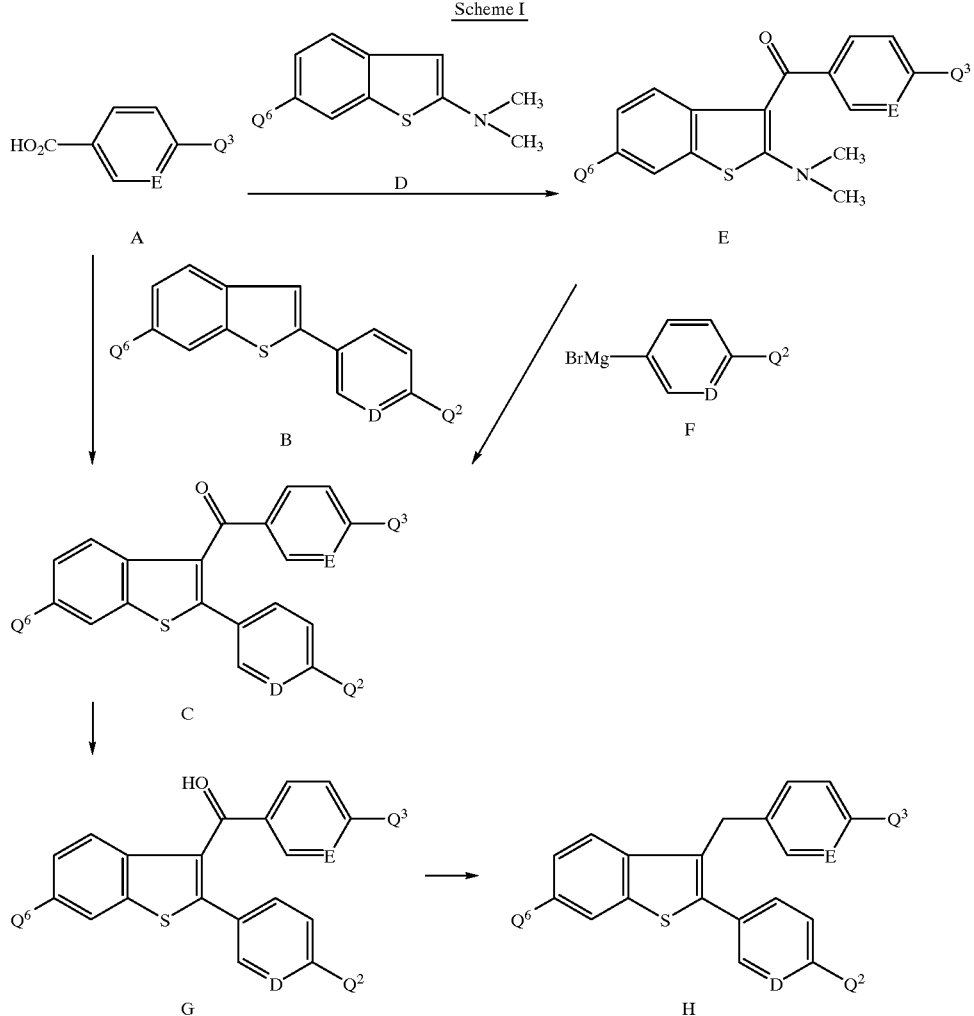

Scheme I

Thus, there is provided a process for preparing a novel compound of formula I (or a pharmaceutically acceptable salt thereof) as provided in any of the above descriptions which is selected from any of those described in the examples, including, (a) for a compound of formula I in which A is methylene, reductively removing the hydroxy group of a corresponding alcohol of formula II

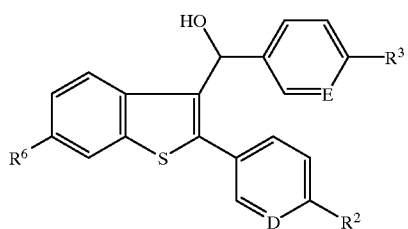

II (itself available by reducing a corresponding ketone of formula I in which A is carbonyl), for example as described in Example 23;

(b) for a compound of formula I in which $R^3$ is $CH_2R^c$ in which $R^c$ is cyano, cyclopentyl, 2-oxopyrrolidin-1-yl, 2,5-dioxopyrrolidin-1-yl, 2-oxooxazolidin-3-yl, 2-oxoimidazolidin-1-yl, 3-methyl-2-oxoimidazolidin-1-yl, 2-oxopyrrolidin-3-yl, 1-methyl-2-oxopyrrolidin-3-yl, 1-tetrazolyl or methoxy, alkylating the anion derived from a compound of formula H—$R^c$ using an alkylating agent corresponding to the compound of formula I, but in which $R^3$ is $CH_2X$ in which X is a conventional leaving group, for example as described in Example 1;

(c) for a compound of formula I in which $R^3$ is —$X^3$—$(CH_2)_n$—L—$R^c$ in which $X^3$ is O, alkylating the hydroxy group of a corresponding phenol of formula III

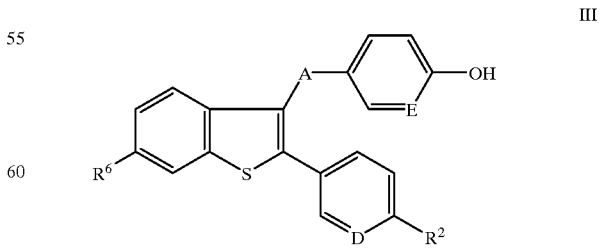

III with a group of formula X—$(CH_2)_n$—L—$R^c$, wherein X is a conventional leaving group, for example as described in Example 13; and (d) alkylating the nitrogen of a corresponding amine of formula H—NR$^a$R$^b$, using a compound corresponding to the compound of formula I, but in which R$^2$ is —X$^2$—(CH$_2$)$_m$—X in which X is a conventional leaving group, for example as described in Example 22;

whereafter, for any of the above procedures, when a functional group is protected using a protecting group, removing the protecting group;

whereafter, for any of the above procedures, when a pharmaceutically acceptable salt of a compound of formula I is required, it may be obtained by reacting the basic form of such a compound of formula I with an acid affording a physiologically acceptable counterion or by any other conventional procedure.

As used herein, a leaving group is a moiety which is displaced in a nucleophilic substitution reaction, for example a halo group (such as chloro, bromo or iodo), a sulfonate ester group (such as methylsulfonyloxy, p-toluylsulfonyloxy or trifluoromethylsulfonyloxy), or the reactive species derived from treating an alcohol with triphenylphospine, diethyl azodicarboxylate and triethyl amine (in a Mitsunobu reaction).

Novel intermediate or starting material compounds, such as an alcohol of formula II provide a further aspect of the invention. As noted above, an alcohol of formula II may be obtained by reduction of the carbonyl of a corresponding compound of formula I or by condensation of an organometallic species with the requisite aldehyde.

As mentioned above, a compound corresponding to a compound of formula I but in which a functional group is protected may serve as an intermediate for a compound of formula I. Accordingly, such protected intermediates for a novel compound of formula I provide further aspects of the invention. Thus, as one particular aspect of the invention, there is provided a compound corresponding to a novel compound of formula I as defined above in which R$^6$ which is hydroxy, but in which the corresponding substituent is —OR$^P$ in place of hydroxy, wherein R$^P$ is a phenol protecting group other than methyl. Phenol protecting groups are well known in the art, for example as described in T. W. Greene and P. G. M. Wuts, "Protecting Groups in Organic Synthesis" (1991). Particular values of R$^P$ include, for example, benzyl and allyl. Further, RP may denote a functionalized resin, for example as disclosed in H. V. Meyers, et al., *Molecular Diversity*, (1995), 1, 13–20.

As mentioned above, the invention includes pharmaceutically acceptable salts of the thrombin inhibiting compounds defined by the above formula I. A particular compound of this invention possesses one or more sufficiently basic functional groups to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

If not commercially available, the necessary starting materials for the preparation of a compound of formula I may be prepared by procedures which are selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Selective methods of protection and deprotection are well known in the art for preparation of compounds such as those corresponding to a compound of formula I but in which R$^6$ is OR$^P$, discussed above. Selective methods for cleavage of methyl ethers, as described in the examples, are discussed in Jones, et al., *J. Med. Chem.*, (1984), 27, 1057–1066. For example, the diether 3-(4-methoxybenzoyl)-2-(4-methoxyphenyl)benzo[b]thiophene may be treated with boron tribromide in dichloromethane at −10° C. (1 hour) to afford the monoether 2-(4-hydroxyphenyl)-3-(4-methoxybenzoyl)benzo[b]thiophene, whereas treatment with sodium thioethoxide affords the isomeric monoether 3-(4-hydroxybenzoyl)-2-(4-methoxyphenyl)benzo[b]thiophene. Treatment with boron tribromide under less mild conditions (0°, 6 hours) or with aluminum chloride and ethanethiol cleaves both ethers.

Generally, the compounds of the invention are isolated best in the form of acid addition salts. Salts of the compounds of formula I formed with acids such as those mentioned above are useful as pharmaceutically acceptable salts for administration of the antithrombotic agents and for preparation of formulations of these agents. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting thrombin in mammals comprising administering to a mammal in need of treatment an effective (thrombin inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in mammals comprising administering to a mammal in need of treatment an effective (coagulation inhibiting) dose of a compound of formula I.

The thrombin inhibition, coagulation inhibition and thromboembolic disorder treatment contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally, parenterally e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Another embodiment of the present invention is a pharmaceutical formulation comprising an effective amount of a novel compound of formula I or a pharmaceutically acceptable salt or solvate thereof in association with a pharmaceutically acceptable carrier, diluent or excipient therefor.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

|  |  |
| --- | --- |
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

|  |  |
| --- | --- |
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

|  |  |
| --- | --- |
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 ml dose, are made as follows:

|  |  |
| --- | --- |
| Active ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| Active ingredient | 100 mg |
|---|---|
| Isotonic saline | 1,000 mL |

The solution of the above ingredients generally is administered intravenously to a subject at a rate of 1 mL per minute.

The ability of the compounds of the present invention to be an effective and orally active thrombin inhibitor are evaluated in one or more of the following assays.

The compounds provided by the invention (formula I) selectively inhibit the action of thrombin in mammals. The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide, N-benzoyl-L-Phe-L-Val-L-Arg-p-nitroanilide.

The assay is carried out by mixing 50 µL buffer (0.03M Tris, 0.15M NaCl, pH 7.4) with 25 µL of human thrombin solution (purified human thrombin, Enzyme Research Laboratories, South Bend, Ind., at 8 NIH units/mL) and 25 µL of test compound in a solvent (50% aqueous methanol (v:v)). Then 150 µL of an aqueous solution of the chromogenic substate (at 0.25 mg/mL) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

Thrombin + I ⇌ Thrombin − I

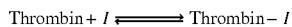

$$Kass = \frac{[Thrombin - I]}{[(Thrombin) \times (I)]}$$

Kass is calculated for a range of concentrations of test compounds and the mean value reported in units of liter per mole. In general, a thrombin inhibiting compound of formula I of the instant invention exhibits a Kass of $0.05 \times 10^6$ L/mole or much greater.

By substantially following the procedures described above for human thrombin, and using other human blood coagulation system serine proteases and using fibrinolytic system serine proteases, with the appropriate chromogenic substrates, identified below, the selectivity of the compounds of the present invention with respect to the coagulation factor serine proteases and to the fibronolytic serine proteases are evaluated as well as their substantial lack of interference with human plasma clot fibrinolysis.

Human factors X, Xa, IXa, XIa, and XIIa are purchased from Enzyme Research Laboratories, South Bend, Indiana; human urokinase from Leo Pharmaceuticals, Denmark; and recombinant activated Protein C (aPC) is prepared at Eli Lilly and Co. substantially according to U.S. Pat. No. 4,981,952. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from Kabi Vitrum, Stockholm, Sweden, or from Midwest Biotech, Fishers, Indiana. Bovine trypsin is purchased from Worthington Biochemicals, Freehold, New Jersey, and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants, or purchased from Midwest Biotech, Fishers, Ind.

Human plasmin is purchased from Boehringer Mannheim, Indianapolis, Ind.; nt-PA is purchased as single chain activity reference from American Diagnostica, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Thrombin inhibitors preferably should spare fibrinolysis induced by urokinase, tissue plasminogen activator (t-PA) and steptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agents. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 μL thrombin (73 NIH unit/mL) to 100 μL human plasma which contains 0.0229 μci 125-iodine labeled fibrinogen. Clot lysis is studied by overlaying the clots with 50 μL of urokinase or streptokinase (50, 100, or 1000 unit/mL) and incubating for 20 hours at room temperature. After incubation the tubes are centrifuged in a Beckman Microfuge. 25 μL of supernate is added into 1.0 mL volume of 0.03 M tris/0.15 M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 μg/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, Biochem. J., 185, 1–11 (1980); and Smith, et al., Biochemistry, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., Thrombosis Research, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous shunt model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, Br J Pharmacol, 77:29, 1982). In this model preferred compounds of the instant invention reduce the net clot weight to approximately 25–30% of control, or even lower, at an i.v. dose of 33.176 μmol/kg/h.

$FeCl_3$ model of arterial injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 μL is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, Thromb. Res., 60:269, 1990).

Spontaneous thrombolysis model

In vitro data suggests that thrombin inhibitors inhibit thrombin and, at higher concentrations, may inhibit other serine proteases, such as plasmin and tissue plasminogen activator. To assess if the compounds inhibit fibrinolysis in vivo, the rate of spontaneous thrombolysis is determined by implanting a labeled whole blood clot into the pulmonary circulation. Rat blood (1 mL) is mixed rapidly with bovine thrombin (4 IU, Parke Davis) and 125I human Fibrogen (5 μCi, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected cpm} - \text{lung cpm})}{\text{injected cpm}} \times 100$$

The fibrinolytic dissolution of the implanted clot occurs time-dependently (see J. P. Clozel, Cardiovas. Pharmacol., 12:520, 1988).

Coagulation parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and $CaCl_2$ (0.1 mL, 0.025 M) is added to start coagulation. Assays are done in duplicate and averaged.

Index of Bioavailability

For a measure of bioactivity, plasma thrombin time (TT) serves as a substitute for the assay of parent compound on the assumption that observed increments in TT resulted from thrombin inhibition by parent only. The time course of the effect of the thrombin inhibitor upon TT is determined after i.v bolus administration to anesthetized rats and after oral treatment of fasted conscious rats. Due to limitations of blood volume and the number of points required to determine the time course from time of treatment to the time when the response returns to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{AUC\,po}{AUC\,iv} \times \frac{Dose\,iv}{Dose\,po} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means +/− SEM. One-way analysis of variance is used to detect statistically significant differences and then Dunnett's test is applied to determine which means are different. Significance level for rejection of the null hypothesis of equal means is P<0.05.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum . The room temperature is maintained between 66–74° F.; 45–50 percent relative humidity; and lighted from 0600–1800 hours.

Pharmacokinetic model.

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation,* 82, 930–940 (1990). Mixed-breed hounds (aged 6–7 months, either sex, Hazelton-LRE, Kalamazoo, Mich., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-$\mu$A direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for at least 30 minutes.

Hematology and template bleeding time determinations

Whole blood cell counts, hemoglobin, and hematocrit values are determined on a 40-$\mu$L sample of citrated (3.8 percent) blood (1 part citrate: 9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean ±SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples are provided to further describe the invention and are not to be construed as limitations thereof. Unless otherwise described, procedures generally were conducted at room temperature. Although not provided in all cases, satisfactory $^1$H-NMR data were generally obtained for the Examples.

The abbreviations, symbols and terms used in the examples have the following meanings.

Ac=acetyl
AIBN=azobisisobutyronitrile
Anal.=elemental analysis
Bn or Bzl=benzyl
Bu=butyl
n-BuLi=butyllithium
calcd=calculated
DCC=dicyclohexylcarbodiimide
DIBAL-H=diisobutyl aluminum hydride
DMF=dimethylformamide
DMSO=dimethylsulfoxide
Et=ethyl
EtOAc=ethyl acetate
Et$_3$N=triethylamine
Et$_2$O=diethyl ether
EtOH=ethanol
EtSH=ethanethiol
FAB=Fast Atom Bombardment (Mass Spectrascopy)
FDMS=field desorption mass spectrum
Hex=hexanes
HOAt=1-hydroxy-7-azabenzotriazole
HPLC=High Performance Liquid Chromatography
HRMS=high resolution mass spectrum
ISMS=ion spray mass spectrum
i-PrOH=isopropanol
IR=Infrared Spectrum
LAH=lithium aluminum hydride
Me=methyl
MeI=methyl iodide
MeOH=methanol
MPLC=Medium Pressure Liquid Chromatography
NBS=N-bromosuccinimide
NMR=Nuclear Magnetic Resonance
Ph=phenyl
PPA=polyphosphoric acid
i-Pr=isopropyl
Rochelle's Salt=potassium sodium tartrate
RPHPLC=Reversed Phase High Performance Liquid Chromatography
SiO$_2$=silica gel
SM=starting material
TBS=tert-butyldimethylsilyl
TEA=triethylamine
Temp.=temperature
TFA=trifluoroacetic acid
THF=tetrahydrofuran
TIPS=triisopropylsilyl
TLC=thin layer chromatography
triflic acid=trifluoromethanesulfonic acid Unless otherwise stated, pH adjustments and work up are with aqueous acid or base solutions. PrepLC indicates preparative liquid chromatography using "Prep Pak (TM)" silica cartridges; radial chromatography indicates preparative chromatography using a "Chromatotron (TM)" instrument.

EXAMPLE 1

Preparation of 6-Hydroxy-3-[3-methyl-4-[(2-oxopyrrolidin-1-yl)methyl]benzyl]-2-[4-[2-(1-pyrrolidinyl)ethoxy]phenyl]-benzo[b]thiophene Oxalate.

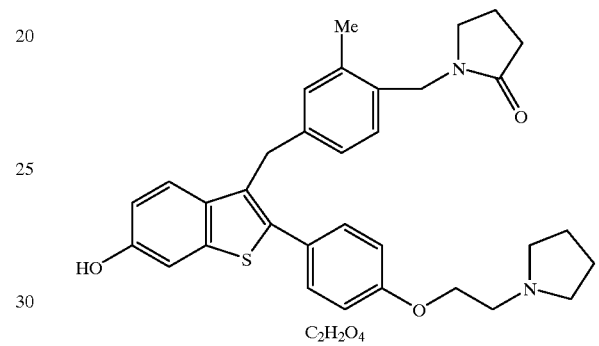

A. 6-Benzyloxy-2-(dimethylamino)benzo[b]thiophen-3-yl 4-Bromo-3-(methyl)phenyl Ketone.

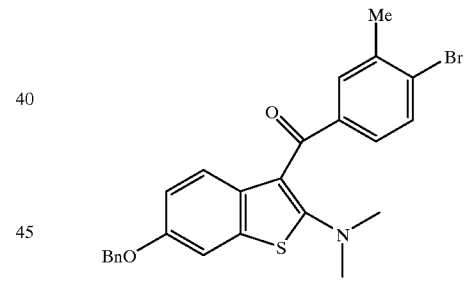

Oxalyl chloride (15.8 mL, 181 mmol) was added to a stirred suspension of 4-bromo-3-methylbenzoic acid (6.00 g, 27.9 mmol) in anhydrous CH$_2$Cl$_2$ (40 mL), followed by the addition of 2 drops of DMF. The suspension was stirred at room temperature under nitrogen atmosphere for 6 h, then it was concentrated to dryness.

To the crude benzoyl chloride suspended in anhydrous chlorobenzene (50 mL) was added 6-benzyloxy-2-(dimethyl-amino)benzo[b]thiophene (6.33 g, 22.3 mmol). The resultant mixture was heated in an oil bath at 110° C. for 2 h. At room temperature, the mixture was diluted with EtOAc (160 mL) before it was cautiously treated with saturated NaHCO$_3$ (50 mL). The organic layer was dried over MgSO$_4$, filtered, concentrated, and chromatographed on silica [gradient 0–5% EtOAc in toluene] to give 7.49 g (70%) of the amino-ketone as a foam.

IR (neat) 3450, 1623, 1598 cm$^{-1}$; FDMS m/e 479 (M$^+$, $^{79}$Br) and 481 (M+, $^{81}$Br); Anal. Calcd. for C$_{25}$H$_{22}$BrNO$_2$S: C, 62.50; H, 4.62; N, 2.92. Found: C, 62.77; H, 4.59; N, 2.87.

B. 6-Benzyloxy-2-[4-[2-(1-pyrrolidinyl)ethoxy]phenyl]-benzo[b]thiophen-3-yl 4-Bromo-3-(methyl)phenyl Ketone.

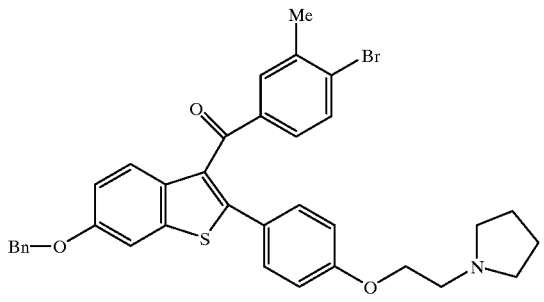

1-[2-(4-Bromophenoxy)ethyl]pyrrolidine (3.87 g, 14.3 mmol) was added to a stirred suspension of magnesium ribbons (307 mg, 12.6 mmol) in anhydrous THF (6 mL) under an argon atmosphere, followed by the addition of a small iodine chip. The resultant mixture was heated in an oil bath at 60–65° C. for 1 h to form a homogeneous Grignard solution. The Grignard solution was cooled to room temperature and diluted with anhydrous THF (10 mL) before it was added to a stirred solution of the above amino-ketone (4.05 g, 8.42 mmol) in anhydrous THF (15 mL) at 0° C. under an argon atmosphere. The resultant mixture was stirred at 0° C. for 2 h, then quenched with saturated aqueous $NH_4Cl$ (20 mL). After extraction with EtOAc (70 mL×2), the combined organic layers were dried over $MgSO_4$, filtered, concentrated and chromatographed on silica [gradient 0–5% $Et_3N$ 50–45% hexanes in toluene] to give 5.28 g (100%) of the ketone as a yellow oil.

IR (neat) 2953, 1646, 1607 cm$^{-1}$; FDMS m/e 625 (M$^+$, $^{79}$Br) and 627 (M+, $^{81}$Br).

C. 6-Benzyloxy-2-[4-[2-(1-pyrrolidinyl)ethoxy]phenyl]-benzo[b]thiophen-3-yl 4-(Methoxycarbonyl)-3-(methyl) phenyl Ketone.

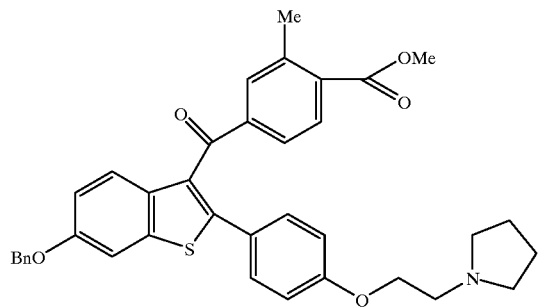

To a stirred solution of the above ketone (5.10 g, 8.14 mmol) in 25 mL anhydrous DMF were sequentially added Pd (OAc)$_2$ solid (190 mg, 0.846 mmol), 1,3-bis (diphenylphosphino)propane solid (349 mg, 0.846 mmol), 12.5 mL Et$_3$N, and 12.5 mL MeOH. The reaction was purged with CO (g) and kept under a balloon CO (g) atmosphere while heating the resulting mixture at 70° C. for 8 h. The mixture was allowed to cool to room temperature, then it was diluted with 100 ml H$_2$O and 200 ml EtOAc. The aqueous layer was extracted with EtOAc (2×100 mL), then the combined organics were dried over MgSO$_4$, filtered, concentrated, and chromatographed [gradient 0–5% EtOH/ Et$_3$N (2/1) 5–25% THF in hexanes] to give 3.26 g (64%) of the keto-ester as a yellow oil.

IR (neat) 2945 (br), 1724, 1647, 1606 cm$^{-1}$; FDMS m/e 606 (M$^+$+1).

D. 6-Benzyloxy-3-[4-(hydroxymethyl)-3-(methyl)benzyl]-2-[4-[2-(1-pyrrolidinyl) ethoxy]phenyl]benzo[b]thiophene.

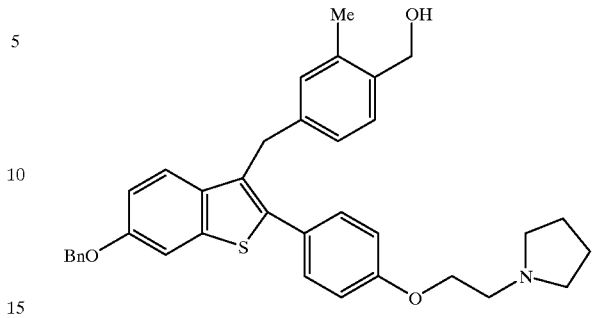

DIBAL-H (18.84 mL, 1 M in toluene) was added to a stirred solution of the above keto-ester (3.26 g, 5.38 mmol) in anhydrous CH$_2$Cl$_2$ (25 mL) at 0° C. under a nitrogen atmosphere. The resultant solution was stirred at 0° C. for 1.5 h. The reaction mixture was treated sequentially with MeOH (1.0 mL), diluted with EtOAc (75 mL), and saturated aqueous Rochelle's salt solution (75 mL). The two-layered solution was stirred vigorously at room temperature for 1 h. After extraction with EtOAc (2×50 mL), the organic layer was dried over MgSO$_4$, filtered, and concentrated to yield the corresponding diol.

The above diol was dissolved in anhydrous CH$_2$Cl$_2$ (25 mL) and cooled to 0° C. before it was sequentially treated with TFA (5.01 mL, 65.1 mmol) and Et$_3$SiH (6.06 mL, 37.9 mmol). The resultant mixture was stirred at 0° C. for 1 h. After cautious treatment with saturated aqueous NaHCO$_3$ to neutralize TFA, the mixture was allowed to warm to room temperature where it was extracted with EtOAc (3×50 mL). The combined organic layers were dried over MgSO$_4$, filtered, concentrated, and chromatographed on silica [gradient 0–5% Et$_3$N 50–70%EtOAc in hexanes; then 10% EtOH/Et$_3$N (1/1) 70% EtOAc in hexanes] to give 2.29 g (75%) of the alcohol as an off-white foam.

IR (neat) 3470 (br), 1607 cm$^{-1}$; FDMS m/e 564 (M$^+$+1); Anal. Calcd. for C$_{36}$H$_{37}$NO$_3$S: C, 76.70; H, 6.62; N, 2.48. Found: C, 76.58; H, 6.45; N, 2.46.

E. 6-Benzyloxy-3-[3-methyl-4-[(2-oxopyrrolidinl-yl)-methyl]benzyl]-2-[4-[2-(1-pyrrolidinyl)ethoxy]phenyl]-benzo[b] thiophene.

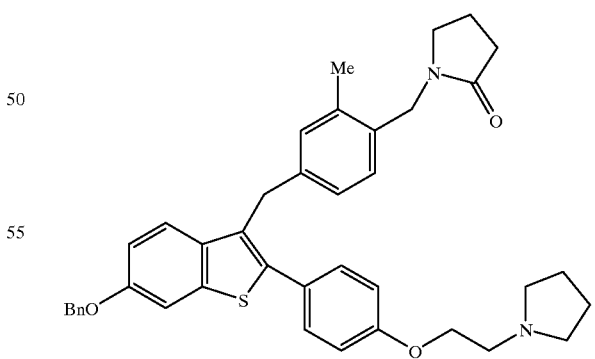

To a stirred solution of the above alcohol in THF (2.5 mL), at 0° C., under a nitrogen atmosphere was added BuLi (0.26 mL, 1.6 M in hexanes). The resulting mixture was allowed to stir for 15 min, then methanesulfonyl chloride (0.033 mL, 0.421 mmol) was added dropwise at 0° C. and stirred for 1.5 h. To the resulting mesylate was added the sodium salt of 2-pyrrolidone as a suspension in 2 mL THF plus 2 mL THF used to wash the vessel containing the 2-pyrrolidone anion. [The anion was prepared by stirring a suspension of NaH (47 mg, 60% by weight oil dispersion) in 2 mL THF, at 0° C., under a nitrogen atmosphere and adding 2-pyrrolidone (0.087 mL, 1.15 mmol).] After 45 min at 0° C., the resulting mixture was allowed to stir at an ambient temperature for 17 h. The mixture was quenched with 10 mL H$_2$O and diluted with 20 mL EtOAc. The resulting solution was extracted with EtOAc (3×20 mL), dried over MgSO$_4$, filtered, concentrated, and chromatographed on silica [gradient 0–10% EtOH/Et$_3$N (2/1) 30–40% THF in hexanes] to give 150 mg of the benzyloxy-lactam (62%) as a foam.

$^1$H NMR (CDCl$_3$) δ 1.82–1.85 (m, 4H), 1.94–2.04 (m, 2H), 2.24 (s, 3H), 2.45 (t, J=8.1 Hz, 2H), 2.65 (br s, 4H), 2.93 (t, J=6.0 Hz, 2H), 3.21 (t, J=7.1 Hz, 2H), 4.15 (t, J=6.0 z, 2H), 4.18 (s, 2H), 4.43 (s, 2H), 5.13 (s, 2H), 6.91–7.02 (m, 7H) 7.32–7.48 (m, 8H).

F. 6-Hydroxy-3-[3-methyl-4-[(2-oxopyrrolidin-1-yl)methyl]-benzyl]-2-[4-[2-(1-pyrrolidinyl)ethoxy]phenyl]-benzo[b]thiophene Oxalate.

To a stirred solution of the above benzyloxy-lactam (192 mg, 0.304 mmol) in THF (6 mL) under a nitrogen atmosphere were sequentially added 10% Pd/C (192 mg) and 25% aqueous HCO$_2$NH$_4$ (0.50 mL). The resultant mixture was stirred under a balloon nitrogen atmosphere for 16 h. After filtration, the filtrate was diluted with EtOAc (25 mL), washed with half-saturated NaCl (10 mL), dried over MgSO$_4$, filtered, concentrated, and chromatographed on silica [gradient 0–10% EtOH/Et$_3$N (2/1) in hexanes] to give 125 mg (76%) of the hydroxy-lactam as a yellow oil.

A solution of oxalic acid (26.2 mg, 0.291 mmol) in EtOAc (4 mL) was added dropwise to a stirred solution of the hydroxy-lactam (105 mg, 0.194 mmol) in EtOAc (2 mL). The resultant white suspension was filtered and the white solid was dried at 60° C. under vacuum to provide 105 mg (86%) of the salt of the hydroxy-lactam as an off-white solid.

IR (KBr) 3450 (br), 3300–2200 (br), 1653, 1609 cm$^{-1}$; FDMS m/e 541 (M$^+$+1-[C$_2$H$_2$O$_4$]).

The 6-benzyloxy-2-(dimethylamino)benzo[b]thiophene was prepared in a manner similar to the following.

G. α-(4-Benzyloxyphenyl)-α-hydroxy-N,N-dimethyl-thioacetamide.

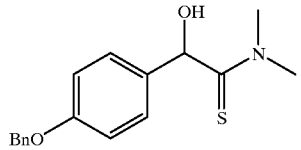

To a solution of distilled diisopropylamine (22.9 mL, 175 mmol) in 400 mL of anhydrous THF at −78° C. was added 1.6 n-butyllithium in hexanes (100 mL, 160 mmol) over a period of 45 min. The mixture was stirred at −78° C. for 1.5 h. To the solution was cannulated over a period of 1 h a solution of 4-benzyloxybenzaldehyde (30.9 g, 146 mmol) and N,N-dimethylthioformamide (13.7 mL, 160 mmol) in 100 mL of distilled THF. The reaction mixture was stirred at −78° C. for 16 h. The reaction was then quenched with 500 mL of saturated NH$_4$Cl solution. The mixture was extracted with EtOAc (3×1 L), and the combined organic layers were dried over MgSO$_4$ and concentrated under reduced pressure. The residue was then recrystallyzed from EtOAc/hexanes to afford 20.0 g (66.5 mmol, 46%) of an off-white solid.

mp 104–107° C.; FDMS 301 (M+); Anal. Calcd for C$_{17}$H$_{19}$NO$_2$S: C, 67.75; H, 6.35; N, 4.65. Found: C, 67.61; H, 6.37; N, 4.57.

H. 6-Benzyloxy-2-(dimethylamino)benzo[b]thiophene.

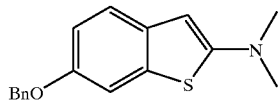

To a solution of the above thioacetamide (500 mg, 1.66 mmol) in 65 mL of dry dichloroethane at room temperature was added dropwise methanesulfonic acid (0.54 ml, 8.3 mmol). The red reaction mixture was stirred for 1.5 h and then poured into 10 mL of saturated aqueous NaHCO$_3$ solution, followed by addition of 3 mL of H$_2$O, and stirred vigorously. The layers were separated and the organic layer was dried over MgSO$_4$ and concentrated under reduced pressure. The residue was then purified by flash chromatography (silica gel, 10% Et$_2$O/hexanes) to afford 327 mg (1.15 mmol, 70%) of a white solid.

mp 78–81° C.; FDMS 283 (M+); Anal. Calcd for C$_{17}$H$_{17}$NOS: C, 72.05; H, 6.05; N, 4.94. Found: C, 72.22; H, 6.15; N, 4.89.

EXAMPLE 2

Preparation of 6-Hydroxy-3-[4-[(methylsulfonylamino)-methyl]-3-methylbenzyl]-2-[4-[2-(1-pyrrolidinyl)ethoxy]-phenyl]benzo[b]thiophene Oxalate.

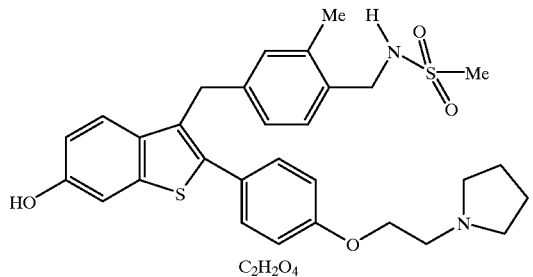

A. 6-Benzyloxy-3-[3-methyl-4-[(1-phthalimidyl)methyl]-benzyl]-2-[4-[2-(1-pyrrolidinyl)ethoxy]phenyl]-benzo[b]thiophene.

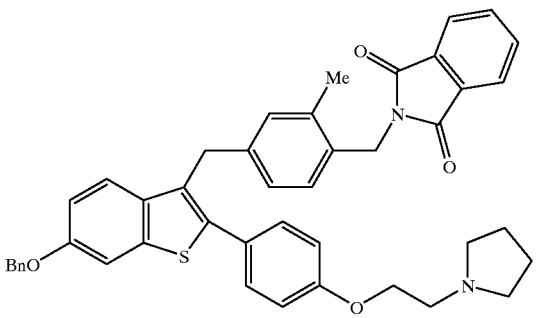

Anhydrous triethylamine (0.142 mL, 1.60 mmol) and methanesulfonyl chloride (0.124 mL, 1.60 mmol) were sequentially added to a stirred solution of the alcohol of Example 1-D (602 mg, 1.07 mmol) in anhydrous dichloromethane (5 mL) at 0° C., under a nitrogen atmosphere. The mixture was stirred for 1 h at 0° C. before it was treated with the phthalimide sodium salt [prepared from a suspension NaH (235 mg, 60% by weight) in 2 ml DMF, to which was added phthalimide (786 mg, 5.345 mmol) at 0° C.] and lithium iodide (215 mg, 1.60 mmol). The cold bath was removed and the resultant mixture was stirred for an additional 4 h. After dilution with EtOAc (40 mL), the mixture was washed with saturated NaHCO$_3$ (20 mL), dried, filtered, concentrated, and chromatographed on silica [100% THF, then gradient 0–3% Et$_3$N in THF] to give a 195 mg (26%) of the phthalimide as a yellow foam.

IR (thin film) 2944, 1769, 1716, 1605 cm$^{-1}$; FDMS m/e 692 (M$^+$).

B. 3-[4-(Aminomethyl)-3-methylbenzyl]-6-benzyloxy-2-[4-[2-(1-pyrrolidinyl)ethoxy]phenyl]benzo[b]thiophene.

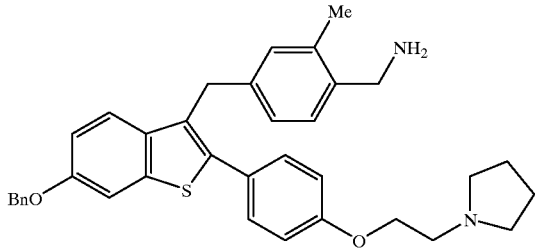

To the above phthalimide dissolved in EtOH (1 mL) was added hydrazine (0.077 mL, 85% in H$_2$O ) and H$_2$O (0.014 mL). The resultant mixture was heated to 60° C. for 1 h. The reaction mixture was then concentrated, taken back up in EtOAc (25 mL), washed with saturated NaHCO$_3$ (10 mL), dried over MgSO$_4$, filtered, concentrated, and chromatographed on silica [gradient 0–6% Et$_3$N in EtOAc] to give 136 mg (98%) of the primary amine as a yellow foam.

IR (thin film) 2967, 1608 cm$^{-1}$; FDMS m/e 563 (M$^+$+1).

C. 6-Benzyloxy-3-[4-[(methylsulfonylamino)methyl]-3-methylbenzyl]-2-[4-[2-(1-pyrrolidinyl)ethoxy]phenyl]-benzo[b]thiophene.

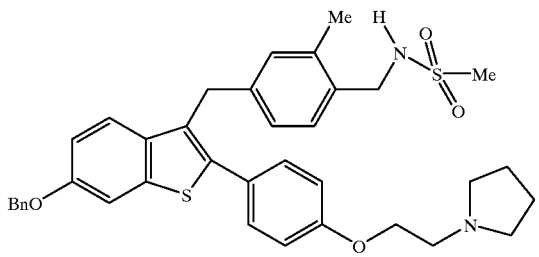

Anhydrous triethylamine (0.032 mL, 0.362 mmol) and methanesulfonyl chloride (0.021 mL, 0.265 mmol) were sequentially added to a stirred solution of the above primary amine (136 mg, 0.241 mmol) in anhydrous dichloromethane (1 mL) at 0° C., under a nitrogen atmosphere. The mixture was stirred for 30 min at 0° C., then diluted with EtOAc (10 mL). The resulting mixture was washed with saturated NaHCO$_3$ (5 mL), extracted with EtOAc (2×20 mL), dried over MgSO$_4$, filtered, concentrated, and chromatographed on silica [gradient 0–5% EtOH/Et$_3$N (2/1) in EtOAc] to give 116 mg (73%) of the benzyloxy-sulfonamide as a yellow foam.

IR (thin film) 3282, 2970, 1737, 1608 cm$^{-1}$; FDMS m/e 641 (M$^+$+1).

D. 6-Hydroxy-3-[4-[(methylsulfonylamino)methyl]-3-methyl-benzyl]-2-[4-[2-(1-pyrrolidinyl)ethoxy]phenyl]-benzo[b]thiophene oxalate.

Following the procedure described in Example 1-F, the hydroxy-sulfonamide was obtained from the above benzyloxy-sulfonamide as a yellow solid in an overall 49% yield.

IR (KBr) 3450 (br), 3300–2200 (br), 1720, 1609 cm$^{-1}$; Anal. Calcd. for C$_{30}$H$_{34}$N$_2$O$_4$S$_2$.C$_2$H$_2$O$_4$: C, 59.98; H, 5.66; N, 4.37. Found: C, 60.00; H, 5.78; N, 4.59.

EXAMPLE 3

Preparation of 3-[4-(Methoxycarbonyl)-3-methylbenzyl]-2-[4-[2-(1-pyrrolidinyl)ethoxy]phenyl]benzo[b]thiophene Oxalate.

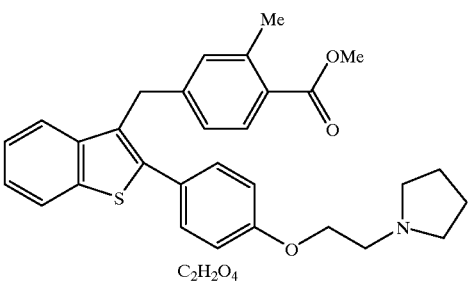

A. 4-Bromo-3-(methyl)phenyl 2-[4-[2-(1-Pyrrolidinyl)-ethoxy]phenyl]benzo[b]thiophen-3-yl Ketone.

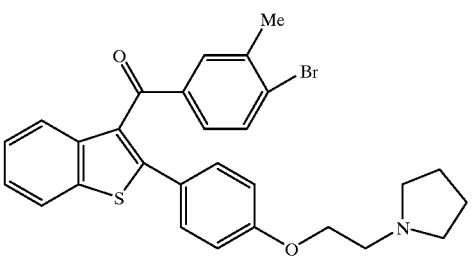

Oxalyl chloride (5.01 mL, 57.9 mmol) was added to a stirred suspension of 4-bromo-3-methylbenzoic acid (1.24 g, 5.75 mmol) in anhydrous CH$_2$Cl$_2$ (6 mL), followed by the addition of 2 drops of DMF. The suspension was stirred at room temperature under nitrogen atmosphere for 6 h, then it was concentrated to dryness under vacuum.

To the crude benzoyl chloride suspended in anhydrous CH$_2$Cl$_2$ (10 mL) was added 2-[4-[2-(1-pyrrolidinyl)ethoxy]-phenyl]benzo[b]thiophene [obtained by coupling benzo[b] thiophene-2-boric acid and 4-[2-(1-pyrrolidinyl)-ethoxy]-1-bromobenzene using a procedure similar to that of Example 17, Part G] (1.86 g, 5.75 mmol), followed by the addition of TiCl$_4$ (2.52 mL, 23.0 mmol). The mixture was stirred at 37° C. for 4 h. Then the mixture was cooled to 0 ° C. before it was treated sequentially with THF (25 mL) and 2.5 N LiOH (45 mL) in small portions. The two-layered solution was stirred vigorously for 20 min. The organic layer was separated and the aqueous layer was extracted with EtOAc (25 mL×2). The combined organic layers were washed with brine (15 mL), dried over MgSO$_4$, filtered, concentrated, and chromatographed on silica (gradient 0–8% NEt$_3$ in EtOAc) to give a 2.02 g (67%) of the ketone as a foam.

IR (neat) 1653, 1606 cm$^{-1}$; FDMS m/e 519 (M$^+$, $^{79}$Br), 521 (M$^+$, $^{81}$Br).

B. 3-(4-Bromo-3-methylbenzyl)-2-[4-[2-(1-pyrrolidinyl)-ethoxy]phenyl]benzo[b]thiophene.

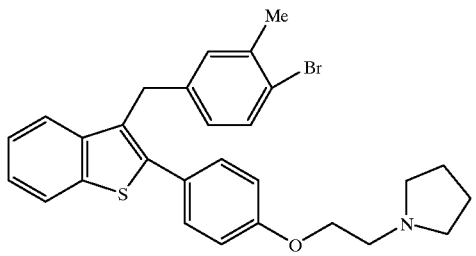

DIBAL-H (3.17 mL, 1 M in toluene) was added to a stirred solution of the above ketone (1.10 g, 2.11 mmol) in anhydrous CH$_2$Cl$_2$ (6 mL) at 0° C. under nitrogen atmosphere, and the resultant solution was stirred at 0° C. for 50 min. The reaction mixture was treated sequentially with MeOH (0.5 mL) and saturated aqueous Rochelle's salt solution (20 mL), and the two-layered solution was stirred vigorously at room temperature for 0.5 h. After extraction with EtOAc (80 mL), the organic layer was dried over MgSO$_4$, filtered, and concentrated to yield the benzyl alcohol.

The above alcohol was dissolved in anhydrous CH$_2$Cl$_2$ (7 mL) and cooled down to 0° C. before it was sequentially treated with Et$_3$SiH (2.35 mL, 14.7 mmol) and TFA (1.63 mL, 21.1 mmol). The resultant mixture was stirred at 0° C. for 1 h. After cautious treatment with saturated aqueous NaHCO$_3$ (30 mL), the mixture was extracted with EtOAc (30 mL×2). The combined organic layers were dried over MgSO$_4$, filtered, concentrated, and chromatographed on silica (gradient 0–12% Et$_3$N in EtOAc) to give a 1.01 g (95%) of the benzyl-bromide as a foam.

IR (neat) 1608 cm$^{-1}$; FDMS m/e 505 (M$^+$, $^{79}$Br), 507 (M$^+$, $^{81}$Br).

C. 3-[4-(Methoxycarbonyl)-3-methylbenzyl]-2-[4-[2-(1-pyrrolidinyl)ethoxy]phenyl]benzo[b]thiophene

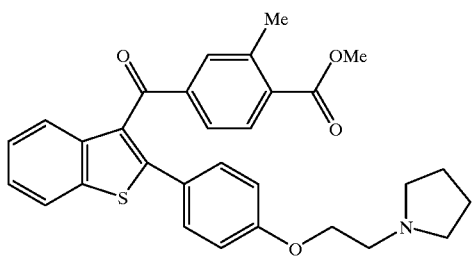

A stirred mixture of the above aryl bromide (1.06 g, 2.10 mmol), palladium acetate (47.1 mg, 0.210 mmol), 1,3-bis(diphenylphosphino)propane (86.6 mg, 0.210 mmol), dry methanol (3 mL), and dry triethylamine (3 mL) was heated in an oil bath at 60° C. under CO atmosphere for 24 h. At room temperature, the mixture was diluted with EtOAc (80 mL), washed with water (20 mL×2), dried over MgSO$_4$, filtered, concentrated, and chromatographed on silica [gradient 0–2% Et$_3$N in THF/hexanes (1/1)] to give a 480 mg (44%) of the ester as a foam.

IR (neat) 1720, 1608 cm$^{-1}$; FDMS m/e 485 (M$^+$).

D. 3-[4-(Methoxycarbonyl)-3-methylbenzyl]-2-[4-[2-(1-pyrrolidinyl)ethoxy]phenyl]benzo[b]thiophene Oxalate.

A solution of oxalic acid (7.2 mg, 0.080 mmol) in EtOAc (2 mL) was added dropwise to a stirred solution of the above ester (39 mg, 0.080 mmol) in CH$_2$Cl$_2$ (2 mL). Then the resultant solution was treated with small portions of Et$_2$O to form a white suspension. After filtration and drying at 60° C. under vacuum, a 20 mg (43%) of the oxalate salt was obtained as a white solid.

IR (KBr) 3400–2500 (br), 1718, 1608 cm$^{-1}$; FDMS m/e 485 (M$^+$-C$_2$H$_2$O$_4$).

EXAMPLE 4

Preparation of 3-[4-(Pyrrolidinocarbonyl)-3-methylbenzyl]-2-[4-[2-(1-pyrrolidinyl)ethoxy]phenyl]benzo[b]thiophene Oxalate.

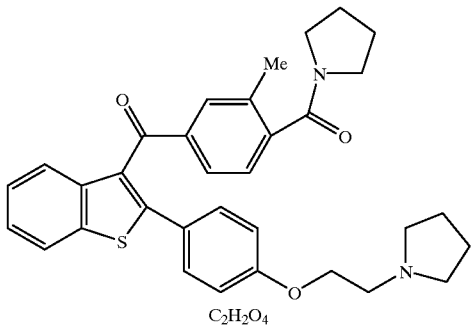

A stirred solution of the ester of Example 3-C (125 mg, 0.257 mmol) in pyrrolidine (5 mL) was heated to reflux for 3 days. After concentration and subsequent chromatography on silica [gradient 3–20% Et$_3$N in THF/hexane (1/1)], 100 mg (74%) of the amide was obtained as a gum.

A solution of oxalic acid (16.0 mg, 0.178 mmol) in EtOAc (2 mL) was added dropwise to a stirred solution of the amide (90.0 mg, 0.172 mmol) in EtOAc (3 mL). The resultant suspension was treated with small portions of ether (10 mL). After filtration and drying at 50° C. under vacuum, 88 mg (83%) of the oxalate salt of the amide was obtained as a white solid.

IR (KBr) 3400–2500 (br), 1723, 1623, 1608 cm$^{-1}$; FDMS m/e 525 (M$^+$+1-C$_2$H$_2$O$_4$).

EXAMPLE 5

Preparation of 3-Chloro-4-(dimethylaminooxy)phenyl 2-[4-[2-(1-pyrrolidinyl)ethoxy]phenyl]benzo[b]thio-phen-3-yl Ketone oxalate.

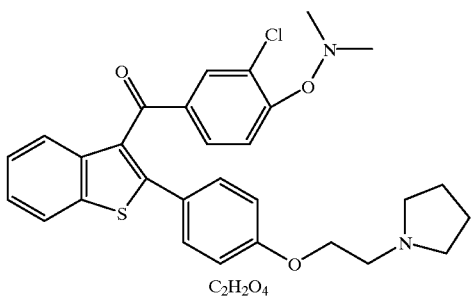

A. 3-Chloro-4-fluorophenyl 2-[4-[2-(1-Pyrrolidinyl)-ethoxy]phenyl]benzo[b]thiophen-3-yl Ketone.

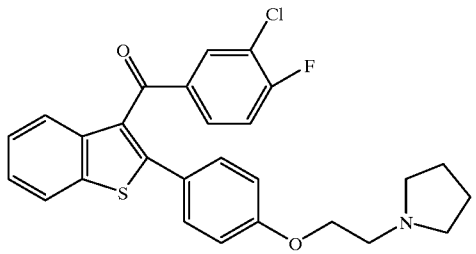

Oxalyl chloride (12.49 mL, 143 mmol) was added to a stirred suspension of 3-chloro-4-fluorobenzoic acid (5.00 gi 28.6 mmol) in anhydrous dichloromethane (30 mL), followed by the addition of 2 drops of DMF. The suspension was stirred at room temperature under nitrogen atmosphere for 14 h, then it was concentrated to dryness under vacuum at 50° C.

To 2-[4-[2-(1-pyrrolidinyl)ethoxy]phenyl]benzo[b]-thiophene in anhydrous 1,2-dichloroethane (40 mL) was added a solution of the crude benzoyl chloride in anhydrous 1,2-dichloroethane (10 mL). The mixture was cooled to −20° C., treated with $TiCl_4$ (7.87 mL, 71.6 mmol), which caused the mixture to form a precipitate. The resulting wet solid was sonicated in a water bath at room temperature to help the reactants to become soluble. The reaction mixture was placed in a ice bath and allowed to stir for 1.5 h, then at room temperature for 1 h. The reaction mixture was placed in an ice bath and THF (50 mL) was slowly added followed by the addition of 5N NaOH (60 mL). The solids were filtered off and and washed with EtOAc (50 mL), then the aqueous layer was extracted with EtOAc (3×50 mL). The organic layer was separated and the aqueous layer was extracted with EtOAc (60 mL×2). The combined organic layers were dried over $MgSO_4$, filtered, concentrated, and chromatographed on silica [gradient 0–2% $Et_3N$ 18% hexanes in EtOAc] to give 8.21 g (60%) of mostly the named ketone and the isomer substituted at the six position. After recrystallization from EtOAc 4.5 g (33%) of the fluoro-ketone were obtained as a yellow solid.

IR (thin film) 1651, 1607 cm$^{-1}$; FDMS m/e 479 (M$^+$,$^{35}$Cl) and 481 (M$^+$,$^{37}$Cl); Anal. Calcd. for $C_{27}H_{23}ClFNO_2S$: C, 67.56; H, 4.83; N, 2.92. Found: C, 67.84; H, 4.87; N, 2.83.

B. 3-Chloro-4-(dimethylaminooxy)phenyl 2-[4-[2-(1-Pyrrolidinyl)ethoxy]phenyl]benzo[b]thiophen-3-yl Ketone.

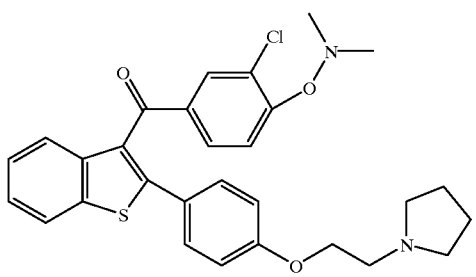

Sodium hydride (60% in oil; 130 mg, 3.24 mmol) was added to a stirred solution of the above fluoro-ketone (391 mg, 0.815 mmol) and N,N-dimethylhydroxylamine hydrochloride (159 mg, 1.63 mmol) in anhydrous DMF (4 mL) at room temperature under nitrogen atmosphere. The mixture was stirred for 2 h. The mixture was diluted with EtOAc (25 mL) before it was washed with water (20 mL). The aqeous layer was extracted with EtOAc (20 mL), and the combined organic layers were washed with brine (10 mL), dried over $MgSO_4$, filtered, concentrated, and chromatographed on silica [gradient 0–6% $Et_3N$ in THF/hexane (1/1)] to give a 359 mg (85%) of the 0-substituted hydroxylamine as a gum.

IR (neat) 1649, 1608 cm$^{-1}$; FDMS m/e 520 (M$^+$, $^{35}$Cl), 522 (M$^+$, $^{37}$Cl); Anal. Calcd. for $C_{29}H_{29}ClN_2O_3S$: C, 66.85; H, 5.61; N, 5.38. Found: C, 66.75; H, 5.74; N, 5.68.

C. 3-Chloro-4-(dimethylaminooxy)phenyl 2-[4-[2-(1-Pyrrolidinyl)ethoxy]phenyl]benzo[b]thiophen-3-yl Ketone Oxalate.

Following the procedure described in Example 3-D, the salt was obtained from the above compound as a yellowish solid in an 85% yield.

IR (KBr) 3400–2500 (br), 1724, 1647, 1605 cm$^{-1}$; FDMS m/e 520 (M$^+$-$C_2H_2O_4$, $^{35}$Cl), 522 (M$^+$-$C_2H_2O_4$, $^{37}$Cl).

EXAMPLE 6

Preparation of 3-Chloro-4-(diethylaminooxy)phenyl 2-[4-[2-(1-pyrrolidinyl)ethoxy]phenyl]benzo[b] thiophen-3-yl Ketone Oxalate.

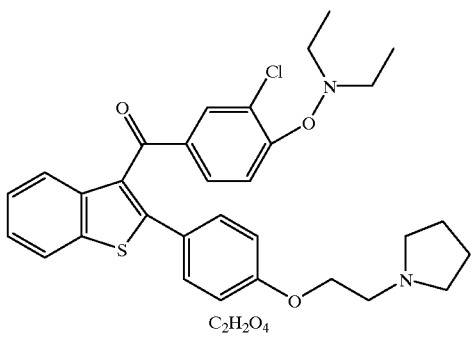

A. 3-Chloro-4-(diethylaminooxy)phenyl 2-[4-[2-(1-pyrrolidinyl)ethyloxy]phenyl]benzo[b] thiophen-3-yl Ketone.

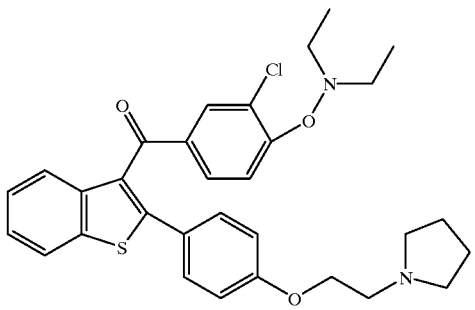

Following the procedure described in Example 5-B, but using N,N-diethylhydroxylamine, the named compound was obtained from the fluoro-ketone of Example 5-A. Column chromatography on silica [gradient 60–90% THF in hexanes] gave 176 mg (41%) of the hydroxylamine as a yellow oil.

IR (thin film) 2973, 1647, 1609 cm$^{-1}$; FDMS m/e 549 (M$^+$,$^{35}$Cl) and 551 (M$^+$,$^{37}$Cl).

B. 3-Chloro-4-(diethylaminooxy)phenyl 2-[4-[2-(1-pyrrolidinyl)ethoxy]phenyl]benzo[b]thiophen-3-yl Ketone Oxalate.

Following the procedure described in Example 1-F, the oxalate was obtained from the above hydroxylamine as a yellow solid in a 83% yield.

IR (KBr) 2850–2200 (br), 1643, 1606 cm$^{-1}$; FABMS m/e 549 (M$^+$–1[C$_2$H$_2$O$_4$], $^{35}$Cl) and 551 (M$^+$–1[C$_2$H$_2$O$_4$], $^{37}$Cl).

EXAMPLE 7

Preparation of 3-Chloro-4-[(2-thiazolyl)thio]phenyl 2-[4-[2-(1-pyrrolidinyl)ethoxy]phenyl]benzo[b]thio-phen-3-yl Ketone Oxalate.

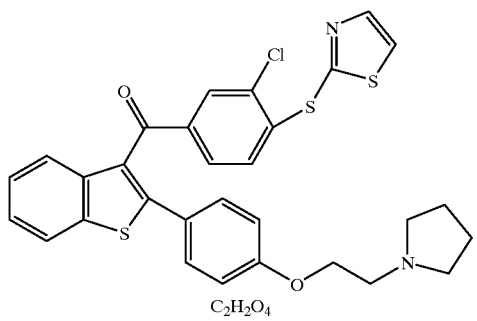

A. 3-Chloro-4-[(2-thiazolyl)-thio]phenyl 2-[4-[2-(1-Pyrrolidinyl)ethoxy]phenyl]benzo[b]thiophen-3-yl Ketone.

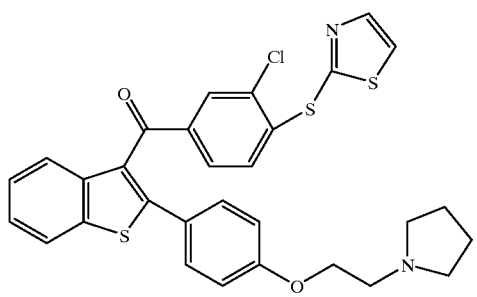

Following the procedure described in Example 5-B, but using 2-mercaptothiazole, the thioether compound was obtained from the fluoro-ketone of Example 5-A as a gum in a 75% yield.

IR (neat) 1658, 1642, 1606 cm$^{-1}$; FDMS m/e 577 (M$^{++}$1, $^{35}$Cl), 579 (M$^+$+1, $^{37}$Cl).

B. 3-Chloro-4-[(2-thiazolyl)-thio]phenyl 2-[4-[2-(1-pyrrolidinyl)ethoxy]phenyl]benzo[b]thiophen-3-yl Ketone Oxalate.

Following the procedure described in Example 3-D, the oxalate was obtained from the above thioether as a yellowish solid in a 76% yield.

IR (KBr) 3400–2500 (br), 1714, 1700, 1649, 1606 cm$^{-1}$; FDMS m/e 577 (M$^+$+1-C$_2$H$_2$O$_4$, $^{35}$Cl), 579 (M$^+$+1-C$_2$H$_2$O$_4$, $^{37}$Cl). Anal. Calcd. for C$_{30}$H$_{25}$ClN$_2$O$_2$S$_3$·C$_2$H$_2$O$_4$: C, 57.61; H, 4.08; N, 4.20. Found: C, 57.90; H, 4.14; N, 4.25.

EXAMPLE 8

Preparation of 3-[3-Chloro-4-[(2-thiazolyl)thiolbenzyl]-2-[4-[2-(1-pyrrolidinyl)ethoxy]phenyl]benzo[b]thiophene Oxalate.

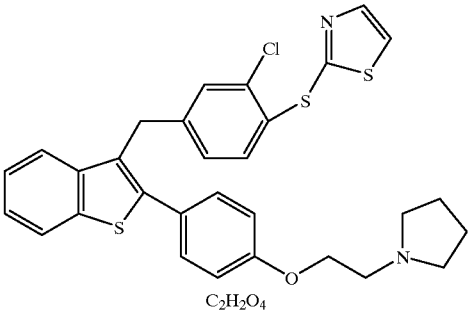

A. 3-[3-Chloro-4-[(2-thiazolyl)thio]benzyl]-2-[4-[2-(1-pyrrolidinyl)ethoxy]phenyl]benzo[b]thiophene.

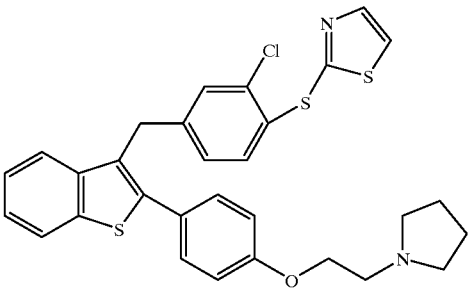

Following the procedure described in Example 3-D, the oxalate was obtained from the above methylene compound as a 7-A as a foam in an overall 91% yield.

IR (neat) 1606 cm$^{-1}$; FDMS m/e 563 (M$^+$+1, $^{35}$Cl), 565 (M$^+$+1, $^{37}$Cl).

B. 3-[3-Chloro-4-[(2-thiazolyl)thio]benzyl]-2-[4-[2-(1-pyrrolidinyl)ethoxy]phenyl]benzo[b]thiophene Oxalate.

Following the procedure described in Example 3-D, the oxalate was obtained from the above methylene compound as a white solid in an 89% yield.

IR (KBr) 3400–2500 (br), 1719, 1632, 1607 cm$^{-1}$; FDMS m/e 563 (M$^+$+1-C$_2$H$_2$O$_4$, $^{35}$Cl), 565 (M$^+$+1-C$_2$H$_2$O$_4$, $^{37}$Cl). Anal. Calcd. for C$_{30}$H$_{27}$ClN$_2$OS$_3$·C$_2$H$_2$O$_4$: C, 58.84; H, 4.47; N, 4.29. Found: C, 58.92; H, 4.38; N, 3.99.

EXAMPLE 9

Preparation of 4-Cyanomethyl-3-methoxyphenyl 2-[4-[2-(1-Pyrrolidinyl)ethyloxy]phenyl]benzo b]thiophen-3-yl Ketone Oxalate.

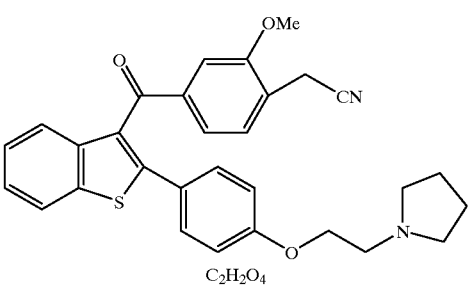

A. Methyl 4-Cyanomethyl-3-methoxybenzoate.

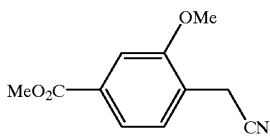

AIBN (274 mg) was added to a stirred suspension of methyl 3-methoxy-4-methylbenzoate (20.10 g, 112.0 mmol) and NBS (23.84 g, 134 mmol) in CCl$_4$ (730 mL), and the resultant mixture was heated to reflux for 3 h. At room temperature, the mixture was diluted with hexanes (350 mL) before it was filtered and concentrated to give 28.59 g (crude yield 99%) of the brominated product.

Part of the crude brominated product (8.10 g) was dissolved in anhydrous THF (70 mL). 18-Crown-6 (413 mg, 1.56 mmol) was added followed by KCN (3.05 g, 46.9 mmol); then the resulting mixture was heated at 65° C. for 20 h. The reaction mixture was diluted with H$_2$O (50 mL) and EtOAc (250 mL), then the aqueous layer was extracted with EtOAc (2×100 mL). The combined organic layers were dried over MgSO$_4$, filtered, and concentrated to give an oily residue, which was chromatographed on silica [gradient 5–20% EtOAc in hexanes] to provide 2.50 g of the cyanomethyl compound (39%) as a white solid.

IR (KBr) 2260, 1714, cm$^{-1}$; FDMS m/e 205 (M$^+$).

B. 4-Cyanomethyl-3-methoxybenzoyl Chloride.

Using procedures similar to those described below in Example 17-B, the above benzoate was hydrolyzed and converted into the corresponding benzoyl chloride.

C. 4-Cyanomethyl-3-methoxyphenyl 2-[4-[2-(1-Pyrrolidinyl)-ethoxy]phenyl]benzo[b]thiophen-3-yl Ketone.

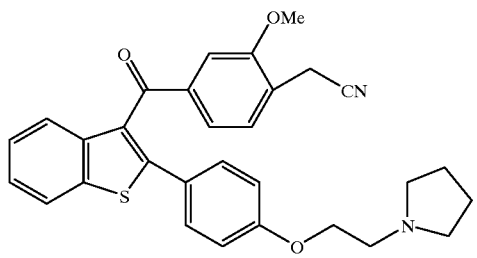

Following the procedure described in Example 5-A, the ketone was obtained from the above benzoyl chloride and 2-[4-[2-(1-pyrrolidinyl)ethoxy]phenyl]benzo[b]thiophene. Column chromatography on silica [gradient 60–90% THF in hexanes] gave 190 mg (41%) of the ketone as a yellow oil.

IR (thin film) 2965, 2256, 1651, 1606 cm$^{-1}$; FDMS m/e 497 (M$^+$+1); Anal. Calcd. for C$_{30}$H$_{28}$N$_2$O$_3$S: C, 72.56; H, 5.68; N, 5.64. Found: C, 72.72; H, 5.93; N, 5.60.

D. 4-Cyanomethyl-3-methoxyphenyl 2-[4-[2-(1-pyrrolidinyl)-ethoxy]phenyl]benzo[b]thiophen-3-yl Ketone Oxalate.

Following the procedure described in Example 1-F, the salt was obtained from the above ketone as a yellow foam in a 83% yield.

IR (KBr) 3450 (br), 3300–2200 (br), 1717, 1645, 1605 cm$^{-1}$; FDMS m/e 497 (M$^+$+1-1[C$_2$H$_2$O$_4$]); Anal. Calcd. for C$_{30}$H$_{28}$N$_2$O$_3$S 0.70 (C$_2$H$_2$O$_4$): C, 67.39; H, 5.30; N, 5.01. Found: C, 67.31; H, 5.01; N, 4.98.

EXAMPLE 10

Preparation of 1-[2-[2-Methoxy-4-[[6-hydroxy-2-[4-[2-(1-pyrrolidinyl)ethoxy]phenyl]benzo[b]thiophen-3-yl]methyl]-phenoxy]ethyl]succinimide Oxalate.

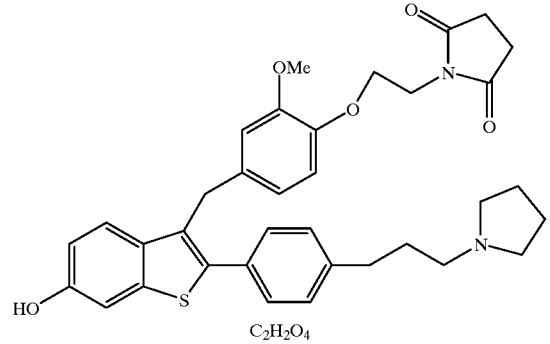

A. 3-Methoxy-4-triisopropylsilyloxybenzoic Acid.

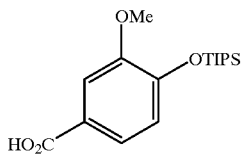

A 0° C. solution of vanillic acid (20 g; 119 mmol) in 550 mL of dry DMF and 33 mL of TEA was treated with TIPS-triflate (48 mL; 179 mmol) dropwise via a syringe. After 15 min, the reaction mixture was allowed to warm to ambient temperature. After stirring overnight, the reaction mixture was poured into 500 mL of saturated NaHCO$_3$ (aq) and 300 mL of EtOAc. The aqueous layer was extracted with EtOAc (3×200 mL). The combined organic layers were washed with H$_2$O (300 mL), dried over MgSO$_4$, filtered and concentrated in vacuo. Purification by PrepLC (SiO$_2$; 5% EtOAc in hexanes) afforded 22.5 g (69.3 mmol; 58%) of the title compound as fluffy white crystals.

FDMS 324 (M$^+$); Anal. Calcd. for C$_{17}$H$_{28}$O$_4$Si: C, 62.92; H, 8.70. Found: C, 62.70; H, 8.81.

B. 6-Benzyloxy-2-(dimethylamino)benzo[b]thiophen-3-yl 3-Methoxy-4-triisopropylsilyloxyphenyl Ketone.

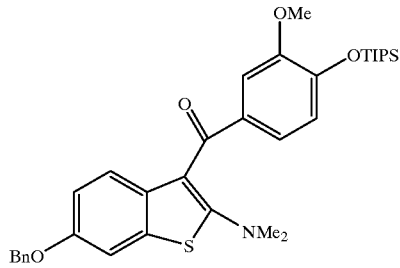

A slurry of 3-methoxy-4-triisopropylsilyloxybenzoic acid (9.75 g, 30 mmol; Part A) in 300 mL of dichloroethane and 1 drop of DMF was treated with oxalyl chloride (13.1 mL, 150 mmol) and stirred overnight at ambient temperature. The reaction mixture was concentrated in vacuo and suspended in 300 mL of chlorobenzene. 6-Benzyloxy-2-(N,N-dimethylamino)-benzo[b]thiophene (8.5 g, 30 mmol) was added, and the resulting mixture was heated at 105° C. for 5 h. After cooling to ambient temperature, the reaction mixture was poured into 500 mL of saturated NaHCO₃ solution. The aqueous layer was extracted with CHCl₃ (3×150 mL). The combined organics were dried over K₂CO₃, filtered and concentrated in vacuo. Purification by flash chromatography (SiO₂; gradient of 5% to 10% EtOAc in hexanes) afforded 6.05 g (10.3 mmol; 34%) of the title compound.

FDMS 589 (M⁺); Anal. Calcd. for C₃₄H₄₃NO₄SSi: C, 69.23; H, 7.35; N, 2.37. Found: C, 69.54; H, 7.40; N, 2.32.

C. 6-Benzyloxy-2-[4-[2-(1-pyrrolidinyl)ethoxy]phenyl]-benzo[b]thiophen-3-yl 3-Methoxy-4-triisopropylsilyloxyphenyl Ketone.

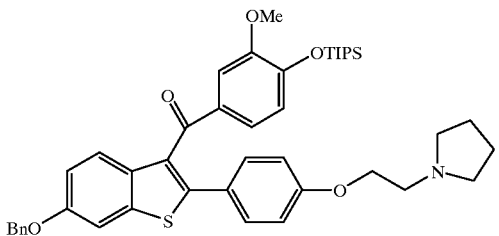

A suspension of 1-[2-(4-bromophenoxy)ethyl]pyrrolidine (3.1 mL, 15 mmol), Mg° (365 mg, 15 mmol) and a small crystal of I₂ in 20 mL of dry THF was heated at 60° C. for 1 h. The resulting solution was added via cannula to a 0° C. solution of 6-benzyloxy-2-[4-[2-(1-pyrrolidinyl)ethoxy]phenyl]-benzo[b]thiophen-3-yl 3-methoxy-4-triisopropylsilyloxyphenyl ketone (5.75 g, 9.75 mmol; Part B) in 100 mL of dry THF. After 2.5 h, the reaction mixture was poured into 200 mL of saturated NH₄Cl solution. The aqueous layer was extracted with CHCl₃ (3×150 mL). The combined organics were dried over K₂CO₃, filtered and concentrated in vacuo. Purification by PrepLC (SiO₂; gradient of 90:8:2 to 75:20:5 hex/THF/TEA) afforded 4.89 g (6.65 mmol; 68%) of the title compound.

FDMS 736 (M+1); Anal. Calcd. for C₄₄H₅₃NO₅SSi: C, 71.80; H, 7.26; N, 1.90. Found: C, 71.55; H, 7.11; N, 1.81.

D. 6-Benzyloxy-2-[4-[2-(1-pyrrolidinyl)ethoxy]phenyl]-benzo[b]thiophen-3-yl 3-Methoxy-4-hydroxyphenyl Ketone.

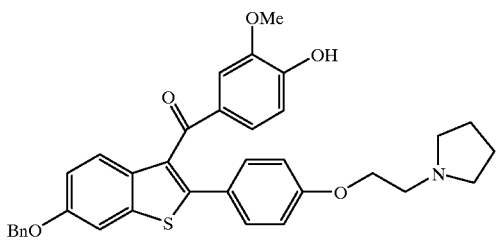

A solution of 6-benzyloxy-2-[4-[2-(1-pyrrolidinyl)-ethoxy]phenyl]benzo[b]thiophen-3-yl 3-methoxy-4-triisopropylsilyloxyphenyl ketone (Part C; 4.89 g; 6.64 mmol) in 65 mL of dry THF was treated with tetrabutylammonium fluoride (1 M solution in THF; 7.3 mL) in a dropwise fashion. After 10 min, the reaction mixture was poured into 100 mL of saturated NaHCO₃ (aq). The aqueous layer was extracted with EtOAc (3×50 mL). The combined organic layers were dried over K₂CO₃, filtered and concentrated in vacuo to give a quantitative yield of the title compound as a orange foam. An analytical sample was purified by radial chromatography (SiO₂; gradient of 1% to 3% MeOH in CHCl₃).

FDMS 580 (M+1); Anal. Calcd. for C₃₅H₃₃NO₅S.0.5H₂O: C, 71.41; H, 5.82; N, 2.38. Found: C, 71.61; H, 5.71; N, 2.41.

E. 6-Benzyloxy-3-(3-methoxy-4-hydroxybenzyl)-2-[4-[2-(1-pyrrolidinyl)ethoxy]phenyl]benzo[b]thiophene.

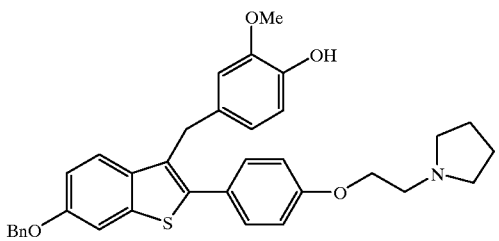

A 0° C. solution of 6-benzyloxy-2-[4-[2-(1-pyrrolidinyl) ethoxy]phenyl]benzo[b]thiophen-3-yl 3-methoxy-4-hydroxyphenyl ketone (Part D; 3.85 g, 6.64 mmol) in 100 mL of anhydrous THF was treated with DIBAL-H (17 mL, 1M solution in toluene) dropwise via syringe. After 1 hr at 0° C., the remaining DIBAL-H was quenched with excess MeOH. 100 mL of saturated Na+K+tartrate and 50 mL of EtOAc were added, and the biphasic mixture was vigorously stirred for 1.5 hr at ambient temperature. The layers were separated, and the aqueous layer was extracted with EtOAc (2×100 mL). The combined organic layers were dried over K₂CO₃, filtered and concentrated in vacuo. The crude residue was dissolved in 100 mL of 1,2-dichloroethane, and Et₃SiH (9.4 mL, 58.7 mmol) was added. Upon cooling to 0° C., TFA (6.5 mL, 83.8 mmol) was added in a dropwise fashion. After 1.5 hr. the reaction mixture was poured into 300 mL of saturated NaHCO₃ solution. The aqueous phase was extracted with EtOAc (2×150 mL). The combined organic layers were dried over K₂CO₃, filtered and concentrated in vacuo. Purification by PrepLC (SiO₂; gradient of 0.5% to 2% MeOH in CHCl₃, saturated with NH₄OH) afforded 3.1 g (5.48 mmol; 83%) of a white solid.

FDMS 566 (M+1); Anal. Calcd. for C₃₅H₃₅NO₄S: C, 74.31; H, 6.24; N, 2.48. Found: C, 74,11; H, 6.32; N, 2.46.

F. 1-[2-[2-Methoxy-4-[[6-benzyloxy-2-[4-[2-(1-pyrrolidinyl)ethoxy]phenyl]benzo[b]thiophen-3-yl]methyl] phenoxy]-ethyl]succinimide.

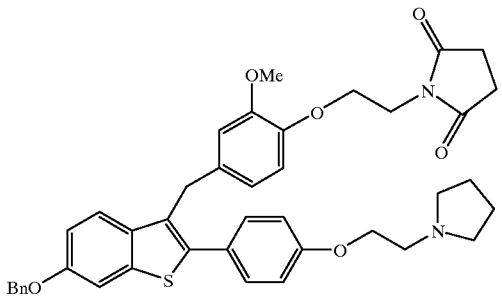

The title compound was prepared from 6-benzyloxy-3-[(3-methoxy-4-hydroxyphenyl)-2-[4-[2-(1-pyrrolidinyl) ethoxy]-phenyl]benzo[b]thiophene (Part E) and N-(2-hydroxyethyl)-succinimide by essentially using the following general procedure. A mixture of the phenol (1 eq), triphenyl-phosphine (4 eq), and the alcohol (4 eq) in THF (about 1.3 mL/eq of phenol) was cooled to 0° C. and was treated with diethyl azodicarboxylate (4 eq). The cooling bath was removed and the reaction mixture was stirred at ambient temperature for 16 h. The mixture was concentrated in vacuo and purified by chromatography to provide the named ether.

FDMS 691 (M+1); Anal. Calcd. for C₄₁H₄₂N₂O₆S: C, 71.28; H, 6.13; N, 4.05. Found: C, 71.05; H, 6.21; N, 3.80.

G. 1-[2-[2-Methoxy-4-[[6-hydroxy-2-[4-12-(1-pyrrolidinyl)-ethoxy]phenyl]benzo[b]thiophen-3-yl]methyl]phenoxy]ethyl]-succinimide Oxalate.

The title compound was prepared from 1-[2-[2-methoxy-4-[[6-benzyloxy-2-[4-[2-(1-pyrrolidinyl)ethoxy]phenyl]-benzo[b]thiophen-3-yl]methyl]phenoxy]ethyl]succinimide (Part F) in 96% yield by following procedures similar to those outlined in Example 1-F.

FDMS 601 (M+1); Anal. Calcd. for C₃₄H₃₆N₂O₆S.C₂H₂O₄: C, 62.60; H, 5.54; N, 4.05. Found: C, 62.40; H, 5.41; N, 3.89.

EXAMPLE 11

Preparation of 1-[2-[2-Methoxy-4-[[6-hydroxy-2-[4-[2-(1-pyrrolidinyl)ethoxy]phenyl]benzo[b]thiophen-3-yl]methyl]-phenoxylethyl]imidazolidin-2-one Oxalate.

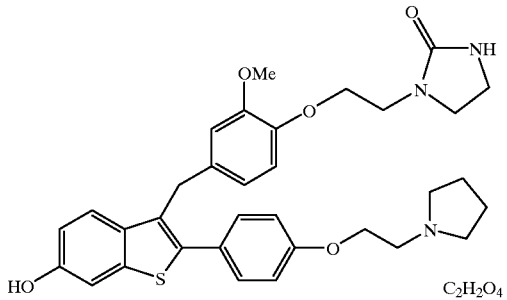

A. 1-[2-[2-Methoxy-4-[[6-benzyloxy-2-[4-[2-(1-pyrrolidinyl)ethoxy]phenyl]benzo[b]thiophen-3-yl]methyl]phenoxy]-ethyl]imidazolidin-2-one.

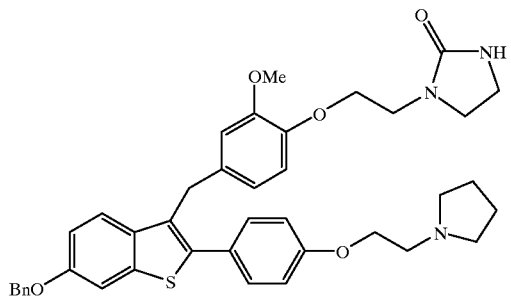

The title compound was prepared from 6-benzyloxy-3-(3-methoxy-4-hydroxybenzyl)-2-(4-[2-(1-pyrrolidinyl)ethoxy]-phenyl]benzo[b]thiophene (Example 10, Part E) and 1-(2-hydroxyethyl)-2-imidazolidinone in 40% yield by essentially following the procedure detailed in Example 10-F.

FDMS 678 (M+1); Anal. Calcd. for C₄₀H₄₃N₃O₅S: C, 70.88; H, 7.39; N, 6.20. Found: C, 71.18; H, 7.57; N, 5.90.

B. 1-[2-[2-Methoxy-4-[[6-hydroxy-2-[4-[2-(1-pyrrolidinyl)-ethoxy]phenyl]benzo[b]thiophen-3-yl]methyl]phenoxy]-ethyl]imidazolidin-2-one Oxalate.

The title compound was prepared in 32% yield from 1-[2-[2-methoxy-4-[[6-benzyloxy-2-[4-[2-(1-pyrrolidinyl)-ethoxy]phenyl]benzo[b]thiophen-3-yl)methyl]phenoxy]ethyl]-imidazolidin-2-one (Part A) by following procedures similar to those outlined in Example 1-F.

FDMS 588 (M+1); Anal. Calcd. for C₃₄H₃₇N₃O₅S. 1.5C₂H₂O₄.0.1H₂O: C, 58.37; H, 5.71; N, 5.67. Found: C, 58.27; H, 5.51; N, 5.46.

EXAMPLE 12

Preparation of 1-[2-[2-Methoxy-4-[[6-hydroxy-2-14-[2-(1-pyrrolidinyl)ethoxy]phenyl]benzo[b]thiophen-3-yl]methyl]-phenoxy]ethyl]cyclopentane Oxalate.

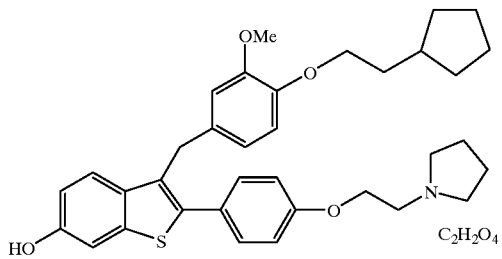

A. 1-[2-[2-Methoxy-4-[[6-benzyloxy-2-[4-[2-(1-pyrrolidinyl)ethoxy]phenyl]benzo[b]thiophen-3-yl]methyl]phenoxy]-ethyl]cyclopentane.

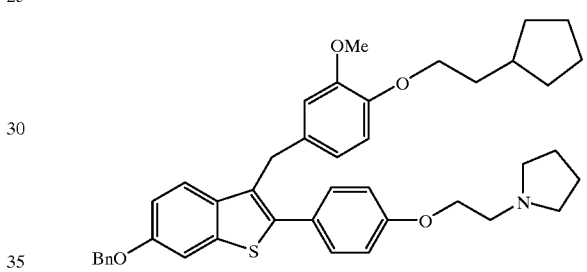

The title compound was prepared from 6-benzyloxy-3-(3-methoxy-4-hydroxybenzyl)-2-[4-[2-(1-pyrrolidinyl)ethoxy]-phenyl]benzo[b]thiophene (Example 10-E) and 2-cyclopentyl-ethanol in 58% yield by a method similar to that described in Example 10-F. A small sample was converted to the oxalate salt by a method similar to that described in Example 1-F.

FDMS 662 (M+1); Anal. Calcd. for C₄₂H₄₇NO₄S.C₂H₂O₄.1.2H₂O: C, 68.32; H, 6.70; N, 1.81. Found: C, 67.92; H, 6.32; N, 1.91.

B. Preparation of 1-[2-[2-Methoxy-4-[[6-hydroxy-2-[4-[2-(1-pyrrolidinyl)ethoxy]phenyl]benzo[b]thiophen-3-yl]methyl]-phenoxy]ethyl]cyclopentane Oxalate.

The title compound was prepared from 1-[2-[2-methoxy-4-[[6-benzyloxy-2-[4-[2-(1-pyrrolidinyl)ethoxy]phenyl]-benzo[b]thiophen-3-yl]methyl]phenoxy]ethyl]cyclopentane (Part A) in 48% yield by following procedures similar to those outlined in Example 1-F.

FDMS 572 (M+1); Anal. Calcd. for C₃₅H₄₁NO₄S.0.8C₂H₂O₄: C, 68.28; H, 6.67; N, 2.18. Found: C, 68.34; H, 6.67; N, 2.03.

EXAMPLE 13

Preparation of 1-[2-[2-Methoxy-4-[[6-hydroxy-2-[4-[2-(1-pyrrolidinyl)ethoxy]phenyl]benzo[b]thiophen-3-yl]methyl]-phenoxy]ethyl]pyrrolidinone Oxalate.

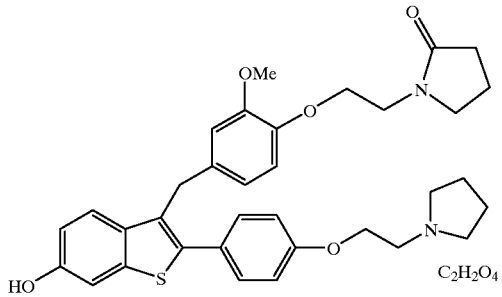

A. 1-[2-[2-Methoxy-4-[[6-benzyloxy-2-[4-[2-(1-pyrrolidinyl)ethoxy]phenyl]benzo[b]thiophen-3-yl]methyl]phenoxy]-ethyl]pyrrolidinone.

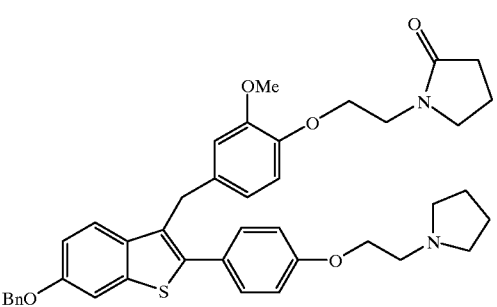

The title compound was prepared from 6-benzyloxy-3-(3-methoxy-4-hydroxybenzyl)-2-[4-[2-(1-pyrrolidinyl)ethoxy]-phenyl]benzo[b]thiophene (Example 10-E) and 1-(2-hydroxy-ethyl)-2-pyrrolidinone in 58% yield by a method similar to that described in Example 10-F.

FDMS 677 (M+1); Anal. Calcd. for $C_{41}H_{44}N_2O_5S \cdot 0.5H_2O$: C, 71.80; H, 6.61; N, 4.08. Found: C, 72.01; H, 6.83; N, 4.45.

B. 1-[2-[2-Methoxy-4-[[6-hydroxy-2-[4-[2-(1-pyrrolidinyl)-ethoxy]phenyl]benzo[b]thiophen-3-yl]methyl]phenoxy] ethyl]-pyrrolidinone Oxalate.

The title compound was prepared in 46% yield from 1-[2-[2-methoxy-4-[[6-benzyloxy-2-[4-[2-(1-pyrrolidinyl) ethoxy]-phenyl]benzo[b]thiophen-3-yl]methyl] phenoxyethyl]-pyrrolidinone (Part A) by following procedures similar to those outlined in Example 1-F.

FDMS 587 (M+1); Anal. Calcd. for $C_{34}H_{38}N_2O_5S \cdot C_2H_2O_4 \cdot 1.5H_2O$: C, 61.44; H, 6.16; N, 3.98. Found: C, 61.48; H, 5.87; N, 3.98.

EXAMPLE 14

Preparation of (±)-6-Hydroxy-2-[4-[2-(1-pyrrolidinyl)-ethoxy]phenyl]benzo[b]thiophen-3-yl 4-[trans-2-(2-Oxo-oxazolidin-3-yl)cyclohexyloxy]phenyl Ketone.

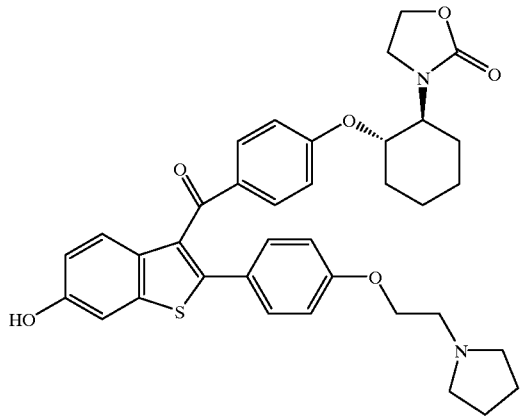

A. (±)-trans-2-(2-Oxooxazolidin-3-yl)cylohexanol.

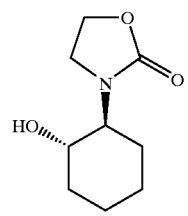

To an ice-cold (about 20% by weight) aqueous solution of $K_2CO_3$ (3 mol/mol epoxide) was added 2-oxazolidone (1 mol/mol epoxide), followed by cyclohexene oxide. After 5 min, the ice bath was removed and the cloudy solution was stirred at room temperature overnight (18 h). The mixture was then extracted with EtOAc which was washed with $H_2O$ and brine. The combined extracts were dried over $MgSO_4$, concentrated, and dried under vacuum to afford the named alcohol (6%) which was used without further purification for the following reaction.

$^1$H NMR (CDCl$_3$) δ 6.36 (br s, 1H), 4.25–4.41 (m, 2H), 3.43–3.66 (m, 5H), 3.26 (br s, 1H), 2.05 (m, 1H), 1.68–1.77 (m, 2H), 1.20–1.38 (m, 3H); FDMS 185 (M$^+$).

B. 6-Benzyloxy-2-[4-[2-(1-pyrrolidinyl)ethoxy]phenyl]-benzo[b]thiophen-3-yl 4-Fluorophenyl Ketone.

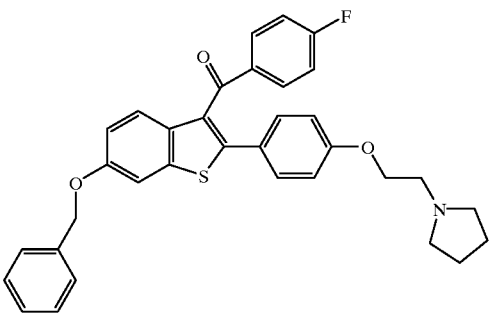

zUsing a procedure similar to that described in Example 1-A, 6-benzyloxy-2-(dimethylamino)benzo[b]thiophene was acylated with p-fluorobenzoyl choride to afford 6-benzyloxy-2-(dimethylamino)benzo[b]thiophen-3-yl 4-fluorophenyl ketone which was treated with 4-[2-(1-pyrrolidinyl) ethoxy]phenyl magnesium bromide using a procedure similar to that described in Example 1-B to afford title compound in 84% overall yield.

FDMS 551 (M+); Anal. Calcd for $C_{34}H_{30}NO_3S$: C, 74.02; H, 5.48; N, 2.54. Found: C, 73.89; H, 5.70; N, 2.63.

C. (±)-6-Benzyloxy-2-[4-[2-(1-pyrrolidinyl)ethoxy] phenyl]-benzo[b]thiophen-3-yl 4-[trans-2-(2-Oxooxazolidin-3-yl)-cyclohexyloxy]phenyl Ketone.

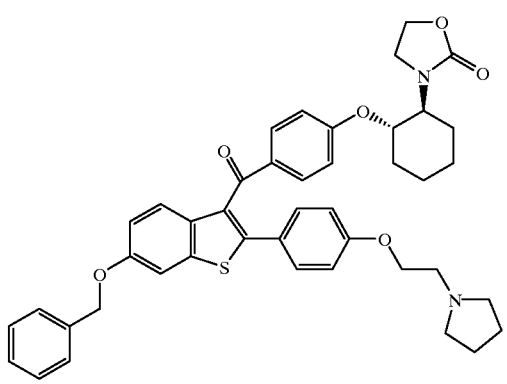

Using a procedure similar to that described below in Example 19, the title compound was prepared in 49% yield from (±)-trans-2-(2-oxooxazolidin-3-yl)cylohexanol (Part A) and 6-benzyloxy-2-[4-[2-(1-pyrrolidinyl)ethoxy] phenyl]-benzo[b]thiophen-3-yl 4-fluorophenyl ketone (Part B).

FDMS 718 (M+1); Anal. Calcd for $C_{43}H_{44}N_2O_6S$: C, 72.04; H, 6.19; N, 3.91. Found: C, 72.25; H, 6.48; N, 4.23.

D. (±)-6-Hydroxy-2-[4-[2-(1-pyrrolidinyl)ethoxy]phenyl]-benzo[b]thiophen-3-yl 4-[trans-2-(2-Oxooxazolidin-3-yl)-cyclohexyloxy]phenyl Ketone.

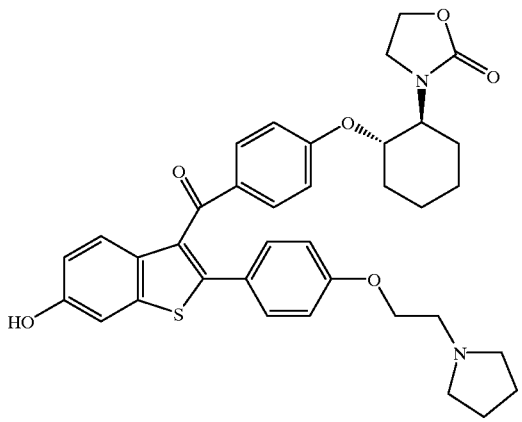

A slurry of the (±)-6-benzyloxy-2-[4-[2-(1-pyrrolidinyl) ethoxy]phenyl]benzo[b]thiophen-3-yl 4-[trans-2-(2-oxooxazolidin-3-yl)cyclohexyloxy]phenyl ketone (Part C) and an equal weight of 10% Pd/C in a 1:1 mixture of THF-EtOH was stirred under positive hydrogen pressure (from balloon) for about 19 h. The reaction mixture was filtered through a pad of diatomaceous earth and washed with THF. The filtrate was then concentrated under reduced pressure and the residue was flash chromatographed (silica gel, 10%[10% $NH_4OH$ in $MeOH]/CH_2Cl_2$) to afford the title compound in 62% yield.

FDMS 627 (M+); Anal. calcd for $C_{36}H_{38}N_2O_6S \cdot 1.0H_2O$: C, 67.06; H, 6.25; N, 4.34. Found: C, 67.43; H, 5.95; N, 4.33.

EXAMPLE 15

Preparation of (±)-6-Hydroxy-3-[4-[trans-2-(2-oxooxazolidin-3-yl)cyclohexyloxy]benzyl]-2-[4-[2-(1-pyrrolidinyl)ethoxy]-phenyl]benzo[b]thiophene.

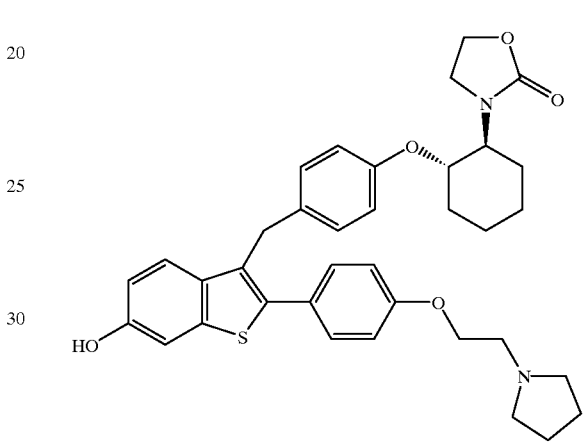

A. (±)-6-Benzyloxy-α-[4-[trans-2-(2-oxooxazolidin-3-yl)-cyclohexyloxy]phenyl]-2-[4-[2-(1-pyrrolidinyl)ethoxy]-phenyl]benzo[b]thiophene-3-methanol.

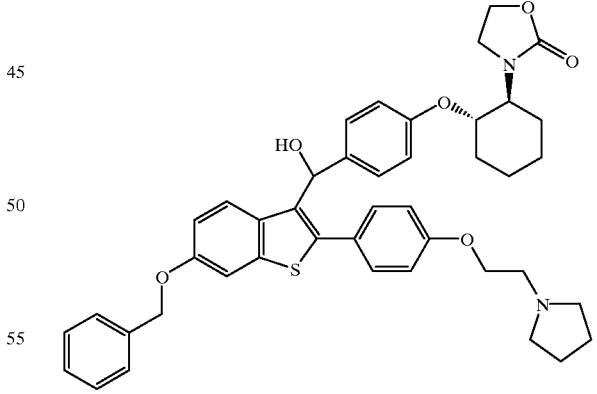

To the (±)-6-benzyloxy-2-[4-[2-(1-pyrrolidinyl)ethoxy]-phenyl]benzo[b]thiophen-3-yl 4-[trans-2-(2-oxooxazolidin-3-yl)cyclohexyloxy]pheny] ketone (57.3 mg, 0.0799 mmol) (Example 14, Part C) dissolved in 0.8 mL of dry THF was added 0.40 mL (0.40 mmol) of 1 M lithium tri-tert-butoxy-aluminohydride in THF at room temp. The solution was stirred for 16 h. The reaction was then cooled to 0° C. and quenched with 3 mL of saturated K+Na+tartrate solution.

The mixture was extracted (3×20 mL) with EtOAc. The combined organic layers were dried over MgSO$_4$, concentrated under reduced pressure, and purified by flash chromatography (silica gel, 6%[10% NH$_4$OH/MeOH]/CH$_2$Cl$_2$) to afford 38.1 mg (0.0529 mmol, 66%) of a white foam.

$^1$HNMR (CDCl$_3$) δ 7.61 (m, 1H), 7.26–7.47 (m, 11H), 6.92 (d, J=8.8 Hz, 2H), 6.86 (d, J=8.6 Hz, 2H), 6.14 (s, 1H), 5.10 (s, 2H), 3.78–4.17 (m, 6H), 3.46 (m, 1H), 3.25 (m, 1H), 2.96 (dist. t, 2H), 2.70 (m, 4H), 2.25 (m, 1H), 1.82 (m, 2H), 1.25–1.65 (m, 4H).

B. (±)-6-Benzyloxy-3-[4-[trans-2-(2-oxooxazolidin-3-yl)-cyclohexyloxy]benzyl]-2-[4-[2-(1-pyrrolidinyl)ethoxy]-phenyl]benzo[b]thiophene.

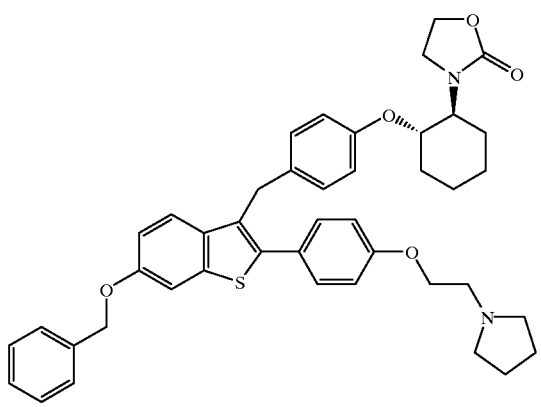

The title compound was prepared in 86% yield from the above alcohol (Part A) by a procedure similar to that of the second step of Example 1-D.

$^1$HNMR (CDCl$_3$) δ 7.30–7.52 (m, 9H), 6.92–7.16 (m, 5H), 6.80 (d, J=8,7 Hz, 2H), 5.12 (s, 2H), 3.70–4.25 (m, 9H), 3.47 (m, 1H), 3.28 (m, 1H), 3.00 (dist. t, 2H), 2.75 (m, 4H), 2.28 (m, 1H), 1.70–1.95 (m, 6H), 1.15–1.65 (m, 4H).

C. (±)-6-Hydroxy-3-[4-[trans-2-(2-oxooxazolidin-3-yl)-cyclohexyloxy]benzyl]-2-[4-[2-(1-pyrrolidinyl)ethoxy]-phenyl]benzo[b]thiophene.

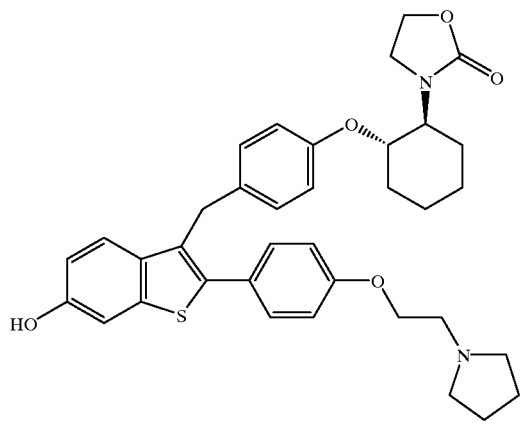

The title compound was prepared in 52% yield from (±)-6-benzyloxy-3-[4-[trans-2-(2-oxooxazolidin-3-yl)-cyclohexyloxy]benzyl]-2-[4-[2-(1-pyrrolidinyl)ethoxy]-phenyl]benzo[b]thiophene (Part B) by essentially following the procedures outlined in Example 14-D.

FDMS 613 (M$^+$); Anal. calcd for C$_{36}$H$_{40}$N$_2$O$_5$S·0.76CH$_2$Cl$_2$: C, 65.19; H, 6.18; N. 4.14. Found: C, 65.20; H, 6.02; N, 3.95

EXAMPLE 16

Preparation of 4-(4-(2-Oxopyrrolidin-3-yl)ethoxy]phenyl 2-[4-[2-(1-Pyrrolidinyl)ethoxy]phenyl]benzo[b]thiophen-3-yl Ketone Oxalate Hydrate.

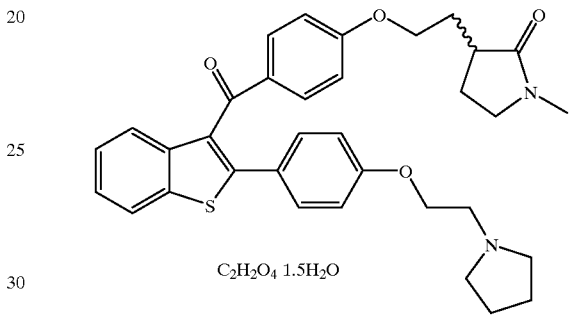

By using a procedure similar to that of Example 19, the title compound was prepared from 4-fluorophenyl 2-[4-[2-(1-pyrrolidinyl)ethoxy]phenyl]benzo[b]thiophen-3-yl ketone (prepared from 4-fluorobenzoyl chloride using a procedure similar to that of Example 5-A, and 3-(2-hydroxyethyl)-1-methylpyrrolidin-2-one (Wolfgang Sucrow, Marion Slopianka and Dieter Winkler, Chem. Ber., 105, p 1621–1633 (1972)), in 39% yield. The product was isolated by flash chromatography on silica gel, eluting with a gradient of EtOAc (100–90%)/-Et$_3$N (0–5%)/MeOH (0–5%).

$^1$H NMR (CDCl$_3$) δ 7.97 (d, J=6 Hz, 1H), 7.90 (d, J=8 Hz, 2H), 7.77 (d, J=6 Hz, 1H), 7.49 (d, J=8 Hz, 2H), 7.45 (m, 4H), 6.87 (t, J=8 Hz, 2H), 4.18 (t, J=6 Hz, 2H), 4.12 (t, J=5 Hz, 2H), 3.35 (m, 2H), 2.92 (t, J=5 Hz, 2H), 2.87 (s, 3H), 2.65 (br s, 4H), 2.34 (m, 2H), 2.16 (br s, 1H), 1.80 (br s, 6H).

Conversion to the oxalate was effected by dissolving the free base in EtOAc and adding a solution of oxalic acid in EtOAc. The resultant slurry was centrifuged, the supernatant was decanted, fresh EtOAc was added, and the process was repeated twice more. The solid product was dried in vacuo overnight.

Anal. calc'd for C$_{34}$H$_{36}$N$_2$O$_4$S·C$_2$H$_2$O$_4$·1.5H$_2$O: C, 63.05; H, 6.03; N, 4.08. Found: C, 62.88; H, 5.94; N, 4.01. FDMS 569 (M+1 for free base).

EXAMPLE 17

Preparation of 3-[3-Bromo-4-[4-(1-tetrazolyl)methyl] benzyl-6-hydroxy-2-[4-[2-(1-pyrrolidinyl)ethoxy]phenyl]-benzo[b]thiophene Oxalate Hydrate.

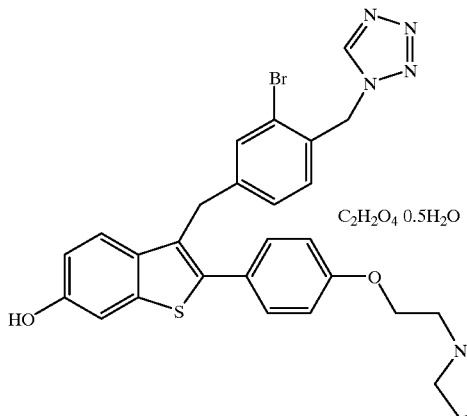

A. Methyl 3-Bromo-4-(bromomethyl)benzoate.

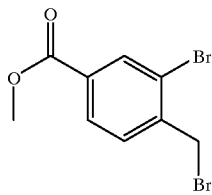

Methyl 3-bromo-4-methylbenzoate (23.3 g; 97 mmol) and 20.8 g (117 mmol) of NBS were combined in 210 mL of CCl$_4$ and heated to reflux. AIBN (0.8 g; 5.9 mmol) was added and the resultant mixture was heated at reflux for 4 h. After cooling to room temperature, the mixture was filtered and concentrated. The product (13.4 g; 43% yield) was isolated by flash chromatography on silica gel eluting with a gradient of 0–5% EtOAc/hexanes as a white crystalline solid.

$^1$H NMR (CDCl$_3$) δ 8.24 (s, 1H), 7.96 (d, J=8.0 Hz, 1H), 7.54 (d, J=8.0 Hz, 1H), 4.62 (s, 2H), 3.94 (s, 3H); FDMS 307 (M+); Anal. Calcd for C$_9$H$_8$Br$_2$O$_2$: C, 35.10; H, 2.62. Found: C, 34,99; H, 2.64.

B. Methyl 3-Bromo-4-(1-tetrazolylmethyl)benzoate.

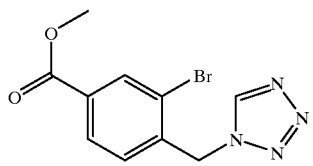

Methyl 3-bromo-4-(bromomethyl)benzoate (0.5 g; 1.62 mmol) was combined with tetrazole (0.11 g; 1.0 eq) and potassium carbonate (0.22g; 1.0 eq) in 3.0 mL of DMF in a flame-dried, argon-filled flask. The mixture was allowed to stir at room temperature overnight, then poured into water (80 mL). Extraction was carried out with EtOAc (4×50 mL), and the combined organics were washed with brine and dried by passage through Na$_2$SO$_4$. The title compound (0.28 g; 58% yield) was isolated by flash chromatography on silica gel, eluting with a gradient of hexanes (100–55%)/EtOAc (0–40%)/–Et$_3$N (0–5%).

$^1$H NMR (CDCl$_3$) δ 8.74 (s, 1H), 8.28 (s, 1H), 7.98 (d, J=8.0 Hz, 1H), 7.29 (d, J=7.9 Hz, 1H), 5.77 (s, 2H), 4.0 (s, 3H). Anal. calc'd for C$_{10}$H$_9$BrN$_4$O$_2$: C, 40.42; H, 3.05; N, 18.86. Found: C, 40.58; H, 3.06; N, 18.65. FDMS 296 (M).

C. 3-Bromo-4-[4-(1-tetrazolyl)methyl]phenyl 6-Methoxy-2-[4-[2-(1-pyrrolidinyl)ethoxy]phenyl]benzo[b]thiophen-3-yl Ketone.

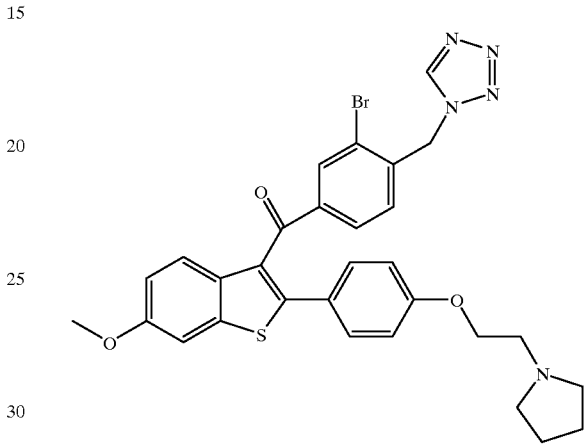

A mixture of methyl 3-bromo-4-(1-tetrazolylmethyl)-benzoate (0.26 g; 0.86 mmol) (Part B) in 3 mL of a solution of THF/methanol/H$_2$O (3:1:1 by volume) and LiOH (43 mg; 1.2 eq) was stirred at room temperature overnight. The mixture was concentrated under reduced pressure. The crude product was treated with oxalyl chloride (1.0 mL; excess) in 10 mL of 1,2-dichloroethane and 2 drops of DMF. The resultant mixture was stirred at room temperature overnight then concentrated under reduced pressure. The acid chloride so obtained was placed under high vacuum for 1 h, dissolved in dichloroethane (20 mL) then cooled in an ice-water bath (argon atmosphere). The mixture was treated with 6-methoxy-2-[4-[2-(1-pyrrolidinyl)ethoxy]phenyl]benzo[b]thiophene (0.20 g; 0.57 mmol) and AlCl$_3$ (0.46 g; 6.0 eq). Stirring was continued at 0° C. for 2.5 h, and then the mixture was poured into 80 mL of saturated aqueous NaHCO$_3$. After stirring for 1 h, extraction was carried out with EtOAc. The combined organics were washed with brine and dried by passage through NaSO$_4$. The product was isolated as a yellow foamy oil (0.28 g; 80% yield) by flash chromatography on silica gel, eluting with a gradient of hexanes (100–60%)/EtOAc (0–35%)/Et$_3$N (0–5%).

$^1$H NMR (CDCl$_3$) δ 8.51 (s, 1H), 7.91 (s, 1H), 7.82 (d, J=9.6 Hz, 1H), 7.61 (d, J=8.0 Hz, 1H), 7.35 (s, 1H), 7.20 (d, J=8.6 Hz, 2H), 7.06 (d, J=8.8 Hz, 1H), 7.00 (d, J=8.0 Hz, 1H), 6.73 (d, J=8.6 Hz, 2H), 5.63 (s, 2H), 4.05 (t, J=5.8 Hz, 2H), 3.91 (s, 3H), 2.93 (t, J=5.8 Hz, 2H), 2.62 (br s, 4H), 1.81 (br s, 4H). Anal. calc'd for C$_{30}$H$_{28}$BrN$_5$O$_3$S: C, 58.25; H, 4.56; N, 11.32. Found: C, 58.11; H, 4.76; U, 11.05. FDMS 618 (M+1).

D. 3-[3-Bromo-4-[4-(1-tetrazolyl)methyl]benzyl-6-methoxy-2-[4-[2-(1-pyrrolidinyl)ethoxy]phenyl]benzo[b]thiophene.

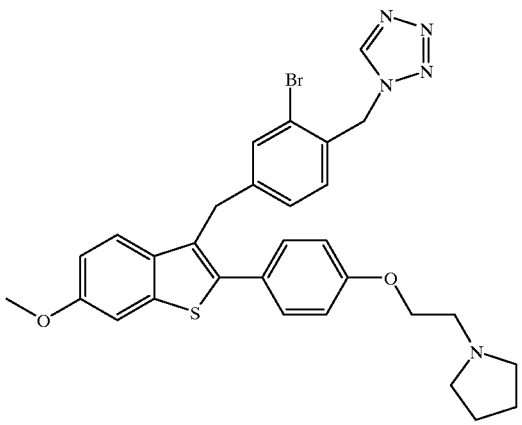

To the above ketone in THF was added LAH (1.5 mol/mol of ketone) at 0° C. The bath was removed and the mixture was stirred for 1 h. Hydrolysis was effected by addition of 1 mL of water, 1 mL of 5N NaOH, and 3 mL of water per gram of LAH, followed by stirring for 1 h. The mixture was filtered, the filtrate was concentrated, and the intermediate carbinol was dried in vacuo for 25 min. The carbinol was reduced using a method similar to that of the second step of Example 1-D. Thus, the carbinol was dissolved in methylene chloride under argon atmosphere and cooled in an ice-water bath. Triethylsilane was added, followed by dropwise addition of TFA. Upon completion of addition of TFA, the bath was removed and stirring was continued for 2 h. Saturated aqueous sodium bicarbonate (25 mL) was added, and extraction was carried out with EtOAc. The combined organics were washed with brine and dried by passage through sodium sulfate. The product was isolated in 63% yield by flash chromatography on silica gel eluting with a gradient of EtOAc (100–90%)/Et$_3$N (0–5%)/MeOH (0–5%).

$^1$H NMR (CDCl$_3$) δ 8.64 (s, 1H), 7.42 (s, 1H), 7.32 (m, 3H), 7.21 (d, J=8.0 Hz, 1H), 7.10 (d, J=8.0 Hz, 1H), 6.95 (m, 4H), 5.66 (s, 2H), 4.17 (m, 4H), 3.88 (s, 3H), 2.98 (t, J=5.8 Hz, 2H), 2.70 (br s, 4H), 1.86 (br s, 4H). FDMS 604 (M).

E. 3-[3-Bromo-4-[4-(1-tetrazolyl)methyl]benzyl-6-hydroxy-2-[4-[2-(1-pyrrolidinyl)ethoxy]phenyl]benzo[b]thiophene Oxalate Hydrate.

The compound of part D, above, was dissolved in dichloroethane (about 30 mL/g of ketone) under an argon atmosphere and cooled in an ice-water bath. To this was added ethanethiol (20 mmol/mmol ether) and aluminum chloride (10 mmol/mmol ether), and the mixture was stirred in the cold bath for 1 h. Brine was added to the mixture, and stirring was continued while warming to room temperature for 1 h. Extraction was carried out with dichloromethane. The combined organics were dried by passage through sodium sulfate. The title compound was isolated solid by flash chromatography on silica gel eluting with a gradient of EtOAc (100–85%)/Et$_3$N (0–5%)/MeOH (0–10%) in 78% yield.

$^1$-H NMR (CDCl$_3$) δ 8.63 (s, 1H), 7.39 (s, 1H), 7.04–7.25 (m, 6H), 6.85 (d, J=8.7 Hz, 1H), 6.76 (d, J=8.6 Hz, 2H), 5.64 (s, 2H), 4.16 (br s, 4H), 3.07 (m, 2H), 2.91 (br s, 4H), 1.93 (br s, 4H).

Conversion to the oxalate was effected as in Example 16.

Anal. calc'd for C$_{29}$H$_{28}$BrN$_5$O$_2$S.C$_2$H$_2$O$_4$.0.5H$_2$O: C, 53.87; H, 4.52; N, 10.13. Found: C, 53.87; H, 4.56; N, 10.11. FDMS 590 (M+1 for free base).

The 6-methoxy-2-[4-[2-(1-pyrrolidinyl)ethoxy]phenyl]-benzo[b]thiophene used in part C, above, may be obtained as follows.

F. 6-Methoxybenzo[b]thiophene-2-boronic Acid.

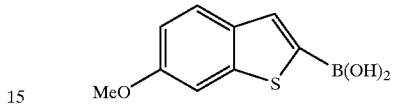

To a solution of 6-methoxybenzo[b]thiophene (Graham, S. L., et al. J. Med. Chem. 1989, 32, 2548–2554)(18.13 g, 0.111 mol) in 150 mL of anhydrous THF at −60° C. was added n-BuLi (76.2 mL, 0.122 mol, 1.6 M solution in hexanes), dropwise via syringe. After stirring for 30 min, triisopropyl borate (28.2 mL, 0.122 mol) was introduced via syringe. The resulting mixture was allowed to gradually warm to 0° C. and then partitioned between 1.0 N HCl and EtOAc (300 mL each). The layers were separated, and the organic phase was dried over Na$_2$SO$_4$. Concentration in vacuo produced a white solid that was triturated from Et$_2$O/hexanes. Filtration provided 16.4 g (71%) of 6-methoxybenzo[b]thiophene-2-boronic acid as a white solid.

mp 200° C. (dec); FDMS 208 (M$^+$; 100); $^1$H NMR (DMSO-d$_6$) δ 8.36 (br s), 7.86–7.75 (m, 2H), 7.53 (dd, J=8.1 and 2.0 Hz, 1H), 6.98 (m, 1H), 3.82 (s, 3H).

G. 6-Methoxy-2-[4-(2-(1-pyrrolidinyl)ethoxy]phenyl]-benzo[b]thiophene.

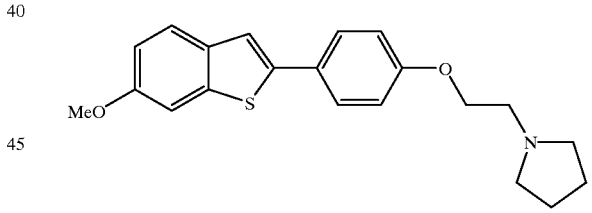

To a slurry of 6-methoxybenzo[b]thiophene-2-boronic acid (6.43 g, 30.9 mmol) in 310 mL of benzene was added 1-(2-(4-bromophenoxy)ethyl)pyrrolidine (5.80 mL, 28.1 mmol). Upon addition the reaction mixture turned to a yellow homogeneous solution. The reaction flask was then covered with aluminum foil to keep out light. To this was added 1.07 g (0.92 mmol) of tetrakis(triphenylphosphine)-palladium(0), followed by 30 mL of 2.0 N sodium carbonate solution. The biphasic mixture was heated at 85° C. for 3 h with vigorous stirring. The mixture was cooled to 0° C. and 175 mL of brine solution was added. The layers were separated and the aqueous layer was extracted with 1.0 L of EtOAc. The combined organic layers were dried over MgSO$_4$ and concentrated under reduced pressure. The residue was purified by PrepLC (53:35:2 THF-hexanes-TEA) to afford 5.42 g (15.3 mmol, 55%) of an off-white solid.

mp 151–154° C.; ¹H NMR (CDCl₃) δ 7.61 (d, J=8.8 Hz, 1H), 7.58 (d, J=8.8 Hz, 2H), 7.33 (s, 1H), 7.29 (d, J=2.3 Hz, 1H), 6.95 (d, J=8.7 Hz, 3H), 4.18 (t, J=5.9 Hz, 2H), 3.88 (s, 3H), 2.97 (t, J=5.9 Hz, 2H), 2.71 (br t, 4H), 1.85 (m, 4H); FDMS: 353 (M+); Anal. Calcd for $C_{21}H_{23}NO_2S$: C, 71.36; H, 6.56; N, 3.96. Found: C, 71.58; H, 6.35; N, 3.91.

EXAMPLE 18

Preparation of 1-[2-[4-[3-[4-(Cyclopentylmethyl)benzyl-6-hydroxy]benzo[b]thiophen-2-yl]phenoxy]ethyl]pyrrolidine Oxalate.

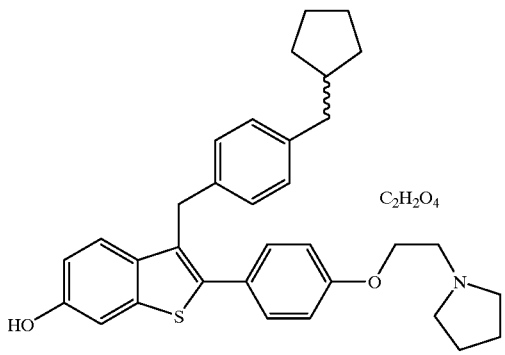

A. Methyl 4-Cyclopentylmethylbenzoate.

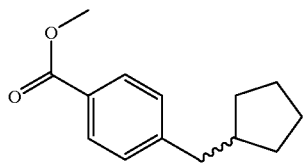

Methyl 4-bromomethylbenzoate (1.4 g; 6.11 mmol) and triethyl phosphite (1.05 mL; 1 eq) were combined and heated in an oil bath maintained at 125–135° C. overnight. The crude product was maintained in vacuo overnight, then used without purification. The crude phosphonate was dissolved in anhydrous THF (25 mL) under Ar, and NaNH₂ (0.3 g; 1.3 eq) was added. The mixture was stirred for 1.5 h, then cyclopentanone (0.57 mL; 1 eq) was added. Stirring was continued for 2 h. The reaction mixture was diluted with brine and extracted with $CH_2Cl_2$. The combined organics were dried by passage through $Na_2SO_4$, and concentrated under reduced pressure. The alkene was reduced by catalytic hydrogenation in THF using 5% Pd on charcoal catalyst at an initial pressure of 4.1 bar at room temperature overnight. The title compound 0.35 g (22% yield overall) was purified by flash chromatography on silica gel, eluting with a gradient of hexanes (100–85%)/EtOAc (0–15%). The product is actually a mixture of methyl and ethyl esters, probably formed during the initial treatment with triethyl phosphite. The esters were not separated by chromatography.

¹H NMR (CDCl₃) δ 7.95 (d, J=8.1, 2H), 7.24 (d, J=8.0, 2H), 4.37 (q, J=7.1, ethyl ester), 3.90 (s, methyl ester), 2.65 (d, J=7.4 Hz, 2H), 2.09 (m, 1H), 1.59–1.72 (m, 4H), 1.49–1.59 (m, 2H), 1.38 (t, J=7.1 Hz, ethyl ester), 1.89 (m, 2H). FDMS 218 (M for methyl ester) and 232 (M for ethyl ester).

B. 4-(Cyclopentylmethyl)phenyl 6-Methoxy-2-[4-[2-(1-pyrrolidinyl)ethoxy]phenyl]benzo[b]thiophen-3-yl Ketone.

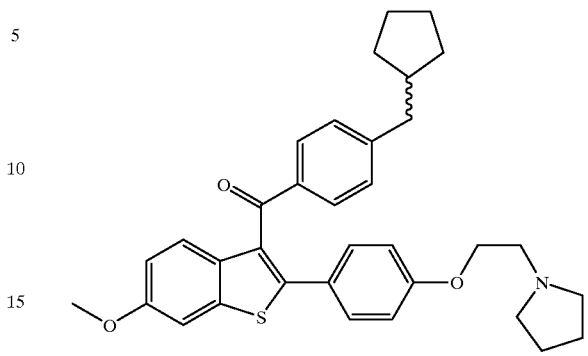

Following essentially the procedure of Example 17-C, methyl 4-cyclopentylmethylbenzoate (Part A) was converted to its acid chloride and combined with 6-methoxy-2-[4-[2-(1-pyrrolidinyl)ethoxy]phenyl]benzo[b]thiophene (0.20 g; 0.57 mmol) to form the title compound in 21% yield.

¹H NMR (CDCl₃) δ 7.67 (d, J=8.0 Hz, 2H), 7.62 (d, J=8.9, 1H), 7.32 (m, 3H), 7.05 (d, J=8.1 Hz, 2H), 6.97 (d, J=8.9 Hz, 1H), 6.74 (d, J=8.7 Hz, 2H), 4.02 (t, J=6.0 Hz, 2H), 3.90 (s, 3H), 2.85 (t, J=6.0 Hz, 2H), 2.58 (m, 6), 2.03 (m, 1H), 1.81 (br s, 4), 1.66–1.47 (m, 6), 1.10 (m, 2H).

C. 1-[2-[4-[3-[4-(Cyclopentylmethyl)benzyl-6-methoxy]-benzo[b]thiophen-2-yl]phenoxy]ethyl]pyrrolidine.

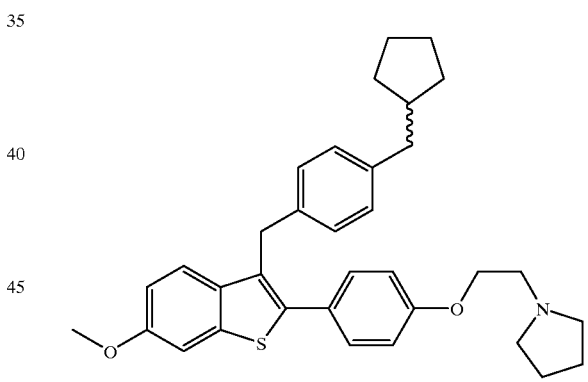

Following essentially the procedure of Example 17-D, the title compound was produced from the ketone from Part B in 64% yield. The product was isolated by flash chromatography on silica gel eluting with a gradient of EtOAc (100–90%)/Et₃N (0–5%)/MeOH (0–5%).

¹H NMR (CDCl₃) δ 7.42–7.26 (m, 4H), 7.04 (s, 4H), 6.92 (m, 3H), 4.19 (s, 2H), 4.13 (t, J=6.0 Hz, 2H), 3.86 (s, 3H), 2.92 (t, J=5.9 Hz, 2H), 2.63 (br s, 4H), 2.55 (d, J=7.4 Hz, 2H), 2.05 (m, 1H), 1.82 (br s, 4H), 1.80–1.49 (m, 6H), 1.18 (m, 2H).

D. 1-[2-[4-[3-[4-(Cyclopentylmethyl)benzyl-6-hydroxy]-benzo[b]thiophen-2-yl]phenoxy]ethyl]pyrrolidine Oxalate Following essentially the procedure of Example 17-E, the title compound was prepared from the compound of part C in 29% yield.

$^1$H NMR (CDCl$_3$) δ 7.27 (m, 4H), 7.01 (s, 4H), 6.75 (m, 3H), 4.12 (m, 4H), 3.00 (t, J=6.0 Hz, 2H), 2.86 (br s, 4H), 2.53 (d, J=7.5 Hz, 2H), 2.03 (m, 1H), 1.88 (br s, 4H), 1.8–1.4 (m, 6H), 1.18 (m, 2H). FDMS 512 (M+1).

Conversion to the oxalate was effected as in Example 16.

EXAMPLE 19

Preparation of 2-[4-[2-(1-Pyrrolidinyl)ethoxy]phenyl]-benzo[b]thiophen-3-yl 4-[2-(2-Oxopyrrolidin-1-yl)ethoxy]phenyl Ketone.

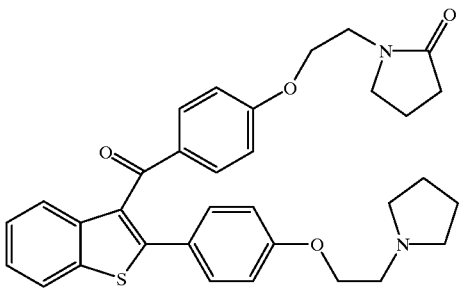

Sodium hydride (60% oil dispersion, 50 mg) was suspended in DMF (2.0 mL) and stirred at ambient temperature for 15 min under argon before 1-(2-hydroxyethyl)-2-pyrrolidinone (87 μL) was added. After stirring for 15 min, 4-fluorophenyl 2-[4-[2-(1-pyrrolidinyl)ethoxy]phenyl]-benzo[b]thiophen-3-yl ketone (223 mg) in 1 mL of DMF was introduced and the resulting solution was stirred at ambient temperature for 3.5 h. The reaction mixture was diluted with brine (50 mL) and extracted with EtOAc (3×50 mL). The combined organic layers were dried (Na$_2$SO$_4$) and concentrated under reduced pressure. Chromatography with Et$_3$N:MeOH:EtOAc (5:5–10:90–85) afforded the product as a colorless oil (210 mg).

$^1$H NMR (CDCl$_3$): δ 7.85 (m, 1H), 7.78 (d, 2H), 7.65 (m, 1H), 7.35 (d, 2H), 7.24 (m, 2H), 6.80 (d, 2H), 6.74 (d, 2H), 4.14 (t, 2H), 4.04 (t, 2H), 3.65 (t, 2H), 3.52 (m, 2H), 2.85 (t, 2H), 2.61 (m, 4H), 2.38 (m, 2H), 2.03 (m, 2H), 1.78 (m, 4H).

EXAMPLE 20

Preparation of 3-[4-[2-(2-Oxopyrrolidin-1-yl)ethoxy]benzyl]-2-[4-[2-(1-pyrrolidinyl)ethoxy]phenyl]benzo[b]thiophene.

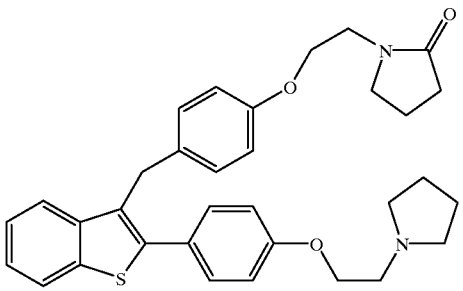

2-[4-[2-(1-Pyrrolidinyl)ethoxy]phenyl]benzo[b]thiophen-3-yl 4-[2-(2-oxopyrrolidin-1-yl)ethoxy]phenyl ketone (120 mg) was dissolved in THF/MeOH (3.0/0.3 mL) and treated with lithium borohydride (40 mg) in one portion and allowed to stir at ambient temperature for 4 h. The reaction mixture was diluted with brine (30 mL) and extracted with dichloromethane (20 mL×3). The combined organic layers were dried with sodium sulfate and concentrated in vacuo to give the crude alcohol. This material was dissolved in dichloromethane (3.0 mL), treated with triethylsilane (0.25 mL) and trifluoroacetic acid (0.2 mL) sequentially, allowed to stir at ambient temperature for 2 h, and concentrated under reduced pressure. The residue was extracted with -dichloromethane (20 mL×3) from saturated aqueous sodium bicarbonate (30 mL). The combined organic layers were dried with sodium sulfate and concentrated. Chromatography with Et$_3$N:MeOH:EtOAc (5:5:90) afforded the title compound (27 mg).

FDMS m/e: found 541 (M+H$^+$); $^1$H NMR(CDCl$_3$): δ 7.82 (m, 1H), 7.46 (m, 1H), 7.41 (d, 2H), 7.25 (m, 2H), 7.05 (d, 2H), 6.94 (d, 2H), 6.77 (d, 2H), 4.21 (s, 2H), 4.16 (t, 2H), 4.04 (t, 2H), 3.63 (t, 2H), 3.58 (t, 2H), 2.96 (t, 2H), 2.62 (m, 4H), 2.38 (t, 2H), 2.01 (m, 2H), 1.82 (m, 4H).

EXAMPLE 21

Preparation of 3-[4-(1-Pyrrolidinylcarbonyl)benzyl]-2-[4-[2-(1-pyrrolidinyl)ethoxy]phenyl]benzo[b]thiophene.

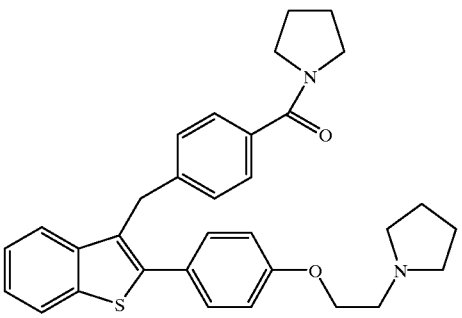

3-(4-Bromobenzyl)-2-[4-[2-(1-pyrrolidinyl)ethoxy]phenyl]benzo[b]thiophene (178 mg, 0.36 mmol) was dissolved in DMF (2.0 mL) and treated with pyrrolidine (0.3 mL). The solution was purged with carbon monoxide for 5 min at 80° C. before the catalyst dichlorobis (triphenylphosphine)palladium (10 mg) was added. The reaction mixture was allowed to stir under a balloon of carbon monoxide at 80° C. for 4 h, then diluted with brine (30 mL) and extracted with EtOAc (20 mL×3). The combined organic layers were dried with sodium sulfate and concentrated. Chromotography with Et$_3$N:MeOH:EtOAc (5:5:90) afforded the product (16 mg) along with recovered starting material (140 mg). FDMS m/e: found 511 (M+H$^+$); $^1$H NMR (CDCl$_3$): δ 7.97 (d, 1H), 7.57 (m, 1H), 7.55 (d, 2H), 7.50 (m, 1H), 7.40 (m, 1H), 7.39 (d, 2H), 7.24 (d, 2H), 7.03 (d, 2H), 4.40 (s, 2H), 4.28 (t, 2H), 3.76 (t, 2H), 3.57 (t, 2H), 3.10 (t, 2H), 2.82 (m, 4H), 2.01 (m, 4H), 1.98 (m, 4H).

EXAMPLE 22

Preparation of 6-Hydroxy-3-[3-methoxy-4-[(2-oxopyrrolidin-1-yl)methyl]benzyl]-2-[4-[2-(1-pyrrolidinyl)ethoxy]phenyl]-benzo[b]thiophene Oxalate.

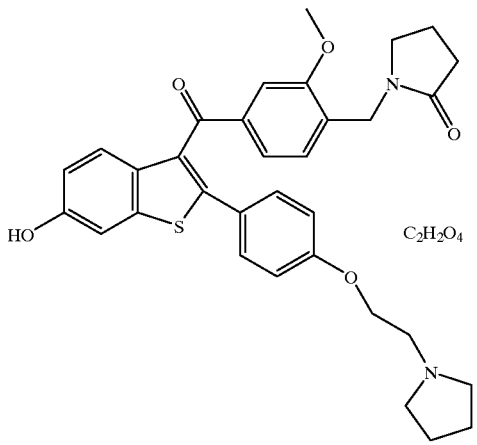

A. 1-Bromo-4-[2-(t-butyldimethylsilyloxy)ethoxy]benzene.

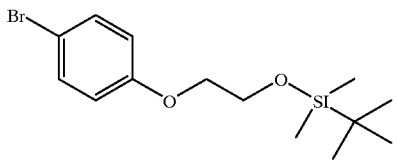

To a solution of 2-(4-bromophenoxy)ethanol (10.94 g, 50.4 mmol), in dry DMF (50 mL), was added t-butyldimethyl-silyl chloride (7.6 g, 50.4 mmol) and imidazole (3.77 g 55.5 mmol). The reaction was stirred at ambient temperature for 18 h, then partitioned with hexane (300 mL) and water (300 mL). The aqueous layer was extracted with hexane (3×100 mL). The combined organic extracts were dried (MgSO$_4$) and the solvent removed under reduced pressure to give the desired product as an oil (16.6 g, 99%).

$^1$H NMR (CDCl$_3$) δ 7.37 (d, J=8.6 Hz, 2H), 6.80 (d, J=8.6 Hz, 2H), 4.00 (t, J=6.0 Hz, 2H), 3.98 (t, J=6.0 Hz, 2H), 0.91 (s, 6H), 0.10 (s, 9H).

B. 6-Benzyloxy-2-[4-[2-(t-butyldimethylsilyloxy)ethoxy]phenyl]benzo[b]thiophen-3-yl 3-Methoxy-4-[(1-pyrrolidinyl)-methyl]phenyl Ketone.

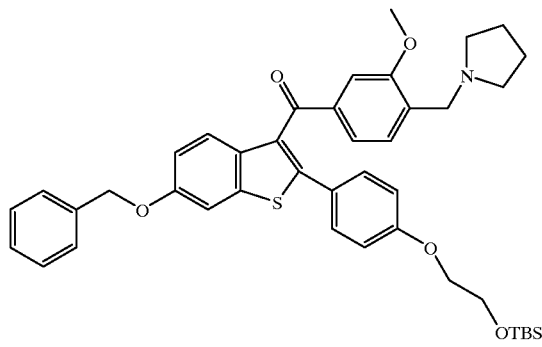

The above bromide (1.25 g, 3.39 mmol), in THF (1.5 mL), was added to a mixture of THF (1.5 mL) and Mg°. The material was stirred at 60° C. for 1 h, during which time the Mg° dissolved. This solution was then added, via syringe, to a THF (5 mL) solution of 6-benzyloxy-2-(dimethylamino)-benzo[b]thiophen-3-yl 3-methoxy-4-[(1-pyrrolidinyl)methyl]-phenyl ketone (1.1 g, 2.26 mmol). After 1 h, the solution was diluted 25 fold with EtOAc, the organics washed with saturated NH$_4$Cl solution and concentrated under reduced pressure. Material was purified by flash chromatography (SiO$_2$, 10% MeOH in CHCl$_3$); yielding 827 mg (50%).

$^1$H NMR (CDCl$_3$) δ 7.63 (d, J=8.7 Hz, 1H), 7.49 (d, J=4.3 Hz, 2H), 7.21–7.43 (m, 8H), 7.15 (dd, J=2.1, 8.7 Hz, 1H), 6.95 (d, J=6.4 Hz, 1H), 6.75 (d, J=8.7 Hz, 2H), 5.17 (s, 2H), 3.90–4.0 (m, 4H), 3.80 (s, 3H), 3.65 (s, 2H), 2.55 (s, 4H), 1.90 (s, 4H), 0.95 (s, 9H), 0.15 (s, 6H).

C. 6-Benzyloxy-2-[4-[2-(t-butyldimethylsilyloxy)ethoxy]-phenyl]benzo[b]thiophen-3-yl 3-Methoxy-4-[(2-oxopyrrolidin-1-yl)methyl]phenyl Ketone.

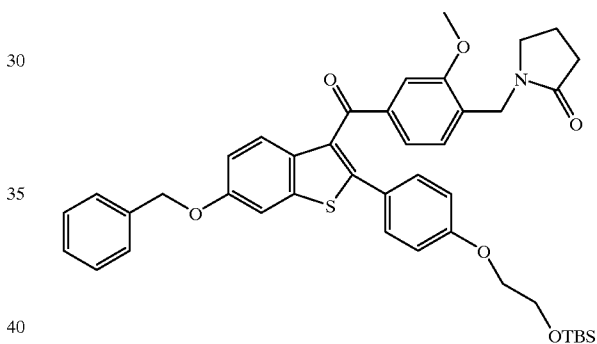

A solution of the above amine (147 mg, 0.219 mmol) in CHCl$_3$ (1 mL) was added to a solution of cyanogen bromide (26 mg, 0.241 mmol) in CHCl$_3$ (1 mL). After completion of the reaction, as indicated by TLC, the mixture was diluted 25 fold with EtOAc, the organics washed with saturated NaHCO$_3$ solution and H$_2$O, and concentrated under reduced pressure. To this crude residue was added the sodium salt of 2-pyrrolidinone (149 mg, 1.09 mmol, pre-formed from an equimolar amount of NaH in 1 mL of THF) and the mixture stirred at 60° C. for 35 min. After diluting 25 fold with EtOAc, the organics were washed with saturated NaHCO$_3$ solution, H$_2$O, and concentrated under reduced pressure. Material was purified by flash chromatography (SiO$_2$, 20% Hexane in EtOAc); yielding 150 mg (94%).

$^1$H NMR (CDCl$_3$) δ 7.59 (d, J=8.7 Hz, 1H), 7.22–7.47 (m, 10H), 7.05 (dd, J=2.3, 8.7 Hz, 1H), 6.98 (d, J=7.9 Hz, 1H), 6.74 (d, J=8.7 Hz, 2H), 5.15 (s, 2H), 4.43 (s, 2H), 3.83–3.96 (m, 4H), 3.78 (s, 3H), 3.17 (t, J=7.9 Hz, 2H), 2.39 (t, J=7.9 Hz, 2H), 1.94–2.01 (m, 2H), 1.66 (s, 2H), 0.89 (s, 9H), 0.07 (s, 6H); FDMS 721.5.

D. 6-Benzyloxy-2-[4-1[2-(1-pyrrolidinyl)ethoxy]phenyl]-enzo[b]thiophen-3-yl 3-Methoxy-4-[(2-oxopyrrolidin-1-yl)-methyl]phenyl Ketone.

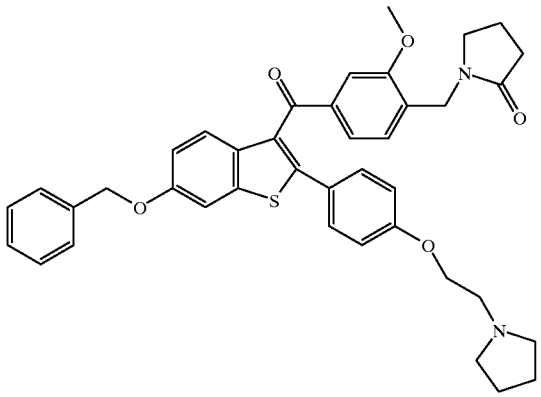

To the above silyl ether (0.195 mg, 0.258 mmol) in THF (1 mL) was added 1.0 M TBAF (0.28 mL, 0.28 mmol) and the mixture stirred at room temperature for 45 min. After diluting 50 fold with EtOAc, the organics were washed with H$_2$O and concentrated under reduced pressure. The resulting residue was purified by flash chromatography (SiO$_2$, 5% MeOH in EtOAc). This compound was then taken up in pyridine (0.5 mL) and methanesulfonyl chloride (42 mg, 0.368 mmol) added. The mixture was stirred, under N$_2$, for 35 min and then pyrrolidine (348 mg, 4.9 mmol) added and the solution heated at 60° C. for 45 min. After cooling, the mixture was diluted 50 fold with EtOAc and the organics washed with saturated NaHCO$_3$ and H$_2$O and concentrated under reduced pressure. Material was purified by flash chromatography (SiO$_2$, 15% MeOH in EtOAc, 1% Et$_3$N v/v added); yielding 138 mg (81%) of the pyrrolidino compound.

$^1$H NMR (CDCl$_3$) δ 7.60 (d, J=8.9 Hz, 1H), 7.23–7.47 (m, 10H), 7.06 (dd, J=2.4, 9.0 Hz, 1H), 6.98 (d, J=7.8 Hz, 1H), 6.75 (d, J=8.2 Hz, 2H), 5.14 (s, 2H), 4.43 (s, 2H), 4.07 (t, J=5.7 Hz, 2H), 3.78 (s, 3H), 3.20 (t, J=7.1 Hz, 2H), 2.91 (t, J=6.6 Hz, 2H), 2.67 (s, 4H), 2.39 (t, J=8.1 Hz, 2H), 1.97 (t, J=7.1 Hz, 2H), 1.83 (s, 4H); FDMS 661 (M+1).

E. 6-Hydroxy-3-[3-methoxy-4-[(2-oxopyrrolidin-1-yl)-methyl]benzyl]-2-[4-[2-(1-pyrrolidinyl)ethoxy]phenyl]-benzo[b]thiophene Oxalate.

To the above benzyl ether (36 mg, 0.054 mmol) was added aqueous ammonium formate (0.25 mL of 25% w/v), THF (0.25 mL), and Pd/C (10%, 36 mg). The mixture was rapidly stirred at room temperature for 2 h and then diluted 25 fold with THF and passed through a pad of diatomaceous earth. The filtrate was concentrated under reduced pressure and the resulting residue purified by flash chromatography (SiO$_2$, 10% MeOH in CHCl$_3$). The oxalate salt was prepared according to the procedure described in Example 16, yielding 16 mg (45%) of the title compound.

$^1$H NMR δ 7.56 (d, J=8.4 Hz, 1H), 7.35 (s, 1H), 7.27 (s, 1H), 7.22 (d, J=8.5 Hz, 1H), 7.15 (d, J=8.6 Hz, 1H), 6.96 (d, J=7.8 Hz, 1H), 6.88 (d, J=9.2 Hz, 2H), 6.60 (d, J=8.6 Hz, 2H), 4.43 (s, 2H), 4.06 (t, J=4.5 Hz, 2H), 3.77 (s, 3H), 3.18 (t, J=7.2 Hz, 2H), 2.97 (t, J=4.7 Hz, 2H), 2.81 (s, 4H), 2.42 (t, J=8.1 Hz, 2H), 1.98 (t, J=7.3 Hz, 2H), 1.87 (s, 4H); FAB MS 571.3 (M+1).

The 6-benzyloxy-2-(dimethylamino)benzo[b]thiophen-3-yl 3-methoxy-4-[(1-pyrrolidinyl)methyl]phenyl ketone for part B, above, may be obtained as follows.

F. Methyl 3-methoxy-4-[(1-pyrrolidinyl)methyl]benzoate.

Methyl 3-bromo-4-(bromomethyl)benzoate (Example 17-A) in anhydrous dichloromethane at 0° C. is treated with excess pyrrolidine (more than two molar equivalents), allowed to warm to room temperature and stirred 2 h. The reaction mixture is diluted with EtOAc, washed with half-saturated aqueous NaHCO$_3$, dried (MgSO$_4$), evaporated and chromatographed on silica [gradient 0–10% EtOH/Et$_3$N (2/1) in THF/hexanes (1/1)] to provide the pyrrolidinyl ester as an oil.

IR (CHCl$_3$) 2954, 1716 cm$^{-1}$; $^1$H NMR (CDCl$_3$) δ 1.95 (br s, 4H), 2.89 (br s, 4H), 3.91 (s, 3H), 3.92 (s, 3H), 3.98 (br t, J=6.8 Hz, 2H), 7.56 (s, 1H), 7.61–7.67 (m, 2H); FDMS m/e 249 (M+).

G. 6-Benzyloxy-2-(dimethylamino)benzo[b]thiophen-3-yl 3-Methoxy-4-[(1-pyrrolidinyl)methyl]phenyl Ketone.

Using a procedure similar to that described above in Example 17-B, the above ester is hydrolysed to the benzoic acid. Using procedures similar to those described above in Example 1-A, the acid is then converted into the benzoyl chloride hydrochloride which is used to acylate 6-benzyloxy-2-(dimethylamino)benzo[b]thiophene.

EXAMPLE 23

Preparation of 6-Hydroxy-3-[3-methoxy-4-[2-oxopyrrolidin-1-yl)methyl]benzyl]-2-[4-[2-(1-pyrrolidinyl)ethoxy]phenyl]-benzo[b]thiophene Oxalate.

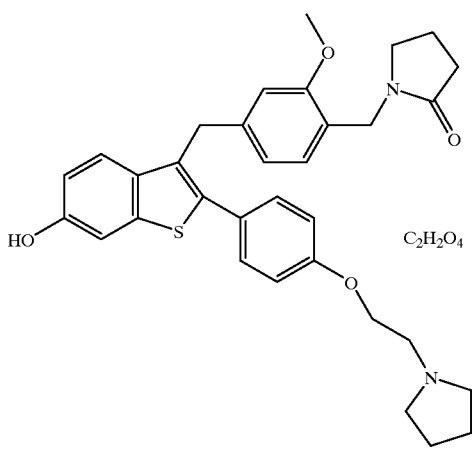

A. 6-Benzyloxy-3-[3-methoxy-4-[(2-oxopyrrolidin-1-yl)-methyl]benzyl]-2-[4-[2-(1-pyrrolidinyl)ethoxy]phenyl]-benzo[b]thiophene Oxalate

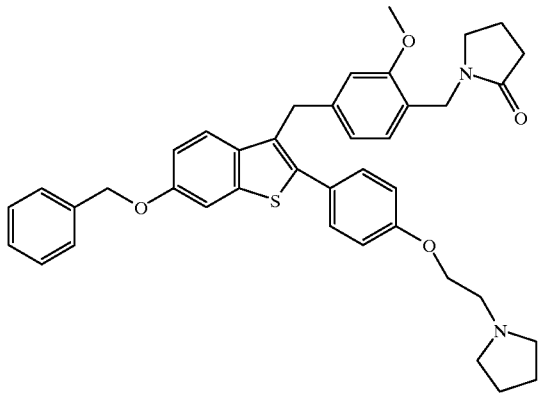

To the ketone (Example 22-D, 91 mg, 0.137 mmol) in CH$_2$Cl$_2$ (2 mL) at 0° C. and under N$_2$, was added a solution of DIBAL-H (1.0 M, 0.42 mL, 0.414 mmol) in toluene. The mixture was stirred for 55 min and then quenched with MeOH (0.25 mL). Saturated Rochelle's salt (15 mL) and EtOAc (35 mL) were then added. The bi-layer solution was stirred at room temperature for 1 h and then the organic layer concentrated under reduced pressure. After taking the resulting residue up in CH$_2$Cl$_2$ (2 mL), the material was treated sequentially with Et$_3$SiH (0.15 mL, 0.959 mmol) and TFA (0.11 mL, 1.37 mmol) at 0° C. and under N$_2$. The solution was stirred for 1 h and then diluted 25 fold with EtOAc and the organics washed with saturated NaHCO$_3$ solution and H$_2$O. The organics were then concentrated under reduced pressure and purified by flash chromatography (SiO$_2$, 10% MeOH in CHCl$_3$); yielding 38 mg (43%) of the benzyl compound.

$^1$H NMR (CDCl$_3$) δ 7.36–7.48 (m, 9H), 6.94–7.05 (m, 4H), 6.70 (d, J=7.1 Hz, 1H), 6.66 (s, 1H), 5.13 (s, 2H), 4.44 (s, 2H), 4.21 (s, 2H), 4.16 (t, J=6.8 Hz, 2H), 3.70 (s, 3H), 3.29 (t, J=7.1 Hz, 2H), 2.95 (t, J=6.9 Hz, 2H), 2.67 (s, 4H), 2.41 (t, J=7.8 Hz, 2H), 2.01 (m, 2H), 1.84 (s, 4H); FDMS 647.1 (M+1).

B. 6-Hydroxy-3-[3-methoxy-4-[(2-oxopyrrolidin-1-yl)-methyl]benzyl]-2-[4-[2-(1-pyrrolidinyl)ethoxy]phenyl]-benzo[b]thiophene Oxalate.

The title compound was prepared in 41% yield from the above benzyl ether by essentially following the procedure detailed in Example 22-E.

$^1$H NMR (CDCl$_3$) δ 7.22–7.32 (m, 4H), 6.97 (d, J=8.0 Hz, 2H), 6.87 (dd, J=2.1, 8.6 Hz, 1H), 6.62–6.68 (m, 3H), 4.42 (s, 2H), 4.19 (t, J=4.7 Hz, 2H), 4.12 (s, 2H), 3.65 (s, 2H), 3.28–3.32 (m, 4H), 3.26 (s, 4H), 2.41 (t, J=8.0 Hz, 2H), 2.03 (s, 4H), 1.96–2.01 (m, 2H); FAB MS 557.3 (M +1)

EXAMPLE 24

Preparation of 3-[4-(2-Hydrazino-2-oxoethoxy)benzyl]-2-[4-[2-(1-pyrrolidinyl)ethoxy]phenyl]benzo[b]thiophene.

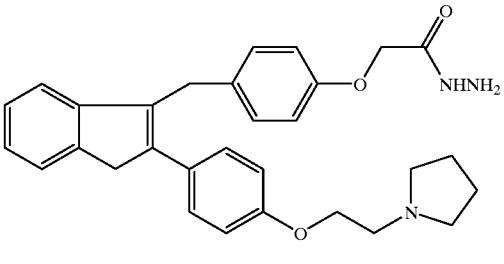

A mixture of 3-[4-(2-ethoxy-2-oxoethoxy)benzyl]-2-[4-[2-(1-pyrrolidinyl)ethoxy]phenyl]benzo[b]thiophene (400 mg), hydrazine hydrate (2 mL), and EtOH (50 mL was refluxed for 3.5 hours, cooled, and evaporated in vacuo to give the title compound as an amorphous solid (0.4 g, 100%).

FDMS 502.1 (M+)

Analysis for C$_{29}$H$_{31}$N$_3$O$_3$S: Calcd: C, 69.44; H, 6.23; N, 8.38; Found: C, 69.17; H, 6.23; N, 8.51.

The 3-[4-(2-ethoxy-2-oxoethoxy)benzyl]-2-[4-[2-(1-pyrrolidinyl)ethoxy]phenyl)benzo[b]thiophene may be obtained as follows:

A. 2-(4-Hydroxyphenyl)benzo[b]thiophen-3-yl 4-Methoxyphenyl Ketone.

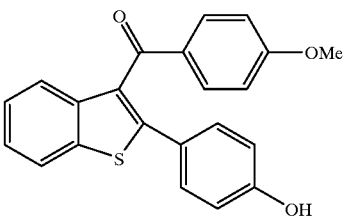

To a solution of 10.0 g (26.7 mmol) of 2-(4-methoxyphenyl)benzo[b]thiophen-3-yl 4-methoxyphenyl ketone in 400 mL of CH$_2$Cl$_2$ at −10° C. was added dropwise 107 mL of a 1.0 M solution of BBr$_3$ in CH$_2$Cl$_2$. After complete addition, the reaction was stirred at −10° C. for 1 h and was quenched by the careful addition of 75 mL of MeOH. The mixture was allowed to warm to room temperature and was stirred at ambient temperature for 2 h. Evaporation of the volatiles in vacuo afforded a deep red oil which was taken up in 250 mL of EtOAc. The solution was then washed sequentially with saturated aq NaHCO$_3$ (2×200 mL), H$_2$O (200 mL) and brine (200 mL), dried over Na$_2$SO$_4$, and concentrated in vacuo to give 9.85 g of a red oil which was purified by flash chromatography (SiO$_2$; 25% EtOAc in hexanes) to afford 8.69 g (24.1 mmol; 90%) of the title compound as a light yellow solid.

FDMS 360 (M$^+$; 100).

B. 2-[4-[2-(1-Pyrrolidinyl)ethoxy]phenyl]benzo[b]thiophen-3-yl 4-Methoxyphenyl Ketone.

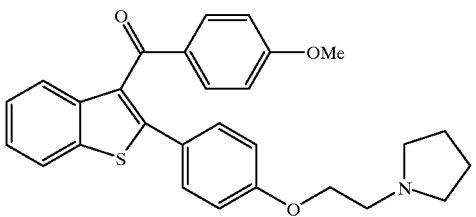

Using 1-(2-chloroethyl)pyrrolidine hydrochloride (about 3 mmol/mmol of phenol) as the alkylating agent and $Cs_2CO_3$ (about 4 mmol/mmol of phenol) as the base, a solution of 2-(4-hydroxyphenyl)benzo[b]thiophen-3-yl 4-methoxyphenyl ketone (Part A) (about 44 mM in DMF) was heated at 80° C. for 6 h. After the reaction mixture was cooled and filtered, it was partitioned between water and EtOAc. Following drying ($K_2CO_3$) and evaporation of the organic phase, the title compound was obtained as an oil in 80% yield following flash chromatography ($SiO_2$; 2.5% MeOH in $CH_2Cl_2$).

FDMS 457 ($M^+$; 100); Anal. Calcd for $C_{28}H_{27}NO_3S$: C, 73.49; H, 5.95; N, 3.06. Found: C, 73.19 ; H, 5.96; N, 3.02.

C. 2-[4-[2-(1-Pyrrolidinyl)ethoxy]phenyl]benzo[b]thiophen-3-yl 4-Hydroxyphenyl Ketone.

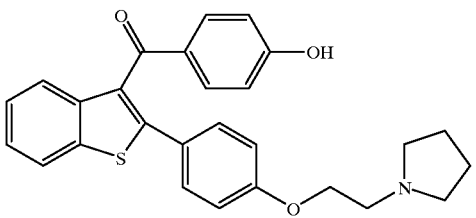

A solution of 1.90 g (4.15 mmol) of 2-[4-[2-(1-pyrrolidinyl)ethoxy]phenyl)benzo[b]thiophen-3-yl 4-methoxyphenyl ketone (Part B) in 50 mL of DMF was treated with 0.7 g (8.30 mmol) of sodium thioethoxide at 80° C. for 1 h. The mixture was cooled, filtered, and concentrated in vacuo. The residue was taken up in 100 mL of $CH_2Cl_2$ and was transferred to a separatory funnel containing 200 mL of $H_2O$. The aqueous layer was adjusted to pH 8 with 5.0 N aq HCl and the contents were shaken well. The two layers were separated and the aqueous layer was extracted with EtOAc. The combined organic layers were dried over $K_2CO_3$ and evaporated to give a yellow solid which was triturated with EtOAc to afford 1.40 g of the title compound as a yellow solid.

FDMS 443 ($M^+$; 100).

D. 3-(4-Hydroxybenzyl)-2-[4-[2-(1-pyrrolidinyl)ethoxy]-phenyl]benzo[b]thiophene.

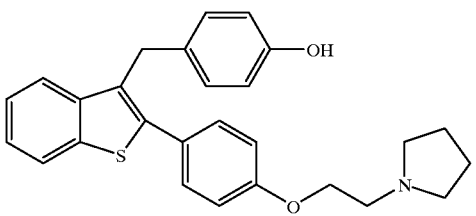

By using procedures similar to those detailed in Example 17, Part D, the title compound was prepared in 51% yield as a white solid.

FDMS 429 ($M^+$; 100).

E. 3-[4-(2-Ethoxy-2-oxoethoxy)benzyl]-2-[4-[2-(1-pyrrolidinyl)ethoxy]phenyl]benzo[b]thiophene Hydrochloride.

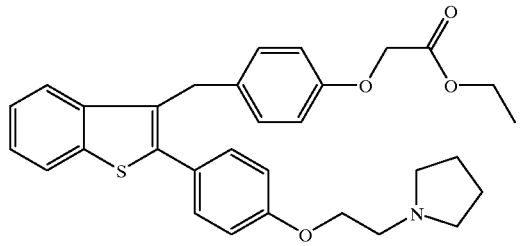

A solution of 3-(4-hydroxybenzyl)-2-[4-[2-(1-pyrrolidinyl)ethoxy]phenyl]benzo[b]thiophene in DMF (70 mL) was treated with sodium hydride (100 mg, 60% in mineral oil, 2.5 mmol) for 10 minutes and then with ethyl bromoacetate (0.3 mL, 2.7 mmol) for 20 minutes. The mixture was diluted with EtOAc and water. The organic phase was washed with water, washed with brine, dried over sodium sulfate, and evaporated in vacuo. The residue was chromatographed on silica gel, eluting with a gradient (0–4% MeOH/$CH_2Cl_2$), to give the product free base as an oil (860 mg, 82%). The hydrochloride salt was precipitated from a $CH_2Cl_2$—$Et_2O$ solution as an amorphous solid.

FDMS m/e 516.1 (M+)

Analysis for $C_{31}H_{33}NO_4S$-HCl: Calcd: C, 67.44; H, 6.21; N, 2.54; Found: C, 67.70; H, 6.23; N, 2.57.

EXAMPLE 25

Preparation of 3-(4-[2-(2,2-dimethylhydrazino)-2-oxoethoxy]-benzyl]-2-[4-(2-(1-pyrrolidinyl)ethoxy]phenyl]-benzo[b]thiophene.

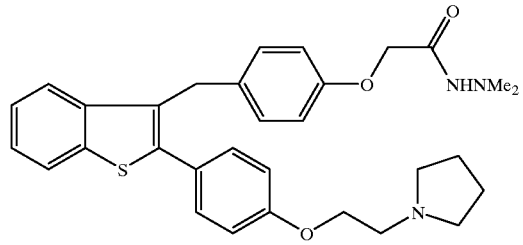

A solution of 1,1-dimethyl hydrazine (0.1 mL, 1.3 mmol) in toluene (5 mL) was added to a solution of trimethyl aluminum (1.3 mL, 1.0M/toluene) in toluene (20 mL) at 0–5° C. The cooling bath was removed and the mixture stirred for 60 minutes. A solution of 3-[4-(2-ethoxy-2-oxoethoxy)benzyl]-2-[4-[2-(1-pyrrolidinyl)ethoxy]phenyl]-benzo[b]thiophene (310 mg, 0.6 mmol) in toluene (5–10 mL) was added and the mixture refluxed for 60 minutes, cooled, decomposed with water, and extracted with $CH_2Cl_2$:i-PrOH (3:1). The organic phase was washed with brine, dried over sodium sulfate, and evaporated in vacuo. The residue was chromatographed on silica gel, eluting with a gradient ($CH_2Cl_2$/5% MeOH/0–1% $Et_3N$) to give the title compound as an amorphous solid (205 mg, 65%).

FDMS 530 (M+)

Analysis for $C_{31}H_{35}N_3O_3S$: Calcd: C, 70.29; H, 6.66; N, 7.93; S, 6.05; Found: C, 70.25; H, 6.60; N, 7.69; S, 6.34.

EXAMPLE 26

Preparation of 3-[4-(2-Dimethylamino-2-oxoethoxy) benzyl]-2-[4-[2-(1-pyrrolidinyl)ethoxy]phenyl]benzo[b]thiophene.

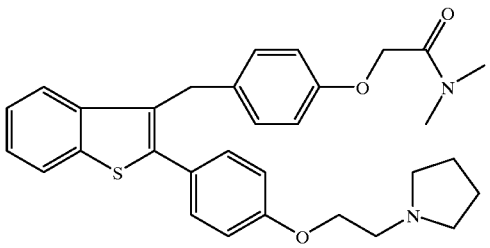

A suspension of dimethylamine hydrochloride (165 mg, 2 mmol) in toluene (20 mL) was cooled to 0–5° C. Trimethyl aluminum (2 mL, 1.0 M in toluene) was added, the cooling bath removed, and the mixture stirred for 60 minutes. A solution of 3-[4-(2-ethoxy-2-oxoethoxy)benzyl]-2-[4-[2-(1-pyrrolidinyl)ethoxy]phenyl]benzo[b]thiophene (310 mg, 0.6 mmol) in toluene (5 mL) was added and the mixture refluxed for 60 minutes, cooled, decomposed with water, and extracted with $CH_2Cl_2$:i-PrOH (3:1). The organic phase was washed with brine, dried over sodium sulfate, and evaporated in vacuo. The residue was chromatographed on silica gel, eluting with a gradient ($CH_2Cl_2$/5% MeOH/0–1% $Et_3N$), to give the title compound as an amorphous solid (200 mg, 64%).

FDMS 515 (M+)

Analyses for $C_{31}H_{34}N_2O_3S$: Calcd: C, 72.34; H, 6.66; N, 5.44; S, 6.23; Found: C, 72.13; H, 6.57; N, 5.24; S, 6.35.

EXAMPLE 27

Preparation of 3-[4-(2-Methylamino-2-oxoethoxy)benzyl]-2-[4-[2-(1-pyrrolidinyl)ethoxy]phenyl]benzo[b]thiophene Hydrochloride.

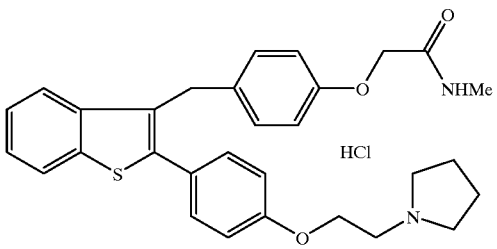

A suspension of methylamine hydrochloride (135 mg, 2 mmol) in toluene (20 mL) was cooled to 0–5° C. Trimethyl aluminum (2 mL, 1.0M in toluene) was added, the cooling bath removed, and the mixture stirred for 60 minutes. A solution of 3-[4-(2-ethoxy-2-oxoethoxy)benzyl]-2-[4-[2-(1-pyrrolidinyl)ethoxy]phenyl]benzo[b]thiophene (310 mg, 0.6 mmol) in toluene (5 mL) was added and the mixture refluxed for 60 minutes, cooled, decomposed with water, and extracted with $CH_2Cl_2$:i-PrOH (3:1). The organic phase was washed with brine, dried over sodium sulfate, and evaporated in vacuo. The residue was chromatographed on silica gel, eluting with a gradient ($CH_2Cl_2$/5% MeOH/0–1% $Et_3N$) to give product as the free base. The title compound was precipitated from a $CH_2Cl_2$—$Et_2O$ solution as an amorphous, hygroscopic solid (95 mg, 30%).

FDMS 501 (M+)

Analysis for $C_{30}H_{32}N_2O_3S \cdot HCl \cdot 0.7H_2O$: Calcd: C, 65.54; H, 6.31; N, 5.10; S, 5.83; Found: C, 65.87; H, 6.58; N, 4.61; S, 5.46.

EXAMPLE 28

Preparation of 3-[4-(2-Amino-2-oxoethoxy)benzyl]-2-[4-[2-(1-pyrrolidinyl)ethoxy]phenyl]benzo[b]thiophene.

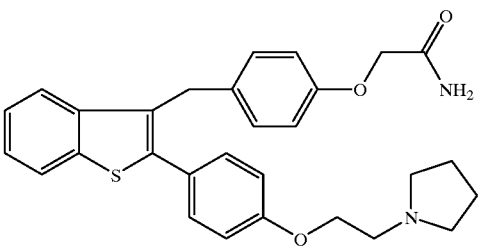

A. 3-[4-(2-Hydroxy-2-oxoethoxy)benzyl]-2-[4-{2-(1-pyrrolidinyl)ethoxy]phenyl]benzo[b]thiophene.

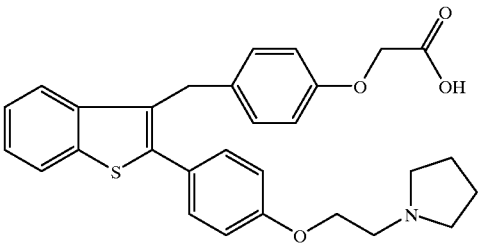

A solution of 3-[4-(2-ethoxy-2-oxoethoxy)benzyl]-2-[4-[2-(1-pyrrolidinyl) ethoxy]phenyl]benzo[b] thiophene (350 mg) and sodium hydroxide (2 mL, 2.0 N) in EtOH (25 mL) was stirred for 18 hours. The pH was adjusted to ca. 7 with 1 N HCl and the suspension concentrated in vacuo to a small volume and filtered. The solid was washed with water and air dried to give the carboxylic acid product (285 mg, 84%).

B. 3-[4-(2-Amino-2-oxoethoxy)benzyl]-2-[4-[2-(1-pyrrolidinyl)ethoxy]phenyl]benzo[b] thiophene.

A mixture of 3-[4-(2-hydroxy-2-oxoethoxy)benzyl]-2-[4-[2-(1-pyrrolidinyl)ethoxy]phenyl]benzo[b]thiophene (250 mg), DMF (1 drop), and oxalyl chloride (0.5 ML) in $CH_2Cl_2$ (50 ML) was stirred for 45 minutes and then evaporated in vacuo.

The residue was dissolved in $CH_2Cl_2$ (70 mL), treated with ammonia gas, and then evaporated in vacuo. The residue was chromatographed on silica gel, eluting with a gradient ($CH_2Cl_2$/8% MeOH/0–2% $Et_3N$), to give title compound as an amorphous solid (130 mg, 52%).

FDMS 486.1 (M+)

Analysis for $C_{29}H_{30}N_2O_3S$: Calcd: C, 71.58; H, 6.21; N, 5.76; Found: C, 66.80; H, 6.10; N. 5.83.

EXAMPLE 29
Preparation of 3-[4-(4-Hydrazino-4-oxobutyloxy)benzyl]-2-[4-[2-(1-pyrrolidinyl)ethoxy]phenyl]benzo[b]thiophene.

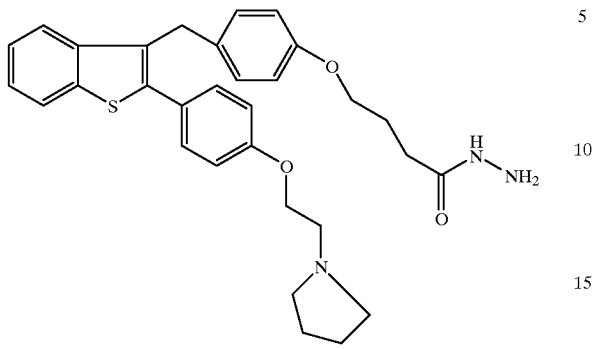

A. 3-[4-(4-Ethoxy-4-oxobutyloxy)benzyl]-2-[4-[2-(1-pyrrolidinyl)ethoxy]phenyl]benzo[b]thiophene Hydrochloride.

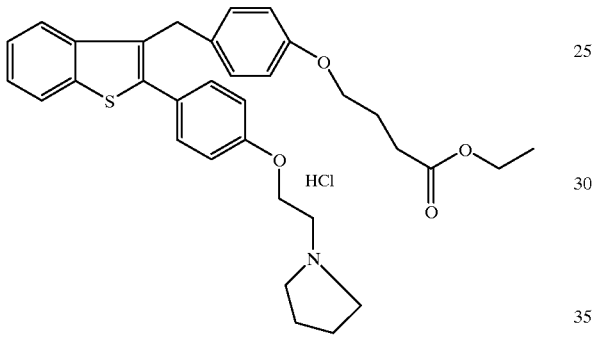

To a stirred solution of 3-(4-hydroxybenzyl)-2-[4-[2-(1-pyrrolidinyl)ethoxy]phenyl]benzo[b]thiophene (1.26 g, 2.93 mmole) and KI (0.97 g, 5.86 mmol) in anhydrous DMF (50 mL) was added NaH (0.24 g, 60% in mineral oil, 5.86 mmole) under nitrogen. The resultant mixture was stirred at room temperature for 10–20 min, followed by the addition of ethyl 4-bromobutyrate and continued stirring at 40° C. until TLC showed completion. The mixture was diluted with EtOAc and ice water. The organic phase was washed with brine, dried with $Na_2SO_4$ and concentrated in vacuum. The resulting crude product was purified on a silica column (gradient 5–20% methanol in $CH_2Cl_2$) to give the title compound as a light yellow oil (1.04 g, 61%). The HCl salt was made by the addition of HCl (1.0 M in $Et_2O$) and concentration in vacuum.

FDMS m/e 543.7 (M+)

Analysis for $C_{33}H_{37}NO_4S \cdot HCl$: Calcd: C, 68.14; H, 6.77; N, 2.39; Found: C, 68.32; H, 6.60; N, 2.41.

B. 3-[4-(4-Hydrazino-4-oxobutyloxy)benzyl]-2-14-[2-(1-pyrrolidinyl)ethoxy]phenyl]benzo[b]thiophene.

To a stirred solution of 3-[4-(4-ethoxy-4-oxobutyloxy)-benzyl]-2-[4-[2-(1-pyrrolidinyl)ethoxy]phenyl]-benzo[b]thiophene (100 mg, 0.18 mmole) in absolute ethanol (25 mL) was added hydrazine (0.06 mL, 1.8 mmole). The resultant mixture was refluxed under nitrogen for a couple hours, then it was concentrated and subjected to a silica column (20% methanol in dichloromethane) to give the title hydrazide derivative as a white foam (49 mg, 51%).

FDMS m/e 529.1 (M+)

Analysis for $C_{31}H_{35}N_3O_3S$: Calcd: C, 70.29; H, 6.66; N, 7.93; Found: C, 67.71; H, 6.49; N, 7.90.

EXAMPLE 30

Preparation of 3-[4-(4-Diethylamino-4-oxobutyloxy)benzyl]-2-[4-[2-(1-pyrrolidinyl)ethoxy]phenyl]benzo[b]thiophene Hydrochloride.

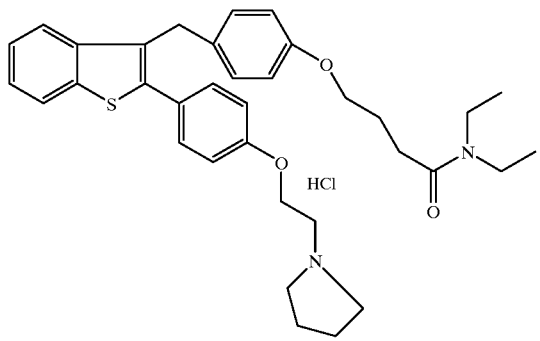

To a stirred solution of 3-[4-(4-ethoxy-4-oxobutyloxy)-benzyl]-2-[4-[2-(1-pyrrolidinyl)ethoxy]phenyl]-benzo[b]thiophene (500 mg, 0.86 mmole) in acetone (25 mL) and $CH_3OH$ (10 mL) was added NaOH (0.5 N, 1.7 mL). The resultant mixture was stirred at ambient temperature overnight. The reaction mixture was neutralized with HCl solution and extracted with $CH_2Cl_2$. The combined organics were dried with $Na_2SO_4$ and concentrated in vacuum to yield the corresponding acid as a white foam (396 mg, 89.3%). The acid was dissolved in dry $CH_2Cl_2$ (30 mL) and oxalyl chloride (0.044 mL, 0.5 mmol) was added at 0–5° C. under nitrogen. The mixture was stirred at room temperature for 4.5 hours and then concentrated to dryness. The crude acyl chloride was dissolved in 30 mL of anhydrous $CH_2Cl_2$. To a portion of the acyl chloride solution (10 mL, ~0.26 mmol) was added diethyl amine (37 mg, 0.51 mmole) at room temperature under nitrogen. The reaction mixture was stirred until TLC showed completion, washed with NaOH solution, and extracted with ethyl acetate. The combined organic layer was dried with $Na_2SO_4$ and concentrated in vacuo. The residue was subjected to a silica column (10% methanol in dichloromethane) to afford the amide product, which was treated with HCl (0.5 mL, 1.0 M in diethyl ether). The title salt was obtained as a yellow foam (125 mg, 79.2%) after concentration.

FDMS m/e 571.1 (M+)

Analysis for $C_{35}H_{42}N_2O_3S \cdot HCl$: Calcd: C, 69.22; H, 7.14; N, 4.61; Found: C, 67.49; H, 7.20; N, 4.49.

EXAMPLE 31
Preparation of 3-[4-(4-Amino-4-oxobutyloxy)benzyl]-2-[4-[2-(1-pyrrolidinyl)ethoxy]phenyl]benzo[b]thiophene Hydrochloride.

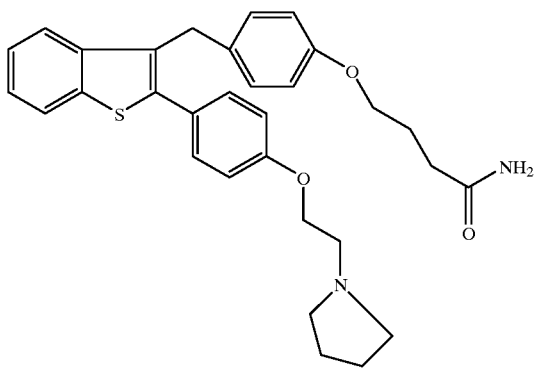

An acyl chloride solution (10 mL, prepared as in Example 30) was treated with ammonia gas for 2–5 min at room temperature. The reaction mixture was washed with NaOH solution and extracted with ethyl acetate. The combined organic layer was dried with $Na_2SO_4$ and concentrated in vacuo. The residue was subjected to a silica column (gradient 5–20% methanol in dichloromethane) to afford the amide product, which was treated with HCl (0.5 mL, 1.0 N in diethyl ether) to provide the salt as a white solid foam (69 mg, 51.6%) after concentration.

FDMS m/e 515.1 (M+)

Analysis for $C_{31}H_{34}N_2O_3S \cdot HCl$: Calcd: C, 67.56; H, 6.40; N, 5.08; Found: C, 61.05; H, 6.16; N, 4.65.

EXAMPLE 32
Preparation of 3-[4-(4-Isopropylamino-4-oxobutyloxy)benzyl]-2-[4-[2-(1-pyrrolidinyl)ethoxy]phenyl]benzo[b]thiophene Hydrochloride.

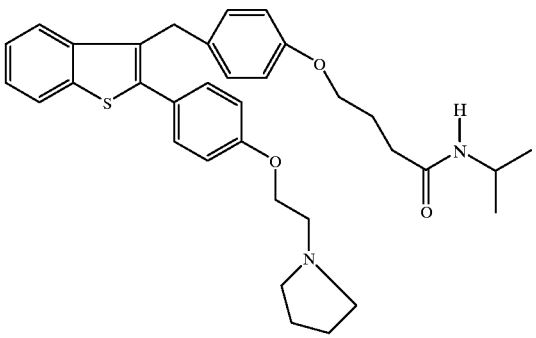

An acyl chloride solution (10 mL, prepared as in Example 30) was treated with isopropyl amine (0.043 mL, 0.5 mmol) and stirred at room temperature until completion of the reaction. The reaction mixture was washed with NaOH solution and extracted with ethyl acetate. The combined organic layer was dried with $Na_2SO_4$ and concentrated in vacuo. The residue was subjected to a silica column (gradient 5–20% methanol in dichloromethane) to afford the amide product, which was treated with HCl (0.5 mL, 1.0 M in diethyl ether)to afford the title salt as a white solid foam (62 mg, 44.5%) after concentration.

FDMS m/e 557.1 (M+)

Analysis for $C_{34}H_{40}N_2O_3S \cdot HCl$: Calcd: C, 68.84; H, 6.97; N, 4.72; Found: C, 66.07; H, 6.88; N, 4.64.

EXAMPLE 33
Preparation of 3-[4-(5-Amino-5-oxopentyloxy)benzyl]-2-[4-[2-(1-pyrrolidinyl)ethoxy]phenyl]benzo[b]thiophene Hydrochloride.

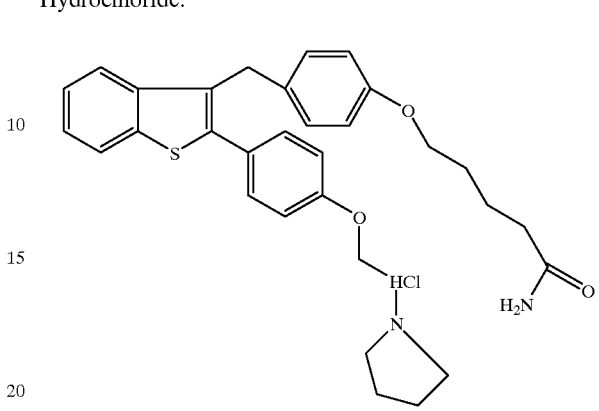

A. 3-[4-(S-Methoxy-5-oxopentyloxy)benzyl]-2-[4-[2-(1-pyrrolidinyl)ethoxy]phenyl]benzo[b]thiophene.

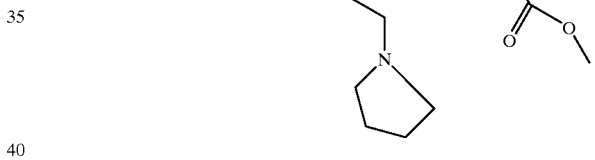

To a stirred solution of 3-(4-hydroxybenzyl)-2-[4-[2-(1-pyrrolidinyl)ethoxy]phenyl]benzo[b]thiophene (1.5 g, 3.5 mmole) and KI (0.87 g, 5.2 mmol) in anhydrous DMF (50 mL) was added NaH (0.28 g, 7.0 mmol) under nitrogen at room temperature. The reaction mixture was stirred for 10–15 min before methyl 5-bromovalerate (0.75 mL, 5.25 mmol)was added, and it was stirred for an additional 2 hours and then diluted with ethyl acetate and $NH_4Cl$ solution. The organic layer was washed with brine, dried with $Na_2SO_4$ and concentrated in vacuo. The residue was subjected to a $SiO_2$ column, eluted with 5% methanol in $CH_2Cl_2$, to give the ester product as a yellow oil (1.42 g, 75%).

FDMS m/e 543.19 (M+)

B. 3-[4-(5-Amino-5-oxopentyloxy)benzyl]-2-[4-[2-(1-pyrrolidinyl)ethoxy]phenyl]benzo[b]thiophene Hydrochloride.

The title compound was prepared from the product of Part A following the procedures of Example 31.

FDMS m/e 529 (M+)

Analysis for $C_{32}H_{36}N_2O_3S \cdot HCl$: Calcd: $C_{68.00}$, H 6.60, H 4.96; Found: $C_{64.23}$, H 6.34, N 4.37.

EXAMPLE 34

Preparation of 3-[4-(6-Amino-6-oxopentyloxy)benzyl-2-[4-[2-(1-pyrrolidinyl)ethoxy]phenyl]benzo[b]thiophene Hydrochloride.

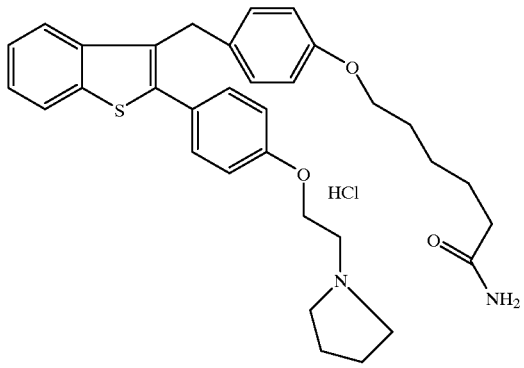

A. 3-[4-(6-Ethoxy-6-oxohexyloxy)benzyl]-2-[4-[2-(1-pyrrolidinyl)ethoxy]phenyl]benzo[b]thiophene hydrochloride.

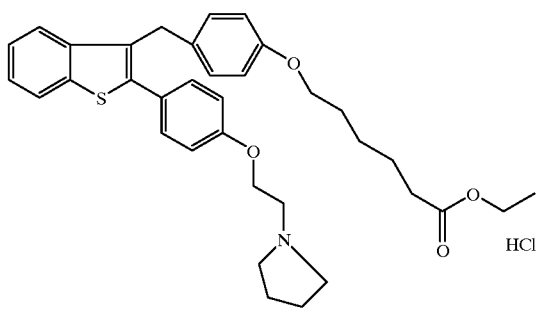

To a stirred solution of 3-(4-hydroxybenzyl)-2-[4-[2-(1-pyrrolidinyl)ethoxy]phenyl]benzo[b]thiophene (2.0 g, 4.7 mmole) and KI (1.2 g, 7.1 mmol) in anhydrous DMF (50 mL) was added NaH (60% in mineral oil, 0.37 g, 9.4 mmol) under nitrogen at room temperature. The reaction mixture was stirred for 10–15 min and then ethyl 6-bromohexanoate (1.25 mL, 7.1 mmol) was added. The reaction mixture was stirred for an additional 2 hours and then diluted with ethyl acetate and NH$_4$Cl solution. The organic layer was washed with brine, dried with Na$_2$SO$_4$ and concentrated in vacuo. The residue was subjected to SiO$_2$ column, eluted with 5% methanol in CH$_2$Cl$_2$, to give the ester product as a yellow oil (2.1 g, 79.5%). The title HCl salt was made by treatment with HCl solution (1 M in diethyl ether).

FDMS m/e 572 (M+)

Analysis for C$_{35}$H$_{41}$NO$_4$S.HCl: Calcd: C, 69.11; H, 6.96; N, 2.30; Found: C, 66.91; H, 6.11; N, 1.98.

B. 3-[4-(6-Amino-6-oxopentyloxy)benzyl]-2-[4-[2-(1-pyrrolidinyl)ethoxy]phenyl]benzo[b]thiophene Hydrochloride.

The title compound was prepared following the procedures of Example 31.

FDMS m/e 543 (M+)

Analysis for C$_{33}$H$_{38}$N$_2$O$_3$S.HCl: Calcd: C, 68.43; H, 6.79; H, 4.84; Found: C, 62.82; H, 6.45; N, 4.45.

EXAMPLE 35

Preparation of 3-[4-(4-Amino-3-methyl-4-oxobutyloxy)benzyl]-2-[4-[2-(1-pyrrolidinyl)ethoxy]phenyl]benzo[b]thiophene Hydrochloride.

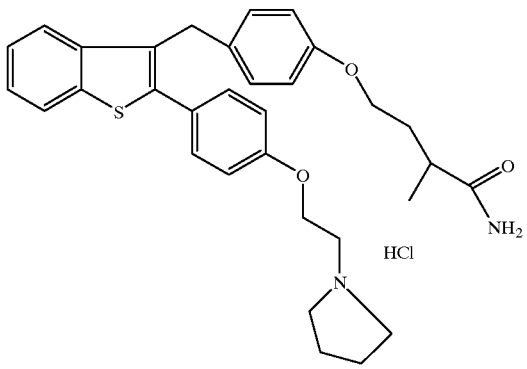

A. 3-[4-(4-Methoxy-3-methyl-4-oxobutyloxy)benzyl]-2-[4-[2-(1-pyrrolidinyl)ethoxy]phenyl]benzo[b]thiophene Hydrochloride.

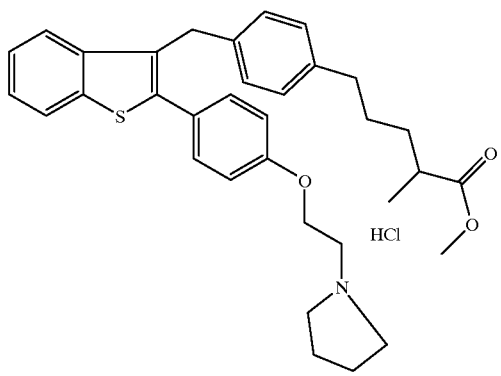

The title ester was prepared following the procedure of Example 29, Part A, utilizing methyl 2-methyl-4-bromobutyrate.

FDMS m/e 544 (M+)

Analysis for C$_{31}$H$_{37}$NO$_4$S.HCl: Calcd: C, 68.32; H, 6.60; N, 2.41; Found: C, 65.47; H, 6.57; N, 2.43.

B. 3-[4-(4-Hydroxy-3-methyl-4-oxobutyloxy)benzyl]-2-[4-[2-(1-pyrrolidinyl)ethoxy]phenyl]benzo[b]thiophene.

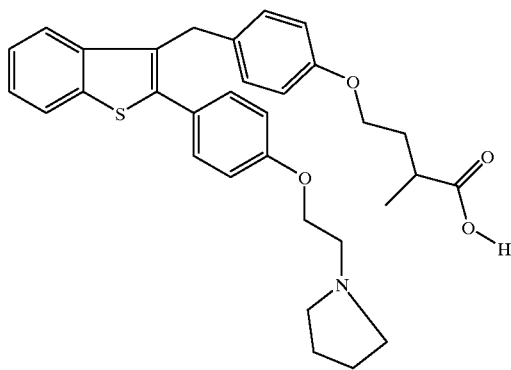

Hydrolysis of the product from Part A was carried out at room temperature with NaOH solution using acetone and methanol as the solvent to afford the title acid.

FDMS m/e 530 (M+)

Analysis for C$_{30}$H$_{35}$NO$_4$S: Calcd: C, 72.56; H, 6.66; N, 2.64; Found: C, 65.00; H, 6.42; N, 2.31.

C. 3-[4-(4-Amino-3-methyl-4-oxobutyloxy)benzyl]-2-[4-[2-(1-pyrrolidinyl)ethoxy]phenyl]benzo[b]thiophene Hydrochloride.

The title compound was prepared from the product of Part B following the procedure of Example 31.

FDMS m/e 529 (M+)

Analysis for C$_{30}$H$_{36}$N$_2$O$_3$S.HCl: Calcd: C, 72.70; H, 6.86; N, 2.20; Found: C, 58.73; H, 6.11; N, 4.28.

EXAMPLE 36

Preparation of 3-[4-(2-Methylthiazol-4-ylmethoxy)benzyl]-2-[4-[2-(1-pyrrolidinyl)ethoxy]phenyl]benzo[b]thiophene Dihydrochloride.

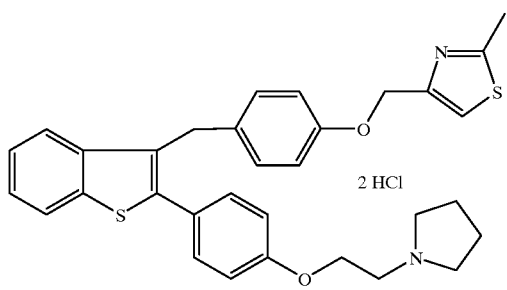

A. 3-[4-(2-Methylthiazol-4-ylmethoxy)benzoyl]-2-[4-[2-(1-pyrrolidinyl)ethoxy]phenyl]benzo[b]thiophene.

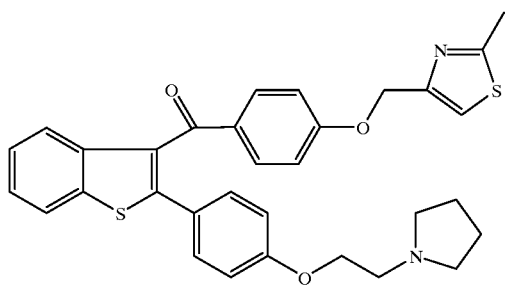

A suspension of 3-(4-hydroxybenzoyl)-2-[4-[2-(1-pyrrolidinyl)ethoxy]phenyl]benzo[b]thiophene (450 mg, 1.0 mmol) in DMF (40 mL) was treated with sodium hydride (60% in mineral oil, 100 mg, 2.5 mmol) for 10 minutes and then with 4-chloromethyl-2-methylthiazole hydrochloride (220 mg, 1.2 mmol) for 23.5 hours in an oil bath at 55° C. The solution was cooled, diluted with water, and extracted with ethyl acetate. The organic phase was washed with water, brine, dried over sodium sulfate, and evaporated in vacuo. The residue was chromatographed on silica gel, eluting with a gradient (CH$_2$Cl$_2$/2–8% MeOH), to give the O-alkylated product (405 mg, 73%).

B. 3-[4-(2-Methylthiazol-4-ylmethoxy)benzyl]-2-[4-[2-(1-pyrrolidinyl)ethoxy]phenyl]benzo[b]thiophene Dihydrochloride.

The product from Part A was dissolved in THF (50 mL) and treated with LAH (1 g). The cooling bath was removed and the mixture stirred 1 hour, cooled in ice-water and decomposed by the sequential addition of ethyl acetate and 5N sodium hydroxide. The solution was decanted from the insolubles which were washed well with CH$_2$Cl$_2$. The aqueous THF solution was extracted with CH$_2$Cl$_2$ and the combined organics washed with brine, dried over sodium sulfate, and evaporated in vacuo to give 3-[4-(2-methylthiazol-4-yl-methoxy)-α-hydroxybenzyl]-2-[4-[2-(1-pyrrolidinyl)ethoxy]-phenyl]benzo[b]thiophene, which was dissolved in CH$_2$Cl$_2$ (25 mL) and treated with triethylsilane (1 mL) and TFA (1 mL) for 1.5 hours, washed with aqueous sodium bicarbonate, dried over sodium sulfate, and evaporated in vacuo. The residue was chromatographed on silica gel, eluting with a gradient (CH$_2$Cl$_2$/2–5% MeOH), to give the product as the free base which was converted to the dihydrochloride by treatment with HCl in an Et$_2$O/CH$_2$Cl$_2$ solution (amorphous solid, 330 mg, 50%).

FDMS 540.9 (M+)

Analysis for C$_{32}$H$_{32}$N$_2$O$_2$S$_2$.2HCl: Calcd: C, 62.68; H, 5.67; N, 4.13; Found: C, 62.63; H, 5.58; N, 4.57.

EXAMPLE 37

Preparation of (S)-3-[4-[2-(2-Oxopyrrolidin-1-yl)propyloxy]-benzyl]-2-[4-[2-(1-pyrrolidinyl)ethoxy]phenyl]-benzo[b]thiophene Oxalate.

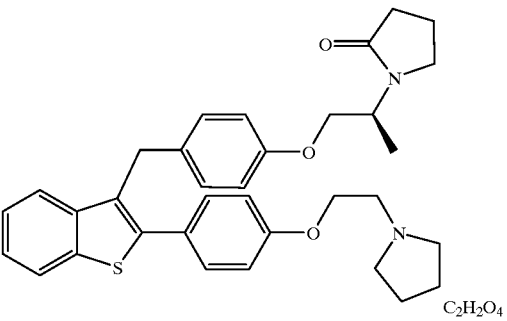

A. (S)-2-(tert-Butyldiphenylsilyloxy)-1-(methyl)-ethylamine.

A solution of 10.0 g (133 mmol) of S-(+)-2-amino-1-propanol and 13.6 g (200 mmol) of imidazole in 100 mL of DMF was treated with 38.1 mL (146 mmol) of t-butyldiphenylsilyl chloride. The reaction mixture was stirred at room temperature until tlc analysis indicated complete consumption of starting material (2 h), diluted with 250 mL of H$_2$O, and extracted with EtOAc (3×200 mL). The combined organic layers were washed with H$_2$O (3×300 mL), dried over Na$_2$SO$_4$, filtered and concentrated in vacuo to give an oil. Purification by flash chromatography (2% then 5% MeOH in CH$_2$Cl$_2$) afforded 16.4 g (52.4 mmol; 39%) of the title ether as an oil.

FDMS 314 (M+1); Anal. calcd for C$_{19}$H$_{27}$NOSi: C, 72.79; H, 8.68; N, 4.47. Found: C, 73.04; H, 8.78; N, 4.45.

B. (S)-2-(2-Oxopyrrolidin-1-yl)propyl tert-Butyldiphenyl-silyl Ether.

A solution of 16.32 g (52.5 mmol) of (S)-2-(tert-butyldiphenylsilyloxy)-1-(methyl)ethylamine (part A), 6.70 g (57.8 mmol) of methyl 3-formylpropionate and 11.0 mL of TEA in 100 mL of MeOH was stirred at ambient temperature for 2 h, concentrated in vacuo, reconstituted in 100 mL of MeOH, and treated with 3.05 g (78.8 mmol) of NaBH$_4$ in portions. The reaction mixture was heated to 50° C. overnight, diluted with 300 mL of H$_2$O, and extracted with EtOAc (3×300 mL). The combined organic layers were dried over Na$_2$SO$_4$, filtered and concentrated in vacuo to give 21.6 g of an oil. Purification by flash chromatography (SiO$_2$; 5% MeOH in CH$_2$Cl$_2$) afforded 11.6 g (30.2 mmol; 57%) of the title ether as an oil.

FDMS 382 (M+1); Anal. calcd for C$_{23}$H$_{31}$NO$_2$Si: C, 72.40; H, 8.19; N, 3.67. Found: C, 72.28; H, 8.12; N, 3.78.

C. (S)-4-[2-(2-Oxopyrrolidin-1-yl)propyloxy]phenyl 2-[4-[2-(1-Pyrrolidinyl)ethoxy]phenyl]benzo[b]thiophen-3-yl Ketone.

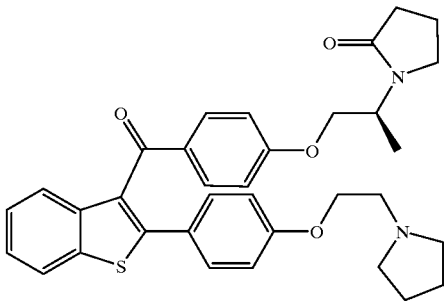

A 0° C. solution of 11.20 g (29.4 mmol) of (S)-2-(2-oxopyrrolidin-1-yl)propyl tert-butyldiphenylsilyl ether (Part B) in 100 mL of THF was treated with 36.0 mL (36 mmol) of tetrabutylammonium fluoride (1 M in THF). The reaction was stirred at ambient temperature until tlc analysis indicated the complete disappearance of starting material (30 min). The reaction was poured into 300 mL of H$_2$O and the mixture extracted with CH$_2$Cl$_2$ (3×300 mL). The combined organic layers were dried over Na$_2$SO$_4$, filtered and concentrated in vacuo to give 8.40 g of the corresponding (S)-2-(2-oxopyrrolidin-1-yl)propyl alcohol which was used without purification.

A 0° C. mixture of 1.25 g (2.80 mmol) of 4-fluorophenyl 2-[4-[2-(1-pyrrolidinyl)ethoxy]phenyl]benzo[b]thiophen-3-yl ketone and 0.18 g of NaH in 25 mL of THF was treated with a solution of 0.52 g (3.6 mmol) of the above crude (S)-2-(2-oxopyrrolidin-1-yl)propyl alcohol in 5 mL of DMF in a dropwise manner. The reaction mixture was stirred at ambient temperature, reaching room temperature overnight. The reaction mixture was poured into 50 mL of H$_2$O and the mixture extracted with EtOAc (3×100 mL). The combined organic layers were washed with H$_2$O (2×250 mL), dried over Na$_2$SO$_4$, filtered and concentrated in vacuo to give 1.50 g of an oil. Purification by flash chromatography (SiO$_2$; 3% MeOH in CH$_2$Cl$_2$) afforded 1.06 g (1.86 mmol; 67%) of the title ketone as an oil.

FDMS 569 (M+); Anal. calcd for C$_{34}$H$_{36}$N$_2$O$_4$S.C$_2$H$_2$O$_4$.2H$_2$O: C, 63.20; H, 6.10; N, 4.12. Found: C, 62.90; H, 5.74; N, 4.03.

D. (S)-3-[4-[2-(2-oxopyrrolidin-1-yl)propyloxy]benzyl]-2-[4-[2-(1-pyrrolidinyl)ethoxy]phenyl]benzo[b]thiophene Oxalate.

By essentially following the conditions described in Example 1, Part D, the title compound was prepared from (S)-4-[2-(2-oxopyrrolidin-1-yl)propyloxyphenyl 2-(4-[2-(1-pyrrolidinyl)ethoxy]phenyl]benzo[b]thiophen-3-yl ketone (Part C). The free base was converted to the oxalate salt by following the conditions described in Example 1, Part F.

FDMS 555 (M+1); Anal. calcd for C$_{34}$H$_{38}$N$_2$O$_3$S.C$_2$H$_2$O$_4$.H$_2$O: C, 66.50; H, 6.49; N, 4.36. Found: C, 66.68; H, 6.16; N, 4.23.

EXAMPLE 38
Preparation of (R)-3-[4-[2-(2-Oxopyrrolidin-1-yl)propyloxy]-benzyl]-2-[4-[2-(1-pyrrolidinyl)ethoxy]phenyl]-benzo[b]thiophene Oxalate.

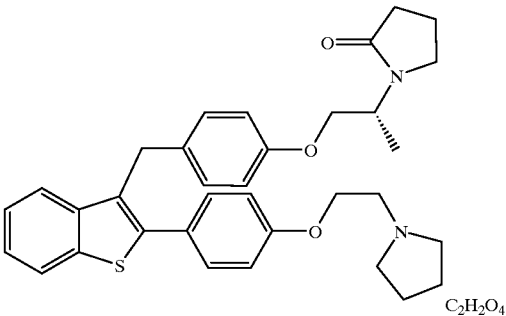

A. (R)-2-(tert-Butyldiphenylsilyloxy)-1-(methyl)-ethylamine.

By essentially following the conditions described in Example 37, Part A, the title compound was prepared from (R)-(−)-2-amino-1-propanol in 65% yield.

FDMS 314 (M+1); Anal. calcd for C$_{19}$H$_{27}$NOSi: C, 72.79; H, 8.68; N, 4.47. Found: C, 71.59; H, 8.44; N, 4.38.

B. (R)-2-(2-Oxopyrrolidin-1-yl)propyl tert-Butyldiphenylsilyl Ether.

By essentially following the conditions described in Example 37, Part B, the title compound was prepared from (R)-2-(tert-butyldiphenylsilyloxy)-1-(methyl)ethylamine (Part A).

FDMS 382 (M+1); Anal. calcd for C$_{23}$H$_{31}$NO$_2$Si: C, 72.40; H, 8.19; N, 3.67. Found: C, 72.59; H, 8.30; N, 3.77.

C. (R)-4-[2-(2-Oxopyrrolidin-1-yl)propyloxy]phenyl 2-[4-[2-(1-Pyrrolidinyl)ethoxy]phenyl]benzo[b]thiophen-3-yl Ketone Oxalate.

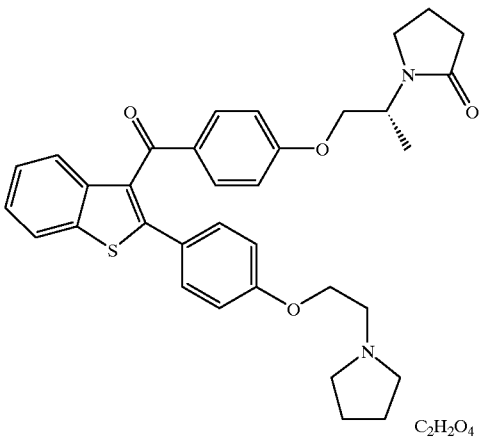

By essentially following the conditions described in Example 37, Part C, the title compound was prepared from (R)-2-(2-oxopyrrolidin-1-yl)propyl tert-butyldiphenylsilyl ether (Part B). FDMS 570 (M+1); Anal. calcd for C$_{34}$H$_{36}$N$_2$O$_4$S.C$_2$H$_2$O$_4$.H$_2$O: C, 64.39; H, 6.01; N, 4.20. Found: C, 64.14; H, 5.62; N, 4.11.

D. (R)-3-[4-[2-(2-oxopyrrolidin-1-yl)propyloxy]benzyl]-2-[4-[2-(1-pyrrolidinyl)ethoxy]phenyl]benzo[b]thiophene Oxalate.

By essentially following the conditions described in Example 37, Part D, the title compound was prepared from (R)-4-[2-(2-oxopyrrolidin-1-yl)propyloxy]phenyl 2-[4-[2(1-pyrrolidinyl)ethoxy]phenyl]benzo[b]thiophen-3-yl ketone (Part C). The free base was converted into the oxalate salt by following the conditions described in Example 1, Part F.

FDMS 555 (M+1); Anal. calcd for $C_{34}H_{38}N_2O_3S \cdot C_2H_2O_4$: C, 66.50; H, 6.49; N, 4.36. Found: C, 66.38; H, 6.12; N, 4.19.

EXAMPLE 39

Preparation 4-[2-(2-Oxopyrrolidin-1-yl)ethoxy]phenyl 2-[3-Hydroxy-4-[2-(1-pyrrolidinyl)ethoxy]phenyl]-benzo[b]thiophen-3-yl Ketone Oxalate.

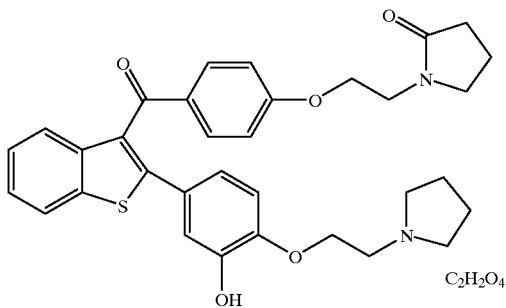

A. 4-Bromo-2-Methoxyphenyl 2-(1-Pyrrolidinyl)ethyl Ether.

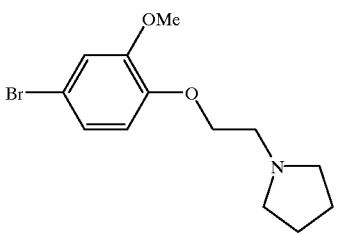

4-Bromoguaiacol (4-bromo-2-methoxyphenol, 30 g, 147.8 mmol) and 1-(2-chloroethyl)pyrrolidine HCl (37.7 g, 221.6 mmol) were heated at 80° C. in 500 mL of DMF in the presence of $K_2CO_3$ (61.3 g, 443.3 mmol) for 20 h. After cooling, the crude product was filtered and concentrated in vacuo. The crude residue was purified by flash chromatography ($SiO_2$; gradient of 0–2% TEA in EtOAc) to afford 27.7 g (92.3 mmol; 62%) of the title compound as a clear, colorless oil.

FDMS 299 (M−1), 301 (M+1); Anal. calcd for $C_{13}H_{18}BrNO_2$: C, 52.01; H, 6.04; N, 4.67. Found: C, 52.24; H, 5.97; N, 4.62.

B. 2-[3-Methoxy-4-[2-(1-pyrrolidinyl)ethoxy]phenyl]-benzo[b]thiophene.

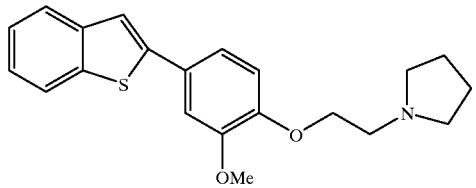

A solution of benzo[b]thiophene-2-boronic acid (18 g, 101.1 mmol) and 4-bromo-2-methoxyphenyl 2-(1-pyrrolidinyl)-ethyl ether (27.6 g, 91.9 mmol) in 500 mL of THF was treated with Pd (PPh₃)₄ (5 g, 4.3 mmol) and 96 mL of 2N aqueous $Na_2CO_3$. The resulting mixture was heated overnight at 60° C. in the dark. Upon cooling to room temperature, the organic layer was decanted away from the solids, which were rinsed with THF (3×100 mL). The combined organic layers were concentrated in vacuo. Purification of the crude residue by flash chromatography ($SiO_2$; gradient of 0–2% TEA in EtOAc) gave a quantitative yield of the title compound as a light tan solid. FDMS 353 (M+); Anal. calcd for $C_{21}H_{23}NO_2S \cdot 0.2H_2O$: C, 70.63; H, 6.61; N, 3.92. Found: C, 70.69; H. 6.52; N, 4.12.

C. 2-[3-Hydroxy-4-[2-(1-pyrrolidinyl)ethoxy]phenyl]-benzo[b]thiophene.

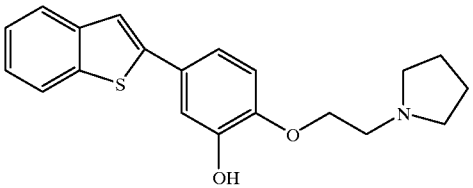

A 0° C. solution of 2-[3-methoxy-4-[2-(1-pyrrolidinyl)-ethoxy]phenyl]benzo[b]thiophene (32 g, 91.9 mmol) in 500 mL of dichloroethane was treated with $BBr_3$ (92 g, 369.6 mmol) dropwise via a dropping funnel. After 1.5 h, the reaction mixture was slowly poured into 1 L saturated aqueous $NaHCO_3$/ice. The layers were separated, and the aqueous layer was extracted with 5% MeOH/CHCl₃ (5×200 mL). The brown solid boron complex was stirred in 200 mL of 1N HCl. The acidic solution was neutralized with NaOH and extracted with EtOAc (4×150 mL). The combined organic layers were dried over $K_2CO_3$, filtered and concentrated in vacuo. The crude residue was purified by flash chromatography ($SiO_2$; 1% MeOH in CHCl₃, saturated with $NH_4OH$) to give 8.01 g (23.7 mmol, 26%) of the title phenol as an off-white solid.

ISMS 338 (M−1), 340 (M+1); Anal. calcd for $C_{20}H_{21}NO_2S \cdot 0.5H_2O$: C, 68.94; H, 6.36; N, 4.02. Found: C, 68.88; H, 6.23; N, 4.20.

D. 4-Fluorophenyl 2-[3-(4-Fluorobenzoyloxy)-4-[2-(1-pyrrolidinyl)ethoxy]phenyl]benzo[b]thiophen-3-yl Ketone.

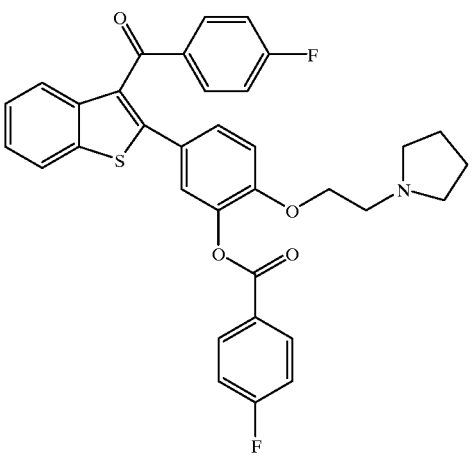

A 0° C. solution of 2-[3-hydroxy-4-[2-(1-pyrrolidinyl)-ethoxy]phenyl]benzo[b]thiophene (6.7 g, 19.8 mmol) in 200 mL of dichloroethane was treated with 4-fluorobenzoyl chloride (2.6 mL, 21.8 mmol) dropwise. A white precipitate formed. The reaction mixture was warmed to ambient temperature and stirred for 6.5 h. The intermediate ester was cooled to 0° C. and treated with 4-fluorobenzoyl chloride (2.6 mL, 21.8 mmol) and $TiCl_4$ (8.7 mL, 79.2 mmol). The reaction mixture was allowed to warm to ambient temperature. After 5 h, the reaction mixture was slowly poured into 200 mL saturated aqueous NaHCO$_3$. The layers were separated, and the aqueous layer was extracted with CHCl$_3$ (4×100 mL). The combined organic layers were dried over K$_2$CO$_3$, filtered and concentrated in vacuo. Purification of the crude residue by PrepLC (SiO$_2$; gradient of 100% CHCl$_3$ to 0.5% MeOH in CHCl$_3$, saturated with NH$_4$OH) afforded 7.5 g (12.9 mmol, 65%) of the title compound as a yellow foam.

ISMS 584 (M+l); Anal. calcd for C$_{34}$H$_{27}$F$_2$NO$_4$S.H$_2$O: C, 67.87; H, 4.86; N, 2.33. Found: C, 67.87; H, 4.82; N, 2.41.

E. 2-[3-Hydroxy-4-[2-(1-pyrrolidinyl)ethoxy]phenyl]-benzo[b]thiophen-3-yl 4-[2-(2-Oxopyrrolidin-1-yl)ethoxy]-phenyl Ketone Oxalate.

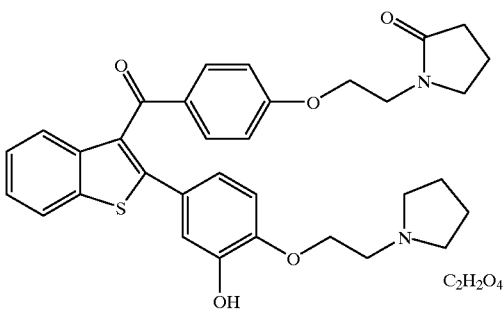

A 0° C. mixture of 4-fluorophenyl 2-[3-(4-fluoro-benzoyloxy)-4-[2-(1-pyrrolidinyl)ethoxy]phenyl]-benzo[b]thiophen-3-yl ketone (7.0 g, 12.0 mmol) and NaH (1.1 g, 26.4 mmol) in 60 mL of DMF was treated with 1-(2-hydroxyethyl)pyrrolidin-2-one (2.85 mL, 25.2 mmol) dropwise. After 30 min the reaction mixture was warmed to ambient temperature and allowed to stir overnight. The reaction mixture was poured into 150 mL of brine, and the aqueous layer was extracted with EtOAc (4×100 mL). The combined organic layers were washed with H$_2$O (2×300 mL) dried over K$_2$CO$_3$, filtered and concentrated in vacuo. Purification of the crude residue by PrepLC (SiO$_2$; gradient of 0–2% MeOH/CHCl$_3$, saturated with NH$_4$OH) afforded 5.35 g (9.37 mmol, 78%) of the title compound. A small sample of the title ketone was converted into its oxalate salt.

FDMS 571 (M+1); Anal. calcd for C$_{33}$H$_{34}$N$_2$O$_5$S.1C$_2$H$_2$O$_4$0.1H$_2$O: C, 63.45; H. 5.51; N, 4.23. Found: C, 63.18; H. 5.87; N, 4.62.

EXAMPLE 40

Preparation of 2-[3-Hydroxy-4-[2-(1-pyrrolidinyl)ethoxy]phenyl]-3-[4-[2-(2-oxopyrrolidin-1-yl)ethoxy]benzyl]-benzo[b]thiophene Oxalate.

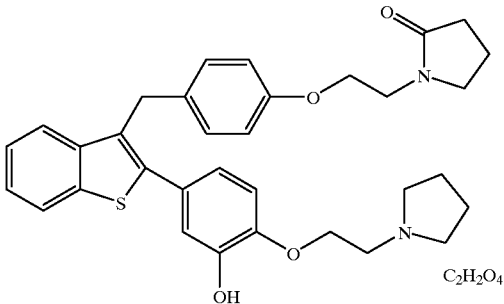

A −35° C. solution of 2-[3-hydroxy-4-[2-(1-pyrrolidinyl)ethoxy]phenyl]benzo[b]thiophen-3-yl 4-[2-(2-oxo-pyrrolidin-1-yl)ethoxy]phenyl ketone (5.0 g, 8.76 mmol) in 50 mL of THF was treated with LAH (8.8 mL, 8.76 mmol; 1 M in THF) dropwise. After 3 h the reaction mixture was quenched cold with 10 mL of H$_2$O. EtOAc and saturated aqueous Rochelle's salt (50 mL each) were added. The layers were separated, and the aqueous layer was extracted with EtOAc (4×50 mL). The combined organic layers were dried over K$_2$CO$_3$, filtered and concentrated in vacuo. Purification of the crude residue by PrepLC (SiO$_2$; gradient of 0.5–1% MeOH/CHCl$_3$, saturated with NH$_4$OH) afforded 4.0 g of the intermediate alcohol which was immediately dissolved in 50 mL of dichloroethane. The resulting solution was treated with Et$_3$SiH (9.8 mL, 61.3 mmol). Upon cooling to 0° C., TFA (6.7 mL, 87.6 mmol) was added dropwise. After 1 h, the reaction mixture was poured into 150 mL of saturated aqueous NaHCO$_3$. The layers were separated, and the aqueous layer was extracted with CHCl$_3$ (3×50 mL). The combined organic layers were dried over K$_2$CO$_3$, filtered and concentrated in vacuo. Purification of the crude residue by flash chromatograhy (SiO$_2$; gradient of 1–2% MeOH/CHCl$_3$, saturated with NH$_4$OH) afforded 3.3 g (5.93 mmol, 68%) of the title compound, of which a small sample was converted to its oxalate salt.

FDMS 557 (M+1); Anal. calcd for C$_{33}$H$_{36}$N$_2$O$_4$S.C$_2$H$_2$O$_4$: C, 65.00; H, 5.92; N, 4.33. Found: C, 64.73; H, 6.13; N, 4.54.

What is claimed is:

1. A compound of formula I (or a pharmaceutically acceptable salt thereof)

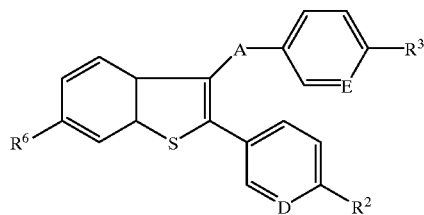

wherein

A is carbonyl or methylene;

D is CH, CR$^d$ or N in which R$^d$ is hydroxy, methyl or methoxy;

E is CH, CR$^e$ or N in which R$^e$ is methyl, methoxy or halo;

R$^2$ is —X$^2$—(CH$_2$)$_m$—NR$^a$R$^b$ in which X$^2$ is a direct bond, methylene, O or S; m is 1, 2, 3, 4 or 5; provided that when m is 1, then X$^2$ is a direct bond; and R$^a$ and R$^b$ are independently hydrogen or (1–3C)alkyl or the group NR$^a$R$^b$ is pyrrolidino, piperidino, or morpholino;

R$^3$ is —X$^3$—(CH$_2$)$_n$—L—R$^c$, —O—CHR$^f$—CHR$^f$—R$^c$, —O—N(R$^g$)$_2$, —S—R$^h$ or —CO—R$^i$ in which X$^3$ is a direct bond, methylene or O; n is 1 or 2, provided that when n is 1, then X$^2$ is a direct bond; L is —(CH$_2$)$_k$— in which k is 0, 1, 2 or 3, or L is —(CHCH$_3$)—; R$^c$ is cyano, cyclopentyl, 2-oxopyrrolidin-1-yl, 2,5-dioxopyrrolidin-1-yl, 2-oxooxazolidin-3-yl, 2-oxoimidazolidin-1-yl, 3-methyl-2-oxoimidazolidin-1-yl, 2-oxopyrrolidin-3-yl, 1-methyl-2-oxopyrrolidin-3-yl, 1-tetrazolyl, methoxy, methylsulfonylamino or phenylsulfonylamino; or R$^c$ is 2-methylthiazol-4-yl, CONR$^j$R$^k$ or CONHNR$^j$R$^k$ in which R$^j$ is hydrogen, methyl or ethyl and R$^k$ is hydrogen, methyl, ethyl or isopropyl; the two R$^f$ groups together form a tetramethylene diradical so that the resulting 1,2-cyclohexanediyl group is trans; R$^g$ is methyl or ethyl; R$^h$ is 2-thiazolyl; and R$^i$ is methoxy, dimethylamino or pyrrolidino; and $R^6$ is hydrogen, hydroxy or methoxy.

2. The compound of formula I (or a pharmaceutically acceptable salt thereof) as claimed in claim 1 wherein
A is carbonyl or methylene;
D is CH, $CR^d$ or N in which $R^d$ is methyl or methoxy;
E is CH, $CR^e$ or N in which $R^e$ is methyl, methoxy or halo;
$R^2$ is $-X^2-(CH_2)_m-NR^aR^b$ in which $X^2$ is a direct bond, methylene, O or S; m is 1, 2, 3, 4 or 5; provided that when m is 1, then $X^2$ is a direct bond; and $R^a$ and $R^b$ are independently hydrogen or (1-3C)alkyl or the group $NR^aR^b$ is pyrrolidino, piperidino, or morpholino;
$R^3$ is $-X^3-(CH_2)_n-R^c$, $-O-CHR^f-CHR^f-R^c$, $-O-N(R^g)_2$, $-S-R^h$ or $-CO\ R^i$ in which $X^3$ is a direct bond, methylene or O; n is 1 or 2, provided that when n is 1, then $X^2$ is a direct bond; $R^c$ is cyano, cyclopentyl, 2-oxopyrrolidin-1-yl, 2,5-dioxopyrrolidin-1-yl, 2-oxooxazolidin-3-yl, 2-oxoimidazolidin-1-yl, 3-methyl-2-oxoimidazolidin-1-yl, 2-oxopyrrolidin-3-yl, 1-methyl-2-oxopyrrolidin-3-yl, 1-tetrazolyl, methoxy, methylsulfonylamino or phenylsulfonylamino; the two $R^f$ groups together form a tetramethylene diradical so that the resulting 1,2-cyclohexanediyl group is trans; $R^g$ is methyl or ethyl, $R^h$ is 2-thiazolyl; and $R^i$ is methoxy, dimethylamino or pyrrolidino; and
$R^6$ is hydrogen, hydroxy or methoxy.

3. The compound (or salt thereof) of claim 1 or 2 wherein halo is fluoro, chloro, bromo or iodo; and a (1-3C)alkyl group is methyl, ethyl, propyl or isopropyl.

4. The compound (or salt thereof) of claim 1 wherein
D is CH;
E is $CR^e$ in which $R^e$ is methyl or methoxy; and
$R^2$ is 2-(1-pyrrolidinyl)-ethoxy.

5. The compound (or salt thereof) of claim 1 wherein $R^3$ is (2-oxopyrrolidin-1-yl)methyl or 2-(2-oxopyrrolidin-1-yl) ethoxy.

6. The compound (or salt thereof) of claim 1 wherein $R^6$ is hydroxy.

7. The compound (or salt thereof) of claim 1 wherein A is methylene.

8. The compound as claimed in claim 1 selected from
(a) 6-hydroxy-3-[3-methyl-4-[(2-oxopyrrolidin-1-yl) methyl]benzyl]-2-[4-[2-(1-pyrrolidinyl)ethoxy] phenyl]-benzo[b]thiophene,
(b) 1-[2-[2-methoxy-4-[[6-hydroxy-2-[4-[2-(1-pyrrolidinyl)ethoxy]phenyl]benzo[b]thiophen-3-yl] methyl]-phenoxy]ethyl]pyrrolidinone,
(c) 6-hydroxy-3-[3-methoxy-4-[(2-oxopyrrolidin-1-yl) methyl]benzyl]-2-[4-[2-(1-pyrrolidinyl)ethoxy] phenyl]-benzo[b]thiophene, and
(d) 6-hydroxy-3-[3-methoxy-4-[(2-oxopyrrolidin-1-yl) methyl]benzyl]-2-[4-[2-(1-pyrrolidinyl)ethoxy] phenyl]-benzo[b]thiophene;
or a pharmaceutically acceptable salt thereof.

9. The salt as claimed in claim 1 which is an acid-addition salt made with an acid which provides a pharmaceutically acceptable anion.

10. A pharmaceutical formulation comprising in association with a pharmaceutically acceptable carrier, diluent or excipient, a compound of formula I (or a pharmaceutically acceptable salt thereof) as provided in claim 1.

11. A method of inhibiting thrombin comprising using an effective amount of thrombin inhibiting compound of formula I (or a pharmaceutically acceptable salt thereof) as claimed in claim 1.

12. A process for preparing a compound of formula I (or a pharmaceutically acceptable salt thereof) as claimed in claim 1 which is selected from
(a) for a compound of formula I in which A is methylene, reductively removing the hydroxy group of a corresponding alcohol of formula II;

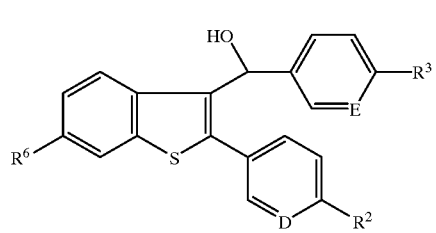

(b) for a compound of formula I in which $R^3$ is $CH_2R^c$ in which $R^c$ is cyano, cyclopentyl, 2-oxopyrrolidin-1-yl, 2,5-dioxopyrrolidin-1-yl, 2-oxooxazolidin-3-yl, 2-oxoimidazolidin-1-yl, 3-methyl-2-oxoimidazolidin-1-yl, 2-oxopyrrolidin-3-yl, 1-methyl-2-oxopyrrolidin-3-yl, 1-tetrazolyl or methoxy, alkylating the anion derived from a compound of formula H—$R^c$ using an alkylating agent corresponding to the compound of formula I, but in which $R^3$ is $CH_2X$ in which X is a conventional leaving group;
(c) for a compound of formula I in which $R^3$ is $-X^3-(CH_2)_n-L-R^c$ in which $X^3$ is O, alkylating the hydroxy group of a corresponding phenol of formula III

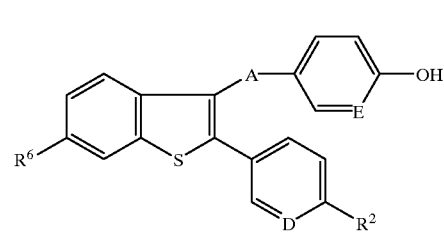

with a group of formula $X-(CH_2)_n-L-R^c$, wherein X is a conventional leaving group; and
(d) alkylating the nitrogen of a corresponding amine of formula H—$NR^aR^b$, using a compound corresponding to the compound of formula I, but in which $R^2$ is $-X^2-(CH_2)_m-X$ in which X is a conventional leaving group;
whereafter, for any of the above procedures, when a functional group is protected using a protecting group, removing the protecting group;
whereafter, for any of the above procedures, when a pharmaceutically acceptable salt of a compound of formula I is required, it is obtained by reacting the basic form of such a compound of formula I with an acid affording a physiologically acceptable counterion or by an other conventional procedure;
and wherein, unless otherwise described, A, D, E, $R^2$, $R^3$ and $R^6$ have the values described in claim 1.

13. The compound (or salt thereof) of claim 2 wherein
D is CH;
E is $CR^e$ in which $R^e$ is methyl or methoxy; and
$R^2$ is 2-(1-pyrrolidinyl)-ethoxy.

14. The compound (or salt thereof) of claim 3 wherein $R^3$ is (2-oxopyrolidin-1-yl)methyl or 2-(2-oxopyrrolidin-1-) ethoxy.

15. The compound (or salt thereof) of any one of claims 2 and 4 wherein $R^{3n}$ is (2-oxopyrrolidin-1-yl)methyl or 2-(2-oxopyrrolidin-1-yl)ethoxy.

16. The compound (or salt thereof) of claim 3 wherein $R^3$ is (2-oxopyrrolidin 1-yl)methyl or 2-(2-oxopyrrolidin-1-yl)ethoxy.

17. The compound (or salt thereof) of any one of claims 2, 4 and 5 wherein $R^6$ is hydroxy.

18. The compound (or salt thereof) of claim 3 wherein $R^6$ is hydroxy.

19. The compound (or salt thereof) of any one of claims 2, 4, 5 and 6 wherein A is methylene.

20. The compound (or salt thereof) of claim 3 wherein A is methylene.

\* \* \* \* \*